(12) United States Patent
Worm

(10) Patent No.: US 7,989,429 B2
(45) Date of Patent: Aug. 2, 2011

(54) LNA ANTAGONISTS TARGETING THE ANDROGEN RECEPTOR

(75) Inventor: Jesper Worm, Copenhagen (DK)

(73) Assignees: Enzon Pharmaceuticals, Inc., Bridgewater, NJ (US); Santaris Pharma A/S, Hoersholm (DK)

( * ) Notice: Subject to any disclaimer, the term of this patent is extended or adjusted under 35 U.S.C. 154(b) by 0 days.

(21) Appl. No.: 12/726,554

(22) Filed: Mar. 18, 2010

(65) Prior Publication Data

US 2010/0234451 A1    Sep. 16, 2010

Related U.S. Application Data

(63) Continuation of application No. 12/324,033, filed on Nov. 26, 2008, now Pat. No. 7,737,125.

(60) Provisional application No. 60/990,125, filed on Nov. 26, 2007.

(51) Int. Cl.
*A61K 48/00* (2006.01)
*C07H 21/04* (2006.01)

(52) U.S. Cl. ... 514/44; 536/23.1; 536/24.31; 536/24.33; 536/24.5

(58) Field of Classification Search ........................ None
See application file for complete search history.

(56) References Cited

U.S. PATENT DOCUMENTS

| | | | |
|---|---|---|---|
| 4,914,210 | A | 4/1990 | Levenson et al. |
| 4,962,029 | A | 10/1990 | Levenson et al. |
| 6,733,776 | B1 | 5/2004 | Li et al. |
| 7,067,256 | B2 | 6/2006 | Roy et al. |
| 7,087,229 | B2 | 8/2006 | Zhao et al. |
| 2004/0235773 | A1 | 11/2004 | Zhao et al. |
| 2005/0159376 | A1 | 7/2005 | McSwiggen et al. |
| 2005/0164970 | A1 | 7/2005 | Li |

FOREIGN PATENT DOCUMENTS

| | | |
|---|---|---|
| EP | 0692972 | 10/1994 |
| WO | 97/11170 | 3/1997 |
| WO | WO97/11170 | 3/1997 |
| WO | 01/83740 | 11/2001 |
| WO | WO01/83740 | 11/2001 |
| WO | 2004/046160 | 6/2004 |
| WO | WO2004/046160 | 6/2004 |
| WO | 2004/063331 A2 | 7/2004 |
| WO | WO 2004/063331 A2 | 7/2004 |
| WO | 2005/027833 | 3/2005 |
| WO | WO2005/027833 | 3/2005 |
| WO | 2007/031081 | 3/2007 |
| WO | 2007/031091 | 3/2007 |
| WO | WO2007/031081 | 3/2007 |
| WO | WO2007/031091 | 3/2007 |
| WO | 2007/146511 A2 | 12/2007 |
| WO | WO2007/146511 A2 | 12/2007 |
| WO | 2008/034122 | 3/2008 |
| WO | 2008/034123 | 3/2008 |
| WO | WO2008/034122 | 3/2008 |
| WO | WO2008/034123 | 3/2008 |
| WO | 2008053314 | 5/2008 |
| WO | WO2008/053314 | 5/2008 |

OTHER PUBLICATIONS

Kurreck et al., Design of antisense oligonucleotides stabilized by locked nucleic acids. Nucleic Acids Research, vol. 30, pp. 1911-1918, 2002.
Eder et al., Inhibition of LNCaP prostate cancer cells by means of androgen receptor antisense oligonucleotides. Cancer Gene Therapy, vol. 7, pp. 997-1007, 2000.
Beane et al., Inhibiting gene expression with locked nucleic acids (LNAs) that target chromosomal DNA. Biochemistry vol. 46, oo. 7572-7580, 2007.
International Search Report issued in PCT/DK2008/000417 and dated Jun. 16, 2009.
Akinc, et al., "A combinatorial library of lipid-like materials for delivery of RNAi therapeutics," Nature Biotechnology, vol. 26, pp. 561-569, 2008.
Freier & Altmann; "The ups and downs of nucleic acid duplex stability: structure-stability studies on chemically-modified DAN:RNA duplexes", Nucl. Acid Research, vol. 25, pp. 4429-4443, 1997.
Manoharan, et al., "Novel Funictionalization of the Sugar Moiety of Nucleic Acids for Multiple Labeling in the Minor Groove", Tetrahedron Letters, vol. 32, pp. 7171-7174, 1991.
Monks, et al., "Overexpression of wild-type androgen receptor in muscle recapitulates polyglutamine disease", PNAS, vol. 104, pp. 18259-18264, Nov. 13, 2007.
Uhlmann, Eugen, "Recent advances in the medicinal chemistry of antisense oligonucleotides", Curr. Opinion in Drug Development, vol. 3, pp. 203-213, 2000.
Zhao et al., "A New Platform for Oligonucleotide Delivery Utilizing the PEG Prodrug Approach", Bioconjugate Chemistry, vol. 16, pp. 758-766, 2005.
Zhao et al., "Delivery of G3139 using releasable PEG-linkers: Impact on pharmacokinetic profile and anti-tumor efficacy", J. of Controlled Release, vol. 119, pp. 143-152, 2007.
Beane et al., Inhibiting gene expression with locked nucleic acids (LNAs) that target chromosomal DNA. Biochemistry vol. 46, pp. 7572-7580, 2007.
Akinc, et al., "A combinatorial library of lipid-like materials for delivery of RNAi therapeutics," Nature Biotechnology, vol. 26, No. 5, pp. 561-569, 2008.
Freier & Altmann; "The ups and downs of nucleic acid duplex stability: structure-stability studies on chemically-modified DAN:RNA duplexes," Nucl. Acid Research, vol. 25, No. 22, pp. 4429-4443, 1997.
Manoharan, et al., "Novel Funictionalization of the Sugar Moiety of Nucleic Acids for Multiple Labeling in the Minor Groove," Tetrahedron Letters, vol. 32, No. 49, pp. 7171-7174, 1991.

(Continued)

*Primary Examiner* — Amy Bowman
(74) *Attorney, Agent, or Firm* — Lucas & Mercanti, LLP

(57) ABSTRACT

The invention relates to oligonucleotide compounds (oligomers), which target androgen receptor mRNA in a cell, leading to reduced expression of the androgen receptor. Reduction of the androgen receptor expression is beneficial for the treatment of certain disorders, such as a hyperproliferative disorders (e.g., cancer). The invention provides therapeutic compositions comprising oligomers and methods for modulating the expression of androgen receptor using said oligomers, including methods of treatment.

10 Claims, 22 Drawing Sheets

OTHER PUBLICATIONS

Monks, et al., "Overexpression of wild-type androgen receptor in muscle recapitulates polyglutamine disease," PNAS, vol. 104, No. 46, pp. 18259-18264, Nov. 13, 2007.

Uhlmann, Eugen, "Recent advances in the medicinal chemistry of antisense oligonucleotides," Curr. *Opinion in Drug Development*, Vo. 3, No. 2, pp. 203-213, 2000.

Zhao, et al., "A New Platform for Oligonucleotide Delivery Utilizing the PEG Prodrug Approach," *Bioconjudate Chemistry*, vol. 16, No. 4, pp. 758-766, 2005.

Zhao, et al., "Delivery of G3139 using releasable PEG-linkers: Impact on pharmacokinetic profile and anti-tumor efficacy," *J. of Controlled Release*, vol. 119, pp. 143-152, 2007.

Figure 3
Alignment human and mouse AR mRNA

```
                        1                                                50
NM_013476     (1)    ------------------------------------------------------
NM_000044     (1)    CGAGATCCCGGGGAGCCAGCTTGCTGGGAGAGCGGGACGGTCCGGAGCAA
Consensus     (1)
                        51                                               100
NM_013476     (1)    ------------------------------------------------------
NM_000044    (51)    GCCCAGAGGCAGAGGAGGCGACAGAGGGAAAAGGGGCCGAGCTAGCCGCT
Consensus    (51)
                        101                                              150
NM_013476     (1)    ------------------------------------------------------
NM_000044   (101)    CCAGTGCTGTACAGGAGCCGAAGGGACGCACCACGCCAGCCCCAGCCCGG
Consensus   (101)
                        151                                              200
NM_013476     (1)    ------------------------------------------------------
NM_000044   (151)    CTCCAGCGACAGCCAACGCCTCTTGCAGCGCGGCGGCTTCGAAGCCGCCG
Consensus   (151)
                        201                                              250
NM_013476     (1)    ------------------------------------------------------
NM_000044   (201)    CCCGGAGCTGCCCTTTCCTCTTCGGTGAAGTTTTTAAAAGCTGCTAAAGA
Consensus   (201)
                        251                                              300
NM_013476     (1)    ------------------------------------------------------
NM_000044   (251)    CTCGGAGGAAGCAAGGAAAGTGCCTGGTAGGACTGACGGCTGCCTTTGTC
Consensus   (251)
                        301                                              350
NM_013476     (1)    ------------------------------------------------------
NM_000044   (301)    CTCCTCCTCTCCACCCCGCCTCCCCCCACCCTGCCTTCCCCCCCTCCCCC
Consensus   (301)
                        351                                              400
NM_013476     (1)    ------------------------------------------------------
NM_000044   (351)    GTCTTCTCTCCCGCAGCTGCCTCAGTCGGCTACTCTCAGCCAACCCCCCT
Consensus   (351)
                        401                                              450
NM_013476     (1)    ------------------------------------------------------
NM_000044   (401)    CACCACCCTTCTCCCCACCCGCCCCCCCGCCCCCGTCGGCCCAGCGCTGC
Consensus   (401)
                        451                                              500
NM_013476     (1)    ------------------------------------------------------
NM_000044   (451)    CAGCCCGAGTTTGCAGAGAGGTAACTCCCTTTGGCTGCGAGCGGGCGAGC
Consensus   (451)
                        501                                              550
NM_013476     (1)    ------------------------------------------------------
NM_000044   (501)    TAGCTGCACATTGCAAAGAAGGCTCTTAGGAGCCAGGCGACTGGGGAGCG
Consensus   (501)
                        551                                              600
NM_013476     (1)    ------------------------------------------------------
NM_000044   (551)    GCTTCAGCACTGCAGCCACGACCCGCCTGGTTAGGCTGCACGCGGAGAGA
Consensus   (551)
                        601                                              650
NM_013476     (1)    ------------------------------------------------------
NM_000044   (601)    ACCCTCTGTTTTCCCCCACTCTCTCTCCACCTCCTCCTGCCTTCCCCACC
Consensus   (601)
                        651                                              700
NM_013476     (1)    ------------------------------------------------------
NM_000044   (651)    CCGAGTGCGGAGCCAGAGATCAAAAGATGAAAAGGCAGTCAGGTCTTCAG
Consensus   (651)
                        701                                              750
NM_013476     (1)    ------------------------------------------------------
NM_000044   (701)    TAGCCAAAAAACAAAACAAACAAAAACAAAAAAGCCGAAATAAAAGAAAA
Consensus   (701)
                        751                                              800
NM_013476     (1)    ------------------------------------------------------
```

Figure 3 (cont'd)

```
NM_000044    (751)  AGATAATAACTCAGTTCTTATTTGCACCTACTTCAGTGGACACTGAATTT
Consensus    (751)  801                                               850
NM_013476      (1)  --------------------------------------------------
NM_000044    (801)  GGAAGGTGGAGGATTTTGTTTTTTTCTTTTAAGATCTGGGCATCTTTTGA
Consensus    (801)  851                                               900
NM_013476      (1)  --------------------------------------------------
NM_000044    (801)  ATCTACCCTTCAAGTATTAAGAGACAGACTGTGAGCCTAGCAGGGCAGAT
Consensus    (801)  901                                               950
NM_013476      (1)  --------------------------------------------------
NM_000044    (901)  CTTGTCCACCGTGTGTCTTCTTCTGCACGAGACTTTGAGGCTGTCAGAGC
Consensus    (901)  951                                              1000
NM_013476      (1)  --------------------------------------------------
NM_000044    (951)  GCTTTTTGCGTGGTTGCTCCCGCAAGTTTCCTTCTCTGGAGCTTCCCGCA
Consensus    (951)  1001                                             1050
NM_013476      (1)  --------------------------------------------------
NM_000044   (1001)  GGTGGGCAGCTAGCTGCAGCGACTACCGCATCATCACAGCCTGTTGAACT
Consensus   (1001)  1051                                             1100
NM_013476      (1)  ----------------------------------------GAATTCGGTGGAAGCTA
NM_000044   (1051)  CTTCTGAGCAAGAGAAGGGGAGGCGGGTAAGGGAAGTAGGTGGAAGATT
Consensus   (1051)                                          GAA TAGGTGGAAG T
                    1101                                             1150
NM_013476     (18)  CAGACAAGCTCAAGGATGGAGGTGCAGTTAGGGCTGGGAAGGGTCTACCC
NM_000044   (1101)  CAGCCAAGCTCAAGGATGGAAGTGCAGTTAGGGCTGGGAAGGGTCTACCC
Consensus   (1101)  CAG CAAGCTCAAGGATGGA GTGCAGTTAGGGCTGGGAAGGGTCTACCC
                    1151                                             1200
NM_013476     (68)  ACGGCCGCCGATCCAAGACCTATCGAGGAGCGTTCCAGAATCTGTTCCAGA
NM_000044   (1151)  TCGGCCGCCGGTCCAAGACCTACCGAGGAGCTTTCCAGAATCTGTTCCAGA
Consensus   (1151)  CGGCC CC TCCAAGACCTA CGAGGAGC TTCCAGAATCTGTTCCAGA
                    1201                                             1250
NM_013476    (118)  GCGTGCGCAAGCGATCCAGAACCCGGGCCCCAGGCACCCTGAGGCCGT
NM_000044   (1201)  GCGTGCGCAAGTGATCCAGAACCCGGGCCCCAGGCACCCAGAGGCCGGG
Consensus   (1201)  GCGTGCGCAAG GATCCAGAACCCGGGCCCCAGGCACCC GAGGCCGC
                    1251                                             1300
NM_013476    (168)  AACATAGCGCCTCCCGGCGCCTGTTTAC----------------------
NM_000044   (1251)  AGCGCAGCGCCTCCCGGCGCCAGTTTGCTGCTGCTGCAGCAGCAGCA
Consensus   (1251)  A C  AGCGCCTCCCGGCGCC GTTT C
                    1301                                             1350
NM_013476    (196)  ---------------------------------------AGCAGA
NM_000044   (1301)  GCAGCAGCAGCAGCAGCAGCAGCAGCAGCAGCAGCAGCAGCAGCAGC
Consensus   (1301)                                              AGCAG
                    1351                                             1400
NM_013476    (202)  GGCAGGAGACTAGCCCCCGGCGGCGGCGGCGGCAGCAGCACACTGAGGAT
NM_000044   (1351)  AGCAAGAGACTAGCCCCAGGCAGCAGCAG---CAGCAGCAGGGTGAGGAT
Consensus   (1351)   GCA GAGACTAGCCCC GGC GC GC G   CAGCAGCA    TGAGGAT
                    1401                                             1450
NM_013476    (252)  GGTTCTCCTCAAGCCCACATCAGAGGCCCCACAGGCTACCTGGCCCTGGA
NM_000044   (1398)  GGTTCTCCCCAAGCCCATCGTAGAGGCCCCACAGGCTACCTGGCCTGGA
Consensus   (1401)  GGTTCTCC CAAGCCCA   AGAGGCCCCACAGGCTACCTGG CCTGGA
                    1451                                             1500
NM_013476    (302)  GGAGGAACAGCAGCCTTCACAGCAGCAGGCAGCCTCCGAGGGCCACCCTG
NM_000044   (1448)  TGAGGAACAGCAACCTTCACAGCCGCAGTCGGCCTGGAGTGCCACCCCG
Consensus   (1451)  GAGGAACAGCA CCTTCACAGC GCAG C GCC    GAG GCCACCC G
```

Figure 3 (cont'd)

```
                   1501                                          1550
NM_013476   (352)  AGAGCAGCTGCCTCCCCGAGCCTGGGCGGCCACCGGTCCTGGCAAGGGG
NM_000044  (1498)  AGAGAGCTTGCGTCCCAGAGCCTGGAGCCGCCGTGCCCGCAGCAAGGGG
Consensus  (1501)  AGAG G TGC TCCC GAGCCTGG GC GCC   GC C  GCAAGGGG
                   1551                                          1600
NM_013476   (402)  CTGCCGCAGCAGCCACCAGCTCCTCCAGATCAGGATGACTCAGCTGCCCC
NM_000044  (1548)  CTGCCGCAGCAGTGCCAGCACCTCCGGACGAGGATGACTCAGCTGCCCC
Consensus  (1551)  CTGCCGCAGCAGC CCAGC CCTCC GA  AGGATGACTCAGCTGCCCC
                   1601                                          1650
NM_013476   (452)  ATCCACGTTGTCCCTGCTGGGCCCCACTTTCCCACGCTTAAGCAGCTGCT
NM_000044  (1598)  ATCCACGTTGTCCCTGCTGGGCCCCACTTTCCCCGGCTTAAGCAGCTGCT
Consensus  (1601)  ATCCACGTTGTCCCTGCTGGGCCCCACTTTCCC GGCTTAAGCAGCTGCT
                   1651                                          1700
NM_013476   (502)  CCGCCGACATTAAAGACATTTTGAACGAGGCCGGCACCATGCAACTTCTT
NM_000044  (1648)  CCGCTGACATTAAAGACATCCTGACCGAGGCCAGCACCATGCAACTCCTT
Consensus  (1651)  CCGC GAC TTAAAGACAT  TGA CGAGGCC GCACCATGCAACT CTT
                   1701                                          1750
NM_013476   (552)  CAGCAGCAGCAACAACAGCAGCAGCACCAACAGCAGCACCAACAGCACCA
NM_000044  (1698)  CAGCA------ACAGCAGCAGGA--------------------------A
Consensus  (1701)  CAGCA      ACA CAGCAG A
                   1751                                          1800
NM_013476   (602)  ACAGCAGCAAGGAGGTAATCTCCGAAGGCAGCAGCGCAAGAGCCAGGGAGG
NM_000044  (1716)  GCAGTATCCGAAGGCA---------G-CAGCAGCGGGAGAGCGAGGGAGG
Consensus  (1751)   CAG A C G AGG A         G CAGCAGCG  AGAGC AGGGAGG
                   1801                                          1850
NM_013476   (652)  CCACGGGGGCTCCCTCTTCCTCCAAGGATAGTTACCTAGGGGCAATTCA
NM_000044  (1756)  CCTCGGGGGCTCCCACTTCCTCCAAGGACAATTACTTAGGGGCACTTGG
Consensus  (1801)  CC CGGGGGCTCCC CTTCCTCCAAGGA A TTAC TAGGGGCA TTC
                   1851                                          1900
NM_013476   (702)  ACCATATCTGACAGTGCCAAGGAGTTGTGTAAAGCAGTGTCTGTGTCCAT
NM_000044  (1806)  ACCATTTCTGACAACGCCAAGGAGTTGTGTAAGGCAGTGTCGGTGTCCAT
Consensus  (1851)  ACCAT TCTGACA  GCCAAGGAGTTGTGTAA GCAGTGTC GTGTCCAT
                   1901                                          1950
NM_013476   (752)  GGGATTGGGTGTGGAAGCATTGGAACATCTGAGTCCAGGGGAACAGCTTC
NM_000044  (1856)  GGGCCTGGGTGTGGAGGCGTTGGAGCATCTGAGTCCAGGGGAACAGCTTC
Consensus  (1901)  GGG  TGGGTGTGGA GC TTGGA CATCTGAGTCCAGGGGAACAGCTTC
                   1951                                          2000
NM_013476   (802)  GGGAGACTGCATGTACGCGTCCCTCCTGGGAGCTCCACCCGCGGTGCGT
NM_000044  (1906)  GGGGGGATTGCATGTACGCCCGGCTTTTGGGAGTTCCACCCGCTGTGCGT
Consensus  (1951)  GGGG  GA TGCATGTACGC  C T  TGGGAG TCCACCCGC GTGCGT
                   2001                                          2050
NM_013476   (852)  CCCACTCCTTGTGCCCGGCTGCCCGAATGCAAAGGTCTTCCCTGGACGA
NM_000044  (1956)  CCCACTCCTTGTGCCCCATTGCCCGAATGCAAAGGTTCTGTGCTAGACGA
Consensus  (2001)  CCCACTCCTTGTGC CC  TG CCGAATGCAAAGGT TC CT GACGA
                   2051                                          2100
NM_013476   (902)  AGGCCCAGGCAAAAGCACTGAAGACACTGCTGAGTATTCCTCTTTCAAGG
NM_000044  (2006)  CGGCCCAGGCAAGAGCACTGAAGATACTGCTGAGTATTCCCCTTTCAAGG
Consensus  (2051)    GC CAGGCAA AGCACTGAAGA ACTGCTGAGTATTCC CTTTCAAGG
                   2101                                          2150
NM_013476   (952)  GAGGTTACGCCAAAGGATTTGGAAGGTGAGAGCTTGGGCTGCTCTGGCAGC
NM_000044  (2056)  GAGGTTACACCAAAGGCGCAGAAGGCGAGAGCCTAGGCTGCTCTGGCAGC
Consensus  (2101)  GAGGTTAC CCAAAGG T GAAGG GAGAGC T GG TGCTCTGGCAGC
```

Figure 3 (cont'd)

```
                  2151                                         2200
NM_013476  (1002) AGTGAAGCAGGTAGCTCTGGGACACTTGAGATCCCGTCCTGTCTGTCTCT
NM_000044  (2106) GCTTGCAGCAGGGAGCTCCGGGACACTTGAACTGCCGTCTACCCTGTCTCT
Consensus  (2151)    TG AGCAGG AGCTC GGGACACTTGA  T CCGTC  C CTGTCTCT
                  2201                                         2250
NM_013476  (1052) GTATAAATCTGGAGCACTAGACGAGGCAGCAGGATACCAGAATCGCGACT
NM_000044  (2156) CTATAAATCTGGAGCACTGGACGAGGCAGCTGGGTACCAGAGTCGCGACT
Consensus  (2201)   TA AA TC GGAGCACT GACGAGGCAGC GC TACCAGA TCGCGACT
                  2251                                         2300
NM_013476  (1102) ACTACAACTTTCCGCTGGCTCTGTCCGGGCCGCCGCACCCCCCGCCCCCT
NM_000044  (2206) ACTACAACTTTCCACTGGCTCTGGCCGGACCGCCGCCCCCTCCGCCGCCT
Consensus  (2251) ACTACAACTTTCC CTGGCTCTG CCGG CCGCCGC CCC CCGCC CCT
                  2301                                         2350
NM_013476  (1152) ACCCATCCACACGCCCGTATCAAGCTGGAGAACCCATTGGACTACGGCAG
NM_000044  (2256) CCCCATCCCCACGCTCGCATCAAGCTGGAGAACCCGCTGGACTACGGCAG
Consensus  (2301)  CCCATCC CACGC CG ATCAAGCTGGAGAACCC  TGGACTACGGCAG
                  2351                                         2400
NM_013476  (1202) CGCCTGGGCTGCGGCGGAGCGCAATGCCGCTATGGGGACTTGGTACTC
NM_000044  (2306) CGCCTGGGCGGCTGCGGCGGCGCAGTGCCGCTATGGGGACCTGGCCAGCC
Consensus  (2351) CGCCTGGGC GC GCGGC GCGCA TGCCGCTATGGGGAC TGG  AG C
                  2401                                         2450
NM_013476  (1252) TACATGGAGGCAGTGTAGCCGGGCCCAGCACTGGATCGCCCCCAGCCACC
NM_000044  (2356) TGCATGGCCGCGGTGCAGCGGGACCCGGTTCTGGCTCACCCTCAGCCGCC
Consensus  (2401) T CATGG G G GTG AGC GG CCC G CTGG TC CCC CAGCC CC
                  2451                                         2500
NM_013476  (1302) ACCTCTTCTTCCTGGCATACTCTCTTCACAGCTGAAGAAGGCCAATTATA
NM_000044  (2406) GCTTCCTCATCCTGGCACACTCTCTTCACAGCCGAAGAAGGCCAGTTGTA
Consensus  (2451)   C TC TC TCCTGGCA ACTCTCTTCACAGC GAAGAAGGCCA TT TA
                  2501                                         2550
NM_013476  (1352) TGGCCCA-------------------------------------------G
NM_000044  (2456) TGGACCGTGTGGTGGTGGTGGGGGTGGTGGCGGCGGCGGCGGCGGCGGCG
Consensus  (2501) TGG CC                                           G
                  2551                                         2600
NM_013476  (1360) GACGCGGGGGCGGCAGCAGCAGCCCAAGCGATTGCCGGGCCTGTAGCCCCC
NM_000044  (2506) GCGGCGGCGGCGGCGGCGGCCCGGGCGGCGAGGCCGGAGCTGTAGCCCCC
Consensus  (2551) G  GGCGG GGCGGC GC GC GC    GCGA GC GG  CTGTAGCCCCC
                  2601                                         2650
NM_013476  (1410) TATGGCTACACTCGGCCCCCTCAGGGGCTGACAACCCAGGACAGTGACTA
NM_000044  (2556) TACGGCTACACTCGGCCCCCTCAGGGGCTGACGCGGCCAGGAAAGCGACTT
Consensus  (2601) TA GGCTACACTCGGCCCCCTCAGGGGCTG C   GCCAGGA AG GACT
                  2651                                         2700
NM_013476  (1460) CTCTGCCTCCGAAGTGTGGTATCCTGGTGGAGTTGTGAACAGAGTACCCT
NM_000044  (2606) CACCGGACCCGATGTGTGGTACCCTGGCGGCATTGTGAGCAGAGTGCCCT
Consensus  (2651) C C GC  C GA GTGTGGTA CCTGG GG  T GTGA CAGAGT CCCT
                  2701                                         2750
NM_013476  (1510) ATCCCAGTCCCAATTGTGTCAAAAGTGAAATGGGACCTTGGATGGAGAAC
NM_000044  (2666) ATCCCAGTCCCACTTGTGTCAAAAGCGAAATGGGCCCTTGGATGGATAGC
Consensus  (2701) ATCCCAGTCCCA TTGTGTCAAAAG GAAATGGG CC TGGATGGA A C
                  2751                                         2800
NM_013476  (1560) TACTCCGGACCTTATCGGGACATGCGTTTGGACAGTACCAGGGACCATGT
NM_000044  (2706) TACTCCGGACCTTACGGGGACATGCGTTTGGAGACTGCCAGGGACCATGT
Consensus  (2751) TACTCCGGACCTTA GGGGACATGCGTTTGGA A T CCAGGGACCATGT
```

Figure 3 (cont'd)

```
                        2801                                              2850
NM_013476   (1610) TTTACCCATCGACTATTACTTTCCACCCCAGAAGACCTGCCTGATCTGTG
NM_000044   (2756) TTTGCCCATTGACTATTACTTTCCACCCCAGAAGACCTGCCTGATCTGTG
Consensus   (2801) TTT CCCAT GACTATTACTTTCCACCCCAGAAGACCTGCCTGATCTGTG
                        2851                                              2900
NM_013476   (1660) GAGATGAAGCTTCTGGCTGTCACTACGGAGCTCTCACTTGTGGCAGCTGC
NM_000044   (2806) GAGATGAAGCTTCTGGCTGTCACTATGGAGCTCTCACATGTGGAAGCTGC
Consensus   (2851) GAGATGAAGCTTCTGG TGTCACTA GGAGCTCTCAC TGTGG AGCTGC
                        2901                                              2950
NM_013476   (1710) AAGGTCTTCTTCAAAAGAGCCGCTGAAGGGAAACAGAAGTATCTATGTGC
NM_000044   (2856) AAGGTCTTCTTCAAAAGAGCCGCTGAAGGGAAACAGAAGTACCTGTGCGC
Consensus   (2901) AAGGTCTTCTTCAAAAGAGCCGCTGAAGGGAAACAGAAGTA CT TG GC
                        2951                                              3000
NM_013476   (1760) CAGCAGAAACGATTGTACCATTGATAAATTTCGGAGGAAAAATTGCCCAT
NM_000044   (2906) CAGCAGAAATGATTGCACTATTGATAAATTCCGAAGGAAAAATTGTCCAT
Consensus   (2951) CAGCAGAAA GATTG AC ATTGATAAATT CG AGGAAAAATTG CCAT
                        3001                                              3050
NM_013476   (1810) CTTGTCGTCTCCGGAAATGTTATGAAGCAGGGATGACTCTGGGAGCTCGT
NM_000044   (2956) CTTGTCGTCTTCGGAAATGTTATGAAGCAGGGATGACTCTGGGAGCCCGG
Consensus   (3001) CTTGTCGTCT CGGAAATGTTATGAAGCAGGGATGACTCTGGGAGC CG
                        3051                                              3100
NM_013476   (1860) AAGCTGAAGAAACTTGGAAATCTAAAACTACAGGAGGAAGGAGAAAACTG
NM_000044   (3006) AAGCTGAAGAAACTTGGTAATCTGAAACTACAGGAGGAAGGAGAGGCTTC
Consensus   (3051) AAGCTGAAGAAACTTGG AATCT AAACTACAGGAGGAAGGAGA     TC
                        3101                                              3150
NM_013476   (1910) CAATGCTGGCAGCCCCACTGAGGACCATCCCAGAAGATGACTGTATCAC
NM_000044   (3056) CAGCACCACCAGCCCCACTGAGGAGACAACCCAGAAGCTGACAGTGTCAC
Consensus   (3101) CA  C    CAGCCCCACTGAGGA  CA  CCCAGAAG TGAC GT TCAC
                        3151                                              3200
NM_013476   (1960) ACATTGAAGGCTATGAATGTCAGCCTATCTTTCTTAAGGTCCTGGAAGCC
NM_000044   (3106) ACATTGAAGGCTATGAATGTCAGCCCATCTTTCTGAATGTCCTGGAAGCC
Consensus   (3151) ACATTGAAGGCTATGAATGTCAGCC ATCTTTCT AA GTCCTGGAAGCC
                        3201                                              3250
NM_013476   (2010) ATTGAGCCAGGAGTCGTGTGTGCCGGACATGACAACAACCAACCAGATTC
NM_000044   (3156) ATTGAGCCAGGTGTAGTGTGTGCTGGACAGGACAACAACCAGCCCGACTC
Consensus   (3201) ATTGAGCCAGG GT GTGTGC GGACA GACAACAACCA CC GA TC
                        3251                                              3300
NM_013476   (2060) CTTTGCTGCCTTGTTAGTCTAGCCTCAATGAGCTTGGAGAGAGCCAGCTTG
NM_000044   (3206) CTTTGCAGCCTTGCTTCTCTAGCCTCAATGAACTGGGAGAGACACAGCTTG
Consensus   (3251) CTTTGC GCCTTG T TCTAGCCTCAATGA CT GGAGAGAG CAGCTTG
                        3301                                              3350
NM_013476   (2110) TCCATGTGGTCAAGTGGGCCAAGGCCTTGCCTGGCTTCCGCAACTTGCAT
NM_000044   (3256) TACACGTGGTCAAGTGGGCCAAGGCCTTGCCTGGCTTCCGCAACTTACAC
Consensus   (3301) T CA GTGGTCAAGTGGGCCAAGGCCTTGCCTGGCTTCCGCAACTT CA
                        3351                                              3400
NM_013476   (2160) GTGGATGACCAGATGGCGGTCATTCAGTATTCCTGGATGGGACTGATGGT
NM_000044   (3306) GTGGACGACCAGATGGCTGTCATTCAGTACTCCTGGATGGGCCTCATGGT
Consensus   (3351) GTGGA GACCAGATGGC GTCATTCAGTA TCCTGGATGGG CT ATGGT
                        3401                                              3450
NM_013476   (2210) ATTTGCCATGGGTTGGCGGTCCTTCACTAATGTCAACTCCAGGATGCTCT
NM_000044   (3356) GTTTGCCATGGGCTGGCGATCCTTCACCAATGTCAACTCCAGGATGCTCT
Consensus   (3401)  TTTGCCATGGG TGGCG TCCTTCAC AATGTCAACTCCAGGATGCTCT
```

Figure 3 (cont'd)

```
                 3451                                              3500
NM_013476  (2260) ACTT GCA CCTGA C TGGTTTTCAATGAGTACCGCATGCACAAGTC CGG
NM_000044  (3406) ACTT GCC CCTGA TC TGGTTTTCAATGAGTACCGCATGCACAAGTC CGG
Consensus  (3451) ACTT GC  CCTGA    TGGTTTTCAATGAGTACCGCATGCACAAGTC CGG
                 3501                                              3550
NM_013476  (2310) ATGTACAGCCAGTGTGTGAG ATGAGGCACCT GTCTCAAGAGTTTGGATG
NM_000044  (3456) ATGTACAGCCAGTGTGTCC GA ATGAGGCACCT CTCTCAAGAGTTTGGATG
Consensus  (3501) ATGTACAGCCAGTGTGT    G ATGAGGCACCT  TCTCAAGAGTTTGGATG
                 3551                                              3600
NM_013476  (2360) GCTCCAAATA ACCCCCCAGGAATTCCTGTGCATGAAAGCACTGCT GCTCT
NM_000044  (3506) GCTCCAAATC ACCCCCCAGGAATTCCTGTGCATGAAAGCACTGCT ACTCT
Consensus  (3551) GCTCCAAAT  ACCCCCCAGGAATTCCTGTGCATGAAAGCACTGCT  CTCT
                 3601                                              3650
NM_013476  (2410) TCAGCATTATTCCAGTGGATGGGCTGAAAAATCAAAAATTCTTTGATGAA
NM_000044  (3556) TCAGCATTATTCCAGTGGATGGGCTGAAAAATCAAAAATTCTTTGATGAA
Consensus  (3601) TCAGCATTATTCCAGTGGATGGGCTGAAAAATCAAAAATTCTTTGATGAA
                 3651                                              3700
NM_013476  (2460) CTTCGAATGAACTACATCAAGGAACTCGATCG ATCATTGCATGCAAAAG
NM_000044  (3606) CTTCGAATGAACTACATCAAGGAACTCGATCG TATCATTGCATGCAAAAG
Consensus  (3651) CTTCGAATGAACTACATCAAGGAACTCGATCG  ATCATTGCATGCAAAAG
                 3701                                              3750
NM_013476  (2510) AAA GAATCCCACATCCTGCTCAAG GCGCTTCTACCAGCTCACCAAGCTCC
NM_000044  (3656) AAA AAATCCCACATCCTGCTCAAG ACGCTTCTACCAGCTCACCAAGCTCC
Consensus  (3701) AAA  AATCCCACATCCTGCTCAAG  CGCTTCTACCAGCTCACCAAGCTCC
                 3751                                              3800
NM_013476  (2560) TGGA TCT GTGCAGCCTATTGC AGAGAGCTGCATCAGTTCACTTTTGAC
NM_000044  (3706) TGGA CTC GTGCAGCCTATTGC GAGAGAGCTGCATCAGTTCACTTTTGAC
Consensus  (3751) TGGA  TC GTGCAGCCTATTGC  AGAGAGCTGCATCAGTTCACTTTTGAC
                 3801                                              3850
NM_013476  (2610) CTGCTAATCAAGTC CA ATGGTGAGCGTGGACTTTCCT GAAATGATGGC
NM_000044  (3756) CTGCTAATCAAGTC ACA ATGGTGAGCGTGGACTTTCCG GAAATGATGGC
Consensus  (3801) CTGCTAATCAAGTC  CA ATGGTGAGCGTGGACTTTCC  GAAATGATGGC
                 3851                                              3900
NM_013476  (2660) AGAGATCATCTCTGTGCAAGTGCCCAAGATCCTTTCTGGGAAAGTCAAGC
NM_000044  (3806) AGAGATCATCTCTGTGCAAGTGCCCAAGATCCTTTCTGGGAAAGTCAAGC
Consensus  (3851) AGAGATCATCTCTGTGCAAGTGCCCAAGATCCTTTCTGGGAAAGTCAAGC
                 3901                                              3950
NM_013476  (2710) CCATCTATTTCCACAC CAGTGAAG AT TGGAAACCCTA TA CCA AAA C
NM_000044  (3856) CCATCTATTTCCACAC CCAGTGAAG CA TGGAAACCCTA TTT CCC AC-C
Consensus  (3901) CCATCTATTTCCACAC  CAGTGAAG    TGGAAACCCTA T   CCC  A  C
                 3951                                              4000
NM_013476  (2760) CCA CCT TG TT CCCT-TTC CAGATGTCTTCTGCCTGTTAT AT AACTCTGCA
NM_000044  (3906) CCA GCT CA TG CCCCC TTT CAGATGTCTTCTGCCTGTTAT-- AACTCTGCA
Consensus  (3951) CCA  CT    T  CCC  TT  CAGATGTCTTCTGCCTGTTAT    AACTCTGCA
                 4001                                              4050
NM_013476  (2809) CTACT TCT CTGCAGTGCCTTGGGG GAAA TTCCTCTAC TGATGTACAGTCT
NM_000044  (3953) CTACT CCT CTGCAGTGCCTTGGGG-AAT TTCCTCTAT TGATGTACAGTCT
Consensus  (4001) CTACT  CT CTGCAGTGCCTTGGGG AA  TTCCTCTA  TGATGTACAGTCT
                 4051                                              4100
NM_013476  (2859) GTC TGAACA GTTCCT CA TTCTATTT C TGGGCTT ------- CTCC TT
NM_000044  (4002) GTCA TGAACA GTTCCT GA ATTCTATTTGC TGGGCTT TTTTTTT CTCT TT
Consensus  (4051) GTC  TGAACA GTTCCT  A  TTCTATTT C TGGGCTT          CTC TT
```

Figure 3 (cont'd)

```
                 4101                                              4150
NM_013476  (2902) CT-----TTTTTTTCTTCTTCCCTCCCTCTTTCACCCTCCCATGGCACA
NM_000044  (4052) CTCTCCTTTCTTTTTCTTCTTCCCTCCCTATCTAACCCTCCCATGGCACC
Consensus  (4101) CT     TT TTTTCTTCTTCCCTCCCT T T ACCCTCCCATGGCAC
                 4151                                              4200
NM_013476  (2947) TTTGAATCTGCTGCGTATTGTGGCTCCTGCCTTTGTTTTGATTCTGTT
NM_000044  (4102) TTCAGACTTTGCTTCCATTGTGGCTCCTATCTGTGTTTTGAATGGTGTT
Consensus  (4151) TT GA T TGCT C  ATTGTGGCTCCT CT TGTTTTGA T  TGTT
                 4201                                              4250
NM_013476  (2997) GTA-----------------------------------------------
NM_000044  (4152) GTATGCCTTTAAATCTGTGATGATCCTCATATGGCCCAGTGTCAAGTTGT
Consensus  (4201) GTA
                 4251                                              4300
NM_013476  (3000) --------------------------------------------------
NM_000044  (4202) GCTTGTTTACAGCACTACTCTGTGCCAGCCACACAAACGTTTACTTATCT
Consensus  (4251)
                 4301                                              4350
NM_013476  (3000) --------------------------------------------------
NM_000044  (4252) TATGCCACGGGAAGTTTAGAGAGCTAAGATTATCTGGGGAAATCAAAACA
Consensus  (4301)
                 4351      4363
NM_013476  (3000) -------------
NM_000044  (4302) AAAACAAGCAAAC
Consensus  (4351)
```

ORIGIN
```
   1 cgagatcccg gggagccagc ttgctgggag agcgggacgg tccgagcaa gcccagaggc
  61 agaggagcg acagagggaa aaaggccga gctagccgct ccagtgctgt acaggagccg
 121 aaggacgca ccacgccagc cccagccgg ctccagcgac agccaacgcc tcttgcagcg
 181 cggcggattc gaagccgccg cccggagctg cccttctc ttcggtgaag tttttaaaag
 241 ctgctaaaga ctcggaggaa gcaaggaaag tgcctggtag gactgacggc tgccttgtc
 301 ctcctcctct ccaccccgcc tcccccacc ctgccttccc ccctcccc gtctttctctc
 361 ccgcagctgc ctcagtcggc tactctcagc caacccct caccaccctt ctccccaccc
 421 gccccccagc cccgtcggc ccagcgctgc cagccgagt ttgcagagag gtaactccct
 481 ttggctgcga gcgggcgagc tagctgcaca ttgcaaagaa ggctcttagg agccaggcga
 541 gtcggagcg gcttcagcac tgcacaccg acccgcctgg ttaggatgca agcgagaga
 601 acccctctgtt ttccccact ctctctccac ctcctcctgc ctcccccacc ccgagtgcgg
 661 agccagagat caaagatga aaggcagtc aggtcttcag tagcaaaaaa acaaaacaaa
 721 caaaaacaaa aagccgaaa taaagaaaa agataataac tcagttctta tttgcaccta
 781 ctcagtggaa cactgaattt ggaaggtgga ggatttgtt tttttcttt agatatggg
 841 catcttttga atctacccttt caagtattaa gagacagact gtgagctag caggccagat
 901 cttgtccacc gtgtgtctc ttctgcacga gactttgagg ctgtcagagc gcttttgcg
 961 tggttgctcc cgcaagtttc cttctctgga gcttcccgca ggtgggcaga tagctgcagc
1021 gactaccgca tcatcacagc ctgttgaact cttctgagca agagaagggg aggcgggta
1081 agggaagtag gtggaagatt cagccagcct caaggatgga agtgagttta gcgctggaa
1141 gggtctaccc tcggccgagc tccaagacct accgggagc tttccagaat ctgttccaga
1201 ggtgctgcga agtgatccag aacccggcc ccaggcacc agaggcacgc agcgcagcac
1251 ctccggcggc cagtttgctg ctgctgcagc agcagcagca gcagcagcag cagcagcagc
1321 agcagcagca gcagcagcag cagcagcagc agcaagagac tagcccagg cagcagcagc
                                       SEQ ID NO:44                SEQ ID
NO:45
1381 agcagcaggg tgaggatggt tctccccaag cccatcgtag aggcccaca ggctacctgg
1441 tcctggatga ggaacagcaa cctcacagc cgcagtcggc cctggagtgc caccccgaga
1501 gaggttgcgt cccagagcct ggagccgcg tggcgccag caaggggctg ccgcagcagc
1561 tgcctgaca tccggacgag gatgactcag ctgccccatc cagcagtgtc ctgctgggag
1621 ccactttccc cggcttaagc agctgctccg ctgacctaa agacatcctg agcgaggca
1681 gcaccatgca actccttcag caacagcagc aggaagcagt atccgaaggc agcagcagcg
1741 ggagagcgag ggaggcctcg gggctccca cttcctccaa ggacaattac ctagggggca
1801 cttcgaccat ttctgacaac gccaaggagt gtgtaagcc agtgtcggtg tccatgggcc
                                           SEQ ID NO:46
1861 tgggtgtgga ggcgttggag catctgagtc cagggaaca gcttcggggg gattgcatgt
                                               SEQ ID NO:47
1921 acgcccact ttgggagtt ccaccgctg tggtcccac tccttgtgcc ccatggccg
1981 aatgcaaagg ttctctgcta gacgaagca caggcaaagc cactgaagat actgctgagt
2041 attccctttt caaggagg tacaccaaag gctagaag cgagagccta ggctgtctg
2101 gcagcgctgc agcaggagc tccggacac ttgaactgcc gtctaccctg tctctataca
2161 agtccggagc actggacgag gcagctgcgt accagagtcg cgactactac aactttccac
2221 tggctctgga cggaccgcg cccctcagc cgcctccca tccccaagct ccatcaagc
2281 tggagaaccg gctggactac ggcagcgct gggcggctgc ggcgcgcag tgccgctatg
2341 ggacctggc gagcctgcat ggcgagggtc cagcgggacc cggttctggg tcacctcag
                                          SEQ ID NO:48
2401 ccgccgcttc ctcatcctgg cacactctct tcacagccga agaaggccag ttgtatggac
2461 cgtgtgatgg tgtggggt ggtggctgca gcgcaggcga cgggggcgcg ggggcggcg
2521 gccggcggg aggcggccg ggactgtag cccctaccg cacactcagg cccctcagg
2581 ggctggcggg ccaggaaagc gacttcacga cacctgatgt gtggtaccct ggcggcatgg
                                           SEQ ID NO:51
2641 tgagcagagt gcccctatcc agtccacctt gtgtcaaaag cgaaatgggc cctggatgg
2701 atagctactc cggaccttac ggggacatgc gttgagac tgtcaggac catgtttgc
                                                                      SEQ
ID NO:54
2761 ccattgacta ttactttcca cccagaaga cctgcctgat ctgtggagat gaagcttctg
2821 ggtgtcacta tggagctctc acatgtggaa gctgcaaggt cttctcaaa agagccgctg
2881 aaggaaaca gaagtacctg tgggccagca gaaatgatty cactattgat aaattccgaa
2941 ggaaaaattg tccatcttgt cgtcttcgga aatgttatga agcagggatg actctgggag
       SEQ ID NO:58
```

Figure 4 (cont'd)

```
3001 ccggaagct gaagaaactt ggtaatctga aactacagga ggaaggagag gcttccagca
3061 ccaccagcc cactgaggag acaacccaga agctgacagt gtcacacatt gaaggctatg
          SEQ ID NO:60
3121 aatgtcagcc catctttctg aatgtcctgg aagccattga gccaggtgta gtgtgtgctg
3181 gacacgacaa caaccagccc gactcctttg cagccttgct ctcragcctc aatgaactgg
                                                       SEQ ID NO:61
3241 gagagagaca gcttgtacac gtggtcaagt gggccaagc cttgcctgc ttccgcaact
3301 tacacgtgga cgaccagatg gctgtcatte agtactcctg gatgggctc atggtgtttg
                                                 SEQ ID NO:62
3361 ccatgggctg gcgatcctte accaatgtca actccaggat gctctactte gccctgatc
                                                       SEQ ID NO:53
3421 tggttttcaa tgagtaccgc atgcacaagt ccggatgta cagccagtgt gtccgaatga
                                 SEQ ID NO:66                SEQ ID
NO:67
3481 ggcacctcte tcaagagttt ggatggctcc aaatcaccc ccaggaattc ctgtgcatga
                                                                SEQ ID
NO:68
3541 aagcactgct actcttcagc attattccag tggatgggct gaaaatcaa aattctttg
                                             SEQ ID NO:69
3601 atgaacttcg aatgaactac atcaaggaac tcgatcgtat cattcatgc aaagaaaaa
3661 atcccacatc ctgctcaaga cgcttctacc agctacttgca gctccggac tccgtcagc
3721 ctattgcgag agagctgcat cagttcactt ttgacctgct aatcaagtca cacatggtga
                                                    SEQ ID NO:72
3781 gcgtggactt tccggaaatg atggcagaga tcatctctgt gcaagtgccc aagatcttt
          SEQ ID NO:73
3841 ctggaaaagt caagcccatc tatttccaca cccagtgaag cattggaaac cctatttcc
                     SEQ ID NO:76
3901 caccccagct catgccccct tcagatgtc ttctgcctgt tataactctg cactactcct
          SEQ ID NO:77
3961 atgcaagtgcc ttgggaatt tcctctattg atgtacagtc tgtcatgaac atgttcctga
4021 attctatttg ctgggctttt ttttctctt tctctccttt cttttcttc ttccctcct
4081 atctaaccct ccatggcac cttcagacttt tcttccat tgtggctcct atctgtgttt
4141 tgaatggtgt tgtatgcctt taaatctgtg atgatcctca tatggccag tgtcaagttc
4201 tgcttgttta agcactact ctgtgccagc cacacaaacg ttacttatc ttatgccacg
4261 ggaagtttag agagctaaga ttatctgggg aaatcaaaac aaaaacaagc aaac
//
```

Figure 5

```
   1 cgagatcccg gggagccagc ttgctggag agcgggacgg tccggagcaa gcccagaggc
  61 agaggaggcg acagagggaa aaagggccga gctagccgct ccagtgtgt acaggagccg
 121 aagggacgca ccacgccagc cccagccgg ctccagcgac agccaaagcc tcttgcagcg
 181 cggcggttc gaagccgccg cccggagctg ttccttcctc ttcgtgaag ttttcaaaag
 241 ctgctgaaaga ctcggaggaa gcaagaaag tgcctggtag gactgacgc tgcctttgtc
 301 ctcctcctct ccaccccgcc tccccccacc ctgccttccc ccctccccc gtcttctctc
 361 ccgcagctgc ctcagtcggc tactctcagc caaccccct caacaccctt ctccccaccc
 421 gcccccccga ccccgtcggc ccagcgctgc cagccgagt ttgcagagag gtaactccct
 481 ttggctgcga gggcggagc tagctgcaca ttgcaaagaa ggctcttagg agccaggcga
 541 ctgggagcg gcttcagcac tgcagccacg acccgcctgg ttaggctgca ccggagaga
 601 acccctcttt ttccccact ctctctcac ctcctctgc cttccacc ccagtgcggg
 661 agccagagat caaaagatga aaaggcagtc aggtcttcag tagccaaaa acaaaacaaa
 721 caaacaaa aaagccgaaa taaaagacaa agataataac tcagttcttca tttgaccta
 781 cttcagtgga cactgaattt ggaaggtgga ggatttgtt tttctttt aagatctggg
 841 catctttga atctacctt caagtattaa gagacagact gtgagctag caggggagat
 901 cttgtccacc gtgtgtcttc ttctgcacga gacttgagg ctgtcagagc gctttttgcg
 961 tggttgctcc cgcaagtttc cttctctgga gcttcccgca gtgggcagc tagctgcagc
1021 gactaccgca tcatcacagc ctgttgaact cttctgagca agagaaggg aggcgggta
1081 agggaagtag gtggaagatt cagccaagct caaggatgga agtgcagtta gggctgggaa
1141 gggtctaccc tcggccgccg tccaagacct accgaggaac tttccagaat ctgttccaga
1201 gcgtgcgcga agtgatccag aaccccgggcc ccaggcaccc agaggccgcg agcgcagcac
1261 ctccggcgc cagtttgctg ctgctgcagc agcagcagca gcagcagcag cagcagcagc
1321 agcagcagca gcagcagcag cagcagcagc agcaagagac tagcccagg cagcagcagc
1381 agcagcaggg tgaggatggt tctcccaag cccatcgtag aggccccaca ggctacctgg
1441 tcctggatga ggaacagcaa cctcacagc cgcagtcggc cctggagtgc caccccgaga
1501 gaggttgcgt cccagagcct ggagccgcg tggccgccag caagggctc ccgcagcagc
1561 tgccccate tcgggacgag gatgactcag caccgtcgtcc ctgctggcc
1621 ccactttccc cggcttaagc agctgctccg ctgacttaa agacatcctg agcgaggcca
1681 gcaccatgca actccttcag caacagcagc aggaagcagt atccgaaggc agcagcagcg
1741 ggagagcgag ggaggcctcg ggggctccca cttcctccaa ggacaattac ttaggggca
1801 cttcgaccat ttctgacaac gccaaggagt tgtgtaaggc agtgctggtg tccatgggcc
1861 tgggtgtgga ggcgttggag catctgagtc cagggaaca gttcggggg gattgcatgt
1921 acgcccact tttgggagtt ccaccgctg tgctccac tccttgtgcc ccattggccg
1981 aatgcaaagg ttctctgcta gacgacagcg caggcaagag cactgaagat actgctgagt
2041 attcccttt caagggaggt tacacaaag ctgtagaagg cagagccta ggctgcctg
2101 gcagcgctgc agcaggagc tcgggacac ttgaactgcc gtctaccctg tctctctaca
2161 agtccggagc actggacgag gcagctgcgt accagagtcg cgactactac aactttccac
2221 tggctctggc cggaccgccg cccctccgc cgctcccca tccccacgct cgcatcaagc
2281 tggagaaccc gctgactac ggcagcgcct gggcgctgc ggcggcgcag tgccgctatg
2341 ggacctggc gagcctgcat ggcgcggtg cagggacc cgttctggg tcacctcag
2401 ccgccgcttc ctcatcctgg cacactctct tcacagccga agaaggccag ttgtatggac
2461 cgtgtggtg tggtgggg gtggcggcg gcgcggcag cgcggcgcg gccggcggcg
2521 ccccgagggc ggagggcg ggaggtgtag cccctaccgg ctacactcgg ccctccagg
2581 ggctggcggg ccaggaaagc gacttcaccg cacctgatgt gtggtccct ggccggatgg
2641 tgagcagagt gccctatccc agtccactt gtcaaaag cgaaatggc cctggatgg
2701 atagctactc cggacttac gggacatgc gtttggagac tgccaggac catgtttgc
2761 ccattgacta ttacttccca cccagaaga ctgcctgat ctgtggagat gaagcttctg
2821 ggtgtcacta tggagctctc acatgtggaa gctgcaaggt cttcttcaaa agagccgctg
2881 aagggaaaca gaagtacctg tgcgccagca gaaatgattg cactattgat aaattccgaa
2941 ggaaaaattg tccatcttgt cgtcttcgga aatacagga agaggagag gcttccagca
3001 ccggaagct gaagaaactt ggtactga aactacgga ggaggagag gcttccagca
3061 ccaccagcc cactgaggag acaaccaga agtgacagt gtcacactt gaaggctatg
3121 aatgtcagcc catctttctg aatgtcctgg aagccattga gcaggtgta gtgtgtctg
3181 gacacgacaa caacagccc gactccttg cagcctgct ctctagcctc aatgaactgg
3241 gagagagaca gcttgtacac gtggtcaagt gggccaaggc cttgcctggc ttcccaact
3301 tacacgtgga cgaccagatg gctgtcattc agtactcctg gatgggcctc atggtgtttg
3361 ccatgggctg gcgatccttc accaatgtca actccagat gctgtacttc gccctgatc
3421 tggtttttct tgagtaccga atgcacaagt cccggatgta cagcagtgt ccggaatga
3481 actccgaggc tcaagagttt ggatggctcc aaatatgccc ccaggaattc ctgtgcatga
3541 aagcactgct actcttcagc attattccag tggatgggct gaaaaatcaa aaatttttg
3601 atgaacttcg aatgaactac atcaaggaac tcgatcgtat cattgcatgc aaagaaaaa
3661 atcccacatc ctgtcaaga cgcttctacc agctcaccaa gctcctggac tccgtgcagc
3721 ctattgcgag agagctgcat cagttcactt ttgacctgct aatcaagtca cacatggtga
```

Figure 5 (cont'd)

```
3781 gcgtggactt tccggaastg atggcagaga tcatctctgt gcaagtgccc aagatccttt
3841 ctgggaaagt caagcccatc tatttccaca cccagtgaag cattggaaac cctatttccc
3901 caccccagct catgcccct ttcagatgtc ttctgcctgt tataactctg cactactcct
3961 ctgcagtgcc ttggggaatt tcctctattg atgtacagtc tgtcatgaac atgttcctga
4021 attctatttg ctgggctttt ttttctctt tctctcctt cttttctt ttccctcct
4081 atctaaccct cccatggcac cttcagactt tgcttcccat tgtggctcct atctgtgttt
4141 tgaatggtgt tgtatgcctt taastctgtg atgatcctca tatggccag tgtcaagttg
4201 tgcttgttta cagcactact ctgtgccagc cacacaaacg tttacttatc ttatgccaag
4261 ggaagtttag agagctaaga ttatctgggg aastcaaaac aaaaacaagc aaac
//
```

Figure 6

```
SEQ ID NO: 81
LOCUS       NM_013476       2999 bp    mRNA     linear
DEFINITION  Mus musculus androgen receptor (Ar), mRNA.
ACCESSION   NM_013476
VERSION     NM_013476.3  GI:118129906
SOURCE      Mus musculus (house mouse)
ORIGIN
    1 gaattcggtg gaagctacag acaagctcaa ggatggaggt gcagttaggg ctgggaaggg
   61 tctaccoacg gccccatcc aagacctatc gaggagcgtt ccagaatctg ttccagagcg
  121 tgcgcaagc gatccagaac ccgggcccca ggcaccctga ggccgctaac atagcacctc
  181 ccggcgcctg tttacagcag aggcaggaga ctagccccg gcggcggcgg cggcagcagc
  241 acactgagga tggttctcct caagcccaca tcagaggcc cacaggctac ctggccctgg
  301 aggaggaaca gcagccttca cagcagcagg cagcctcga gggccaccct gagagcagct
  361 gcctcccga gcctggggcg gccaccgctc ctggcaaggg gctgccgcag cagccaccag
  421 ctcctccaga tcaggatgac tcagctgccc catccacgtt gtccctgctg ggccccactt
  481 tcccaggctt aagcagctgc tccgccgaca ttaaagacat tttgaacgag gccggcacca
  541 tgcaacttct tcagcagcag caacaacagc agcagcacca acagcagcac aacagcacc
  601 aacagcagca ggagtaatc tccgaaggca gcagcgcaag agccagggag gccacggggg
  661 ctccctcttc ctccaaggat agttacctag ggggcaattc aaccatatct gacagtgcca
  721 aggagttgtg taaagcagtg tctgtgtcca tgggattggg tgtggaagca ttggaacatc
  781 tgagtccagg ggaacagctt cggggagact gcatgtacgc gtcgctcctg ggaggtccac
  841 ccgcggtgcg tccactcct tgtgcgccgc tgccgaatgc aaaggtcttt ccctggacg
  901 aaggcccagg caaaagcact gaagagactg ctgagtattc ctctttcaag ggaggttacg
  961 ccaaaggatt ggaaggtgag agcttggggt gctctggcag cagtgaagca ggtagctctg
 1021 ggacacttga gatcccgtcc tctctgtctc tgtataaatc tggagcacta gacgaggcag
 1081 cagcatacca gaatcgcgac tactacaact ttccgctggc tctgtccggc ccgcccgcacc
 1141 cccgcccc tacccatcca cacgcccgta tcaagctgga gaccccattg gactacggca
 1201 gcgcctgggc tgcggcggca gcgcaatgcc gctatgggga cttggtagt ctacatggag
 1261 ggagtgtagc cgggcccagc actggatcgc cccagccac cacctcttct tcctggcata
 1321 ctctcttcac agctgaagaa ggccaattat atggccagg aggcgggggc ggcagcagca
 1381 gcccaagcga tgccggggcct gtagcccct atggctacac tcggccccct cagggctga
 1441 caagccagga gagtgactac tctgcctccg aagtgtggta cctggtgga gttgtgaaca
 1501 gagtacccta tcccagtccc aattgtgtca aaagtgaaat gggaccttgg atggagaact
 1561 actccggacc ttatggggac atgcgtttgg acagtaccag ggaccatgtt ttacccatcg
 1621 actattactt tccaccccag aagacctgcc tgatctgtgg agatgaagct tctggctgtc
 1681 actacggagc tctcacttgt ggcagctgca aggtcttctt caaaagagcc gctgaaggga
 1741 aacagaagta tctatgtgcc agcagaaacg attgtaccat tgataaattt cggaggaaaa
 1801 attgcccatc ttgtcgtctc cggaaatgtt atgaagcagg atgactctg ggagctcgta
 1861 agctgaagaa actggaaat ctaaaactac aggaggaagg agaaaactcc aatgctggca
 1921 gccccactga ggacccatcc cagaagatga ctgtatcaca cattgaaggc tatgaatgtc
 1981 agcctatctt tcttaacgtc ctggaagcca ttgagcagg agtggtgtgt gcggacatg
 2041 acaacaacca accagattcc tttgctgcct tgttatctag cctcaatgag cttggagaga
 2101 ggcagcttgt gcatgtggtc aagtgggcca aggcttgcc tggcttcgc aacttgcatg
 2161 tggatgacca gatggcggtc attcagtatt cctggatggg actgatggta tttgccatgg
 2221 gttggcggtc cttcactaat gtcaactcca gatgctcta cttgcacct gacttggttt
 2281 tcaatgagta ccgcatgcac aagtctcgga tgtacagcca gtgtgtgagg atgaggcacc
 2341 tgtctcaaga gtttggatgg ctccaaataa ccccccagga attcctgtgc atgaaagcac
 2401 tgctgctctt cagcattatt ccagtggatg ggctgaaaaa tcaaaaattc tttgatgaac
 2461 ttcgaatgaa ctacatcaag gaactcgatc gcatcattgc atgcaaaaga aagaatccca
 2521 catctgctc aaggcgcttc taccagctca ccaagctcct ggattctgtg cagcctattg
 2581 caagagagct gcatcagttc acttttgacc tgctaatcaa gtccatatg tgagcgtgg
 2641 actttcctga aatgatggca gagatcatct ctgtgcaagt gcccaagatc ctttctggga
 2701 aagtcaagcc catctatttc cacacacagt gaagatttgg aaacctaat accaaaacc
 2761 caccttgttc cctttccaga tgtcttctgc ctgttatata actctgcact actttctgc
 2821 agtgccttgg gggaaattcc tctactgatg tacagtctgt cgtgaacagg ttcctcagtt
 2881 ctatttcctg ggcttctcct tcttttttt tcttcttccc tccctcttc acctccat
 2941 ggcacatttt gaatctgctg cgtattgtgg ctcctgcctt tgttttgatt tctgttgta
//
```

Figure 7

SEQ ID NO: 82

```
LOCUS       NM_001032911            3175 bp    mRNA
DEFINITION  Macaca mulatta androgen receptor (AR), mRNA.
ACCESSION   NM_001032911
VERSION     NM_001032911.1  GI:74136372
SOURCE      Macaca mulatta (rhesus monkey)

ORIGIN
        1 cccaaaaaat aaaaacaaac aaaaacaaaa caaaacaaaa aaaacgaata aagaaaaagg
       61 taataactca gttcttattt gcacctactt ccagtggaca ctgaatttgg aaggtggagg
      121 attcttgttt ttcttttaa gatcgggcat cttttgaatc taccoctcaa gtgttaagag
      181 acagactgtg agcctagcag ggcagatctt gtccaccgtg tgtcttcttt tgcaggagac
      241 tttgagcctg tcagagcgct ttttgcgtgg ttgctcccgc aagtttcctt ctctggagct
      301 tcccgcaggt gggcagctag ctgcagcgac taccgcatca tcacagcctg ttgaactctt
      361 ctgagcaaga gaaggggagg cggggtaagg gaagtaggtg gaagattcag ccaagccaa
      421 ggatggaggt gcagttaggg ctggggaggg tctaccctcg gccgccgtcc aagacctacc
      481 gaggagcttt ccagaatctg ttccagagcg tgcgcgaagt gatccagaac ccgggcccca
      541 ggcacccaga ggccgcgagc gcagcacctc ccggcgccag tttgcagcag cagcagcagc
      601 agcagcaaga aactagcccc cggcaacagc agcagcagca gcagggtgag gatggttctc
      661 cccaagccca tcgtagaggc cccacaggct acctggtcct ggatgaggaa cagcagcctt
      721 cacagcctca gtcagcccg gagtgccacc ccgagagagg ttgcgtccca gagcctggag
      781 ccgccgtggc cgcgggcaag gggctgccgc agcagctgcc agcacctccg gacgaggatg
      841 actcagctgc cccatccacg ttgtctctgc tgggcccac tttcccggc ttaagcagct
      901 gctccgccga ccttaaagac atcctgagcg aggccagcac catgcaactc cttcagcaac
      961 agcagcagga agcagtatcc gaaggcagca gcagcgggag agcgagggag gcctcggggg
     1021 ctcccactto ctccaaggac aattacttag agggcacttg gaccatttct gacagcgcca
     1081 aggagctgtg taaggcagtg taggcttggg tgtggaggcg ttggagcatc
     1141 tgagtccagg ggaacagctt cgggggatt gcatgtacgc cccagttttg ggagttccac
     1201 ccgctgtgcg tcccactccg tgtgccccat tggccgaatg caaagttct ctgctagacg
     1261 acagcgcagg caagagcact gaagatactg ctgagtattc ccctttcaag ggaggttaca
     1321 ccaaagggct agaaggcgag agcctaggct gctctggcag cgctgcagca gggagctccg
     1381 ggacacttga actgccgtcc acctgtctc tctacaagtc cggagcactg gacgaggcag
     1441 ctgcgtacca gagtcgcgac tactacaact tccactggc tctggccggg ccgccgcccc
     1501 ctccaccgcc tccccatccc cacgctgca tcaagctga gaacccgctg gactatgca
     1561 gcgcctgggc ggctgcggcg gcgcagtgcc gctatgggga cctggcgagc ctgcatggcg
     1621 cgggtgcgcg ggggccggc tctgttccta ccttcctca tectggcaca
     1681 ctctcttcac agccgaagaa ggcagttgt atggaccgtg tggtggtgg ggcggcggcg
     1741 gtggcggcgg cggcggcgc gcaggcgagg cgggagctgt agcccctac ggctacactc
     1801 ggccacctca ggggctggcg ggccaggaag gcgacttcac cgcacctgat gtgtggtacc
     1861 ctggcggcat ggtgagcaga gtgcctatc ccagtcccac ttgtgtcaaa agcgagatgg
     1921 gccctgat ggatagctac tccggacctt acggggacat gcgtttggag actgccaggg
     1981 accatgtttt gccaattgac tattactttc caccccagaa gacctgctg atctgtggag
     2041 atgaagcttc tgggtgtcac tatggagcte tcacatgtgg aagctgcaag gtcttcttca
     2101 aaagagcgc tgaagggaaa cagaagtacc tgtgtgccag cagaaatgat tgcactattg
     2161 ataaattccg aaggaaaaat tgtcatcttt gcgcatcaca gaaatgttat gaagcaggga
     2221 tgactctggg agcccggaag ctgaagaaac ttggtaatct gaaactacag aggaaggag
     2281 aggcttccag caccaccagc cccactgagg agacagcca gaagctgaca gtgtcacaca
     2341 ttgaaggcta tgaatgtcag cccatctttc tgaatgtcct ggaggccatt gagccaggtg
     2401 tggtgtgtgc tggacatgac aacaaccage ccgactcctt cgcagccttg ctctctagcc
     2461 tcaatgaact gggagagaga cagcttgtac atgtggtcaa gtgggccaag gccttgcctg
     2521 gcttccgcaa cttacacgtg gacgaccaga tggctgtcat tcagtactcc tggatgggc
     2581 tcatggtgtt tgccatgggc tggcgatcct tcaccaatgt caactccagg atgctctact
     2641 ttgcccctga tctggttttc aatgagtacc gcatgcacaa atcccggatg tacagccagt
     2701 gtgtgcgaat gaggcacctc tctcaaagt ttggatggc ccaaatcacc cccaggaat
     2761 tcctgtgcat gaaagcgctg ctactcttca gcattattcc gcattcacc agtggatggg ctgaaaaatc
     2821 aaaaattctt tgatgaactt cgaatgaact acatcaagga actcgatcgt atcattgcat
     2881 gcaaaagaaa aaatcccaca tcctgtcaa ggcgtttcta ccagtcacc aagctcctgg
     2941 actccgtgca gcctattgcg agagagctgc atcagttcac ttttgacctg ctaatcaagt
     3001 cacacatggt gagcgtggac tttccggaaa tgatggcaga gatcatctct gtgcaagtgc
     3061 ccaagatcct ttctgggaaa gtcaagccca tctattcca cacccagtga agcattggaa
     3121 atccctactt cctcaccca gctcatgccc ctttcagat gtcttctgcc tgtta
//
```

Figure 8

SEQ ID NO:83

```
LOCUS       NP_000035                920 aa
DEFINITION  androgen receptor isoform 1 [Homo sapiens].
ACCESSION   NP_000035
VERSION     NP_000035.2  GI:21322252
DBSOURCE    REFSEQ: accession NM_000044.2
SOURCE      Homo sapiens (human)

ORIGIN
        1 mevqlglgrv yprppsktyr gafqnlfqsv reviqnpgpr hpeaasaapp gasllllqqq
       61 qqqqqqqqqq qqqqqqqqqq etsprqqqqq qgedgspqah rrgptgylvl deeqqpsqpq
      121 salechperg cvpepgaava askglpqqlp appdeddsaa pstlsllgpt fpqlsscsad
      181 lkdilseast mqllqqqqqe avseqsssgr areasgapts skdnylqgts tisdnakelc
      241 kavsvsmglg vealehlspg eqlrgdcmya pllgvppavr ptpcaplaec kgslldddsag
      301 kstedtaeys pfkggytkgl egeslgcsgs aaagssgtle lpstlslyks galdeaaayq
      361 srdyynfpla lagppppppp phpharikle npldygsawa aaaaqcrygd laslhgagaa
      421 gpgsgspsaa asaswhtlft aceqglygpc ggggggggg ggggggggg gggeagavap
      481 ygytrppqgl aggqesdftap dvwypggmvs rvpypsptcv ksemgpwmds ysgpygdmrl
      541 etardhvlpi dyyfppqktc licgdeasgc hygaltcgsc kvffkraaeg kqkylcasrn
      601 dctidkfrrk ncpscrlrkc yeagmtlgar klkklgnikl qeegeasstt spteettqkl
      661 tvshiegyec qpiflnvlea iepgvvcagh dnnqpdsfaa llsslnelge rqlvhvvkwa
      721 kalpgfrnlh vddqmaviqy swmglmvfam gwrsftnvns rmlyfapdlv fneyrmhksr
      781 mysqcvrmrh lsqefgwlqi tpqeflcmka lllfsiipvd glknqkffde lrmnyikeld
      841 riiackrknp tscsrrfyql tklldsvqpi arelhqftfd llikshmvsv dfpemmaeii
      901 svqvpkilsg kvkpiyfhtq
//
```

Figure 9

SEQ ID NO:84

```
LOCUS       NP_038504                899 aa
DEFINITION  androgen receptor [Mus musculus].
ACCESSION   NP_038504
VERSION     NP_038504.1  GI:7304901
DBSOURCE    REFSEQ: accession NM_013476.3
SOURCE      Mus musculus (house mouse)

ORIGIN
        1 mevqlglgrv yprppsktyr gafqnlfqsv reaiqnpgpr hpeaaniapp gaclqqrqet
       61 sprrrrqqh tedgspqahi rgptgylale eeqqpsqqqa aseghpessc lpepgaatap
      121 gkglpqqppa ppdqddsaap stlsllgptf pglsscsadi kdilneagtm qllqqqqqqq
      181 qhqqqhgqhq qqqeviseqs sararreatga psskdsylg gnstisdsak eickavsvsm
      241 glgvealehl spgeqlrgdc myaspllggpp avrptpcapl peckglplde gpgksteeta
      301 eyssfkggya kglegeslgc sgsseagssg tleipsslsl yksgaldeaa ayqnrdyynf
      361 plaisgpphp pppthphari klenpldygs awaaaaaqcr ygdlgslhgg svaqpstgsp
      421 pattssswht lftaeegqly gpggggggsss psdagpvapy gytrppqglt sqesdysase
      481 vwypggvvnr vpypspncvk semgpwmeny sgpygdmrld strdhvlpid yyfppqktcl
      541 icgdeasgch ygaltcgsck vffkraaegk qkylcasrnd ctidkfrrkn cpscrirkcy
      601 eagmtlgark lkklgnlklq eegensnags ptedpsqkmt vshiegyecq piflnvleai
      661 epgvvcaghd nnqpdsfaal lsslnelger qlvhvvkwak alpgfrnlhv ddqmaviqys
      721 wmglmvfamg wrsftnvnsr mlyfapdlvf neyrmhksrm ysqcvrmrhl sqefgwlqit
      781 pqeflcmkal llfsiipvdg lknqkffdel rmnyikeldr iiackrknpt scsrrfyqlt
      841 klldsvqpia relhqftfdl likshmvsvd fpemmaeiis vqvpkilsgk vkpiyfhtq
//
```

Figure 10

```
SEQ ID NO:85
LOCUS       NP_001028083             895 aa
DEFINITION  androgen receptor [Macaca mulatta].
ACCESSION   NP_001028083
VERSION     NP_001028083.1  GI:74136373
DBSOURCE    REFSEQ: accession NM_001032911.1
SOURCE      Macaca mulatta (rhesus monkey)

ORIGIN
        1 mevqlglgrv yprppsktyr gafqnlfqsv reviqnpgpr hpeaasaapp qaslqqqqqq
       61 qqetsprqqq qqqqgedgsp qahrrgptgy lvldeeqqps qpqsapechp ergcvpepga
      121 avaagkglpq qlpappdedd saapstlsll gptfpglssc sadlkdilse astmqllqqq
      181 qqeavsegss sgrareasga ptssakdnyle gtstisdsak elckavsvsm glgvealehl
      241 spgeqlrgdc myapvlgvpp avrptpcapl aeckgsildd sagkstedta eyspfkggyt
      301 kglegeslgc sgsaaagssg tlelpstlsl yksgaldeaa ayqsrdyynf plalagpppp
      361 pppphphari klenpldygs awaaaaaqcr ygdlaslhga gaagpgsgsp saaassswht
      421 lftaeegqly gpcgggggg gggggagea gavapygytr ppqglagqeg dftapdvwyp
      481 ggmvsrvpyp sptcvksemg pwmdsysgpy gdmrletard hvlpidyyfp pqktclicgd
      541 easgchygal tegsckvffk raaegkqkyl casrndctid kfrrkncpsc rlrkcyeagm
      601 tlgarklkkl gnlkleeege assttsptee taqkltvshi egyecqpifl nvlealepgv
      661 vcaghdnnqp dsfaallssl nelgerqlvh vvkwakalpg frnlhvddqm avlqyswmgl
      721 mvfamgwrsf tnvnsrmlyf apdlvfneyr mhksrmysgc vrmrhlsqef gwlqitpqef
      781 lcmkallllfs iipvdglknq kffdelrmny ikeldriiac krknptscsr rfyqltklld
      841 svqpiarelh qftfdlliks hmvsvdfpem maeiisvqvp kilsgkvkpi yfhtq
//
```

LNA ANTAGONISTS TARGETING THE ANDROGEN RECEPTOR

This application is a continuation application of U.S. application Ser. No. 12/322,033 filed on Nov. 26, 2008, which claims the benefit under 35 U.S.C. §119(e) of U.S. Provisional Application Ser. No. 60/990,125 filed Nov. 26, 2007, the disclosure of each of which is incorporated herein by reference in its entirety.

FIELD OF INVENTION

The invention provides compounds, compositions and methods for modulating the expression of the androgen receptor. In particular, this invention relates to oligomeric compounds (oligomers), which target the androgen receptor mRNA in a cell, leading to reduced expression of the androgen receptor. Reduction of androgen receptor expression is beneficial for a range of medical disorders, such as cancer, particularly prostate cancer or breast cancer.

BACKGROUND

The androgen receptor ("AR") is a type of nuclear receptor which is activated by binding of either of the androgenic hormones testosterone or dihydrotestosterone. The main function of the androgen receptor is as a DNA binding transcription factor which regulates gene expression. However the androgen receptor also has additional functions independent of DNA binding. The androgen receptor is most closely related to the progesterone receptor, and progestins in higher dosages can block the androgen receptor.

Whilst in humans the AR gene is single copy and found on the X chromosome at position Xq11-12, the receptor itself exists in two iso-forms (A and B). AR-A is an 87 kDa protein which lacks the first 187 amino acids (N-terminal truncation). Isoform AR-B is the full length 110 kDa version.

The binding of an androgen to the androgen receptor induces a conformational change in the receptor, resulting in a dissociation of heat shock proteins, dimerization and transport from the cytosol to the cell nucleus where the androgen receptor dimer binds to specific DNA sequences—referred to as hormone response elements. Depending on the interaction with other nuclear proteins, the AR controls gene expression, either increasing or decreasing transcription of specific genes, such as insulin-like growth factor I (IGF-1).

Androgen receptors can also have cytoplasmic activities through interaction with signal transduction proteins in the cytoplasm. Androgen binding to cytoplasmic androgen receptors can cause rapid changes in cell function independent of gene transcription, for example ion transport, as well as indirect influence of gene transcription, for example via mediating other signal transduction pathways, thereby influencing the activity of other transcription factors.

The over-expression of androgen receptor, or expression of mutated androgen receptor genes, has been indicated in several diseases, such as cancer, including prostate cancer and breast cancer, as well as other disorders such as polyglutamate disease (Monks et al., PNAS Nov. 2, 2007, published on line) alopecia, benign prostatic hyperplasia, spinal and muscular atrophy and Kennedy disease.

WO97/11170 describes a method of treating a patient diagnosed as having benign prostatic hyperplasia or a prostate cancer comprising administering an antisense oligonucleotide which selectively hybridises to the androgen receptor mRNA. Three antisense oligonucleotide sequences of between 27-29 nucleotides are disclosed.

U.S. Pat. No. 6,733,776 and EP 0 692 972 describe a method for treating androgenic alopecia by applying liposomes comprising an antisense nucleic acid that hybridises to an androgen receptor gene. No antisense molecules having specific sequences and targeting the androgen receptor are provided.

US 2005/0164970 describes a method of treating prostate cancer using siRNA complexes targeting the androgen receptor mRNA.

WO 2005/027833 describes a method of treating prostate cancer comprising administering to a patient an oligonucleotide comprising between 12-40 morpholino sub-units.

WO 2001/083740 describes an antisense compound having an uncharged morpholino backbone of between 18 to 20 contiguous units which targets the human androgen receptor. Morpholino antisense compounds work via binding to the nucleic acid target to block access to the mRNA by other molecules, such as molecules involved in mRNA splicing or translation initiation.

U.S. Pat. No. 7,067,256 describes a ribozyme which apparently mediates inactivation of the androgen receptor. A 19-nucleotide RNA antisense molecule targeted to a region of the androgen receptor mRNA is provided.

However, despite the application of siRNA, morpholino-containing antisense oligonucleotides and ribozymes, none of the above androgen receptor inhibitors have been successful in efficiently down-regulating the androgen-receptor in vivo and at pharmacologically acceptable dosages.

The invention provides a new class of androgen receptor antagonists which contain locked nucleic acid ("LNA") monomers, and are targeted to particularly effective target sites on the androgen receptor mRNA.

SUMMARY OF INVENTION

The invention provides an oligomer of from 10-50 monomers, such as 10-30 monomers which comprises a first region of 10-50 monomers, such as 10-30 monomers, wherein the sequence of the first region is at least 80% (e.g., 85%, 90%, 95%, 98%, or 99%) identical to the reverse complement of a target region of a nucleic acid which encodes a mammalian androgen receptor, such as a mammalian androgen receptor gene or mRNA, such as a nucleic acid having the sequence set forth in SEQ ID NO: 1, or naturally occurring variants thereof. Thus, for example, the oligomer hybridizes to a region of a single-stranded nucleic acid molecule having the sequence shown in SEQ NO: 1.

The invention provides for a conjugate comprising the oligomer according to the invention, and at least one non-nucleotide or non-polynucleotide moiety covalently attached to the oligomer.

The invention provides for a pharmaceutical composition comprising the oligomer or the conjugate according to the invention, and a pharmaceutically acceptable diluent, carrier, salt or adjuvant.

The invention provides for the oligomer or the conjugate according to the invention, for use as a medicament, such as for the treatment of a disease or a medical disorder as disclosed herein, such as a hyperproliferative disorder, such as cancer or other hyperproliferative disorder. The invention provides for the use of an oligomer or the conjugate according to the invention, for the manufacture of a medicament for the treatment of a disease or disorder as disclosed herein, such as a hyperproliferative disorder, such as cancer.

The invention provides for a method of treating a disease or disorder as disclosed herein, such as a hyperproliferative disorder, such as cancer, the method comprising administering an oligomer, a conjugate or a pharmaceutical composition according to the invention to a patient suffering from or susceptible to the disease or disorder.

The invention provides for a method for the inhibition of androgen receptor in a cell which is expressing androgen receptor, the method comprising administering an oligomer, or a conjugate according to the invention to the cell so as to effect the inhibition of androgen receptor expression in said cell.

The invention provides an oligomer of from 10-50 monomers, which comprises a first region of 10-50 contiguous monomers, wherein the base sequence is at least 80% identical to the reverse complement of a target region of a nucleic acid which encodes a mammalian androgen receptor.

The invention further provides a conjugate comprising the oligomer according to the invention, which comprises at least one non-nucleotide or non-polynucleotide moiety ("conjugated moiety") covalently attached to the oligomer of the invention.

The invention provides for pharmaceutical compositions comprising an oligomer or conjugate of the invention, and a pharmaceutically acceptable diluent, carrier, salt or adjuvant.

The invention further provides for an oligomer according to the invention, for use in medicine.

The invention further provides for the use of the oligomer of the invention for the manufacture of a medicament for the treatment of one or more of the diseases referred to herein, such as a disease selected from the group consisting of cancer, such as breast cancer or prostate cancer, alopecia, benign prostatic hyperplasia, spinal and muscular atrophy, Kennedy disease and polyglutamate disease.

The invention further provides for an oligomer according to the invention, for use for the treatment of one or more of the diseases referred to herein, such as a disease selected from the group consisting of cancer, such as breast cancer or prostate cancer, alopecia, benign prostatic hyperplasia, spinal and muscular atrophy, Kennedy disease and polyglutamate disease.

Pharmaceutical and other compositions comprising an oligomer of the invention are also provided. Further provided are methods of down-regulating the expression of AR in cells or tissues comprising contacting said cells or tissues, in vitro or in vivo, with one or more of the oligomers, conjugates or compositions of the invention.

Also disclosed are methods of treating a non-human animal or a human suspected of having, or susceptible to, a disease or condition, associated with expression, or over-expression of AR by administering to the animal or human a therapeutically or prophylactically effective amount of one or more of the oligomers, conjugates or pharmaceutical compositions of the invention. Further, methods of using oligomers for the inhibition of expression of AR, and for treatment of diseases associated with activity of AR are provided.

The invention provides for a method for treating a disease selected from the group consisting of: cancer, such as breast cancer or prostate cancer, alopecia, benign prostatic hyperplasia, spinal and muscular atrophy, Kennedy disease and polyglutamate disease, the method comprising administering an effective amount of one or more oligomers, conjugates, or pharmaceutical compositions thereof to a patient in need thereof.

The invention provides for methods of inhibiting (e.g., by down-regulating) the expression of AR in a cell or a tissue, the method comprising the step of contacting the cell or tissue with an effective amount of one or more oligomers, conjugates, or pharmaceutical compositions thereof, to effect down-regulation of expression of AR.

BRIEF DESCRIPTION OF FIGURES

FIG. 3. Sequence alignment of the human Androgen receptor mRNA sequence (GenBank Accession No.: NM_000044) and the mouse Androgen receptor mRNA sequence (GenBank Accession No.: NM_013476).

FIG. 4. Location of presently preferred target regions of the human AR mRNA (cDNA) targeted by oligomers according to the invention. Although 16mer target sites have been shown, in some embodiments these target regions comprise an additional 4 monomers 5' or 3' to the target regions shown—i.e. are target regions comprising up to 24 contiguous monomers.

FIG. 5. SEQ ID NO: 1 *Homo sapiens* androgen receptor (dihydrotestosterone receptor; testicular feminization; spinal and bulbar muscular atrophy; Kennedy disease) (AR), transcript variant 1, mRNA. (GenBank Accession number: NM_000044).

FIG. 6. SEQ ID NO 81: Mouse androgen receptor mRNA sequence.

FIG. 7. SEQ ID NO 82: Rhesus monkey androgen receptor mRNA sequence.

FIG. 8. SEQ ID NO 83: *Homo sapiens* androgen receptor protein amino acid sequence.

FIG. 9. SEQ ID NO 84: Mouse androgen receptor protein amino acid sequence.

FIG. 10. SEQ ID NO 85: Rhesus monkey androgen receptor protein amino acid sequence.

DETAILED DESCRIPTION OF INVENTION

The Oligomer

Figure 1:
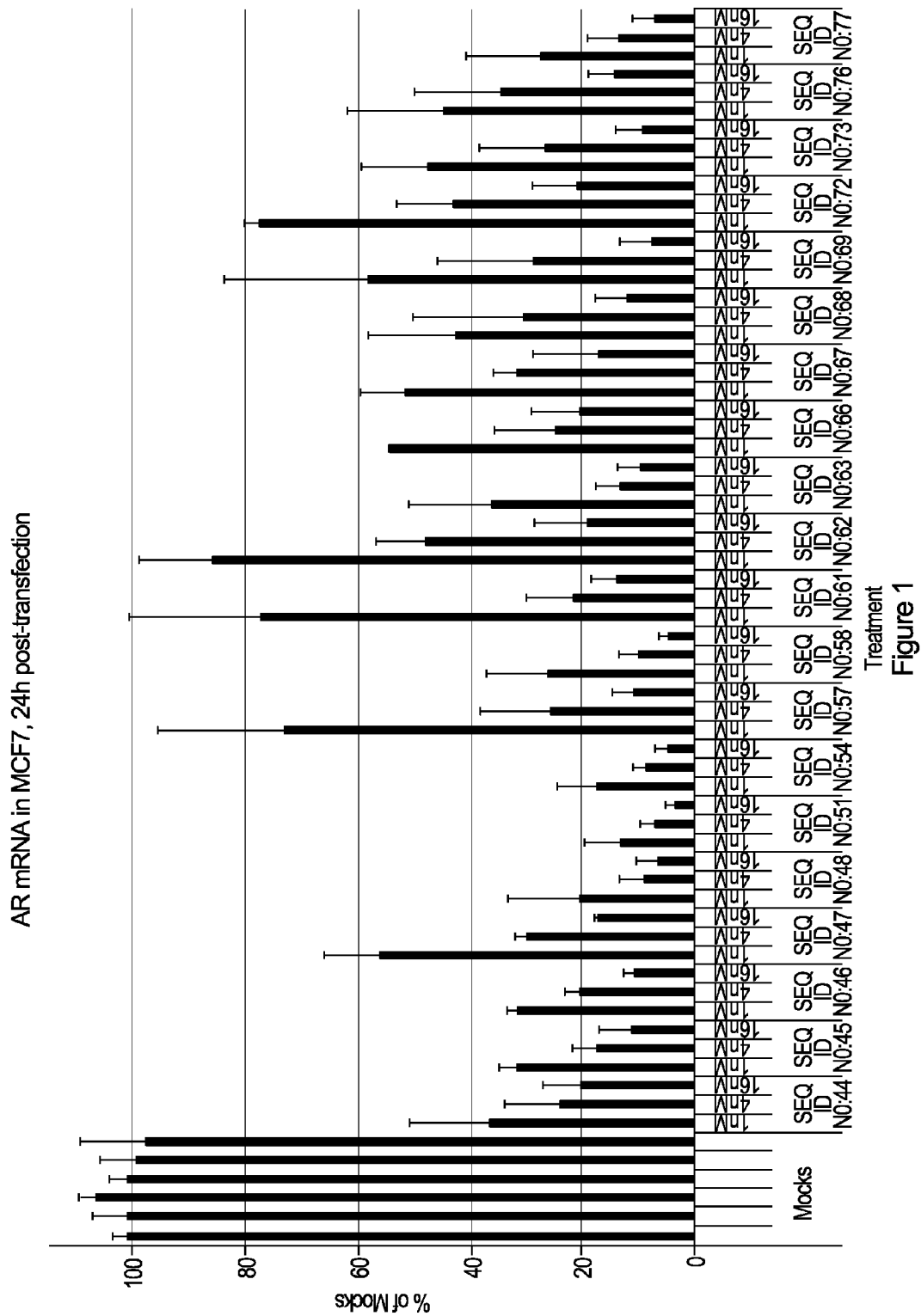
FIG. 1. Oligonucleotides presented in Table 3 were evaluated for their potential to knockdown the androgen receptor mRNA at concentrations of 1, 4 and 16 nM in MCF7 cells 24 hours after transfection using Real-time PCR. All results were normalised to GAPDH and inhibition of AR mRNA is shown as percent of untreated control. Results shown are an average of three independent experiments.

The invention employs oligomeric compounds (referred herein as oligomers), for use in modulating the function of nucleic acid molecules encoding mammalian androgen receptor, such as the androgen receptor nucleic acid shown in SEQ ID NO: 1, and naturally occurring variants of such nucleic acid molecules encoding mammalian androgen receptor. The term "oligomer" in the context of the invention, refers to a molecule formed by covalent linkage of two or more monomers (i.e. an oligonucleotide). In some embodiments, the oligomer comprises or consists of from 10-30 covalently linked monomers.

The term "monomer" includes both nucleosides and deoxynucleosides (collectively, "nucleosides") that occur naturally in nucleic acids and that do not contain either modified sugars or modified nucleobases, i.e., compounds in which a ribose sugar or deoxyribose sugar is covalently bonded to a naturally-occurring, unmodified nucleobase (base) moiety (i.e., the purine and pyrimidine heterocycles adenine, guanine, cytosine, thymine or uracil) and "nucleoside analogues," which are nucleosides that either do occur naturally in nucleic acids or do not occur naturally in nucleic acids, wherein either the sugar moiety is other than a ribose or a deoxyribose sugar (such as bicyclic sugars or 2' modified sugars, such as 2' substituted sugars), or the base moiety is modified (e.g., 5-methylcytosine), or both.

An "RNA monomer" is a nucleoside containing a ribose sugar and an unmodified nucleobase.

A "DNA monomer" is a nucleoside containing a deoxyribose sugar and an unmodified nucleobase.

A "Locked Nucleic Acid monomer," "locked monomer," or "LNA monomer" is a nucleoside analogue having a bicyclic sugar, as further described herein below.

The terms "corresponding nucleoside analogue" and "corresponding nucleoside" indicate that the base moiety in the nucleoside analogue and the base moiety in the nucleoside are identical. For example, when the "nucleoside" contains a 2-deoxyribose sugar linked to an adenine, the "corresponding nucleoside analogue" contains, for example, a modified sugar linked to an adenine base moiety.

The terms "oligomer," "oligomeric compound," and "oligonucleotide" are used interchangeably in the context of the invention, and refer to a molecule formed by covalent linkage of two or more contiguous monomers by, for example, a phosphate group (forming a phosphodiester linkage between nucleosides) or a phosphorothioate group (forming a phosphorothioate linkage between nucleosides). The oligomer consists of, or comprises, 10-50 monomers, such as 10-30 monomers.

In some embodiments, an oligomer comprises nucleosides, or nucleoside analogues, or mixtures thereof as referred to herein. An "LNA oligomer" or "LNA oligonucleotide" refers to an oligonucleotide containing one or more LNA monomers.

Nucleoside analogues that are optionally included within oligomers may function similarly to corresponding nucleosides, or may have specific improved functions. Oligomers wherein some or all of the monomers are nucleoside analogues are often preferred over native forms because of several desirable properties of such oligomers, such as the ability to penetrate a cell membrane, good resistance to extra- and/or intracellular nucleases and high affinity and specificity for the nucleic acid target. LNA monomers are particularly preferred, for example, for conferring several of the above-mentioned properties.

In various embodiments, one or more nucleoside analogues present within the oligomer are "silent" or "equivalent" in function to the corresponding natural nucleoside, i.e., have no functional effect on the way the oligomer functions to inhibit target gene expression. Such "equivalent" nucleoside analogues are nevertheless useful if, for example, they are easier or cheaper to manufacture, or are more stable under storage or manufacturing conditions, or can incorporate a tag or label. Typically, however, the analogues will have a functional effect on the way in which the oligomer functions to inhibit expression; for example, by producing increased binding affinity to the target region of the target nucleic acid and/or increased resistance to intracellular nucleases and/or increased ease of transport into the cell.

Thus, in various embodiments, oligomers according to the invention comprise nucleoside monomers and at least one nucleoside analogue monomer, such as an LNA monomer, or other nucleoside analogue monomers.

The term "at least one" comprises the integers larger than or equal to 1, such as 1, 2, 3, 4, 5, 6, 7, 8, 9, 10, 11, 12, 13, 14, 15, 16, 17, 18, 19, 20 and so forth. In various embodiments, such as when referring to the nucleic acid or protein targets of the compounds of the invention, the term "at least one" includes the terms "at least two" and "at least three" and "at least four." Likewise, in some embodiments, the term "at least two" comprises the terms "at least three" and "at least four."

In some embodiments, the oligomer comprises or consists of 10, 11, 12, 13, 14, 15, 16, 17, 18, 19, 20, 21, 22, 23, 24, 25, 26, 27, 28, 29 or 30 contiguous monomers.

In some embodiments, the oligomer comprises or consists of 10-22 contiguous monomers, such as 12-18 contiguous monomers, such as 13-17 or 12-16 contiguous monomers, such as 13, 14, 15, 16 contiguous monomers.

In certain embodiments, the oligomer comprises or consists of 10, 11, 12, 13, or 14 contiguous monomers.

In various embodiments, the oligomer according to the invention consists of no more than 22 monomers, such as no more than 20 monomers, such as no more than 18 monomers, such as 15, 16 or 17 monomers. In some embodiments, the oligomer of the invention comprises less than 20 monomers.

In various embodiments, the compounds of the invention do not comprise RNA monomers.

In various embodiments, the compounds according to the invention are linear molecules or are linear as synthesised. The oligomer, in such embodiments, is a single stranded molecule, and typically does not comprise short regions of, for example, at least 3, 4 or 5 contiguous monomers, which are complementary to another region within the same oligomer such that the oligomer forms an internal duplex. In some embodiments, the oligomer is essentially not double stranded, i.e., is not a siRNA.

In some embodiments, the oligomer of the invention consists of a contiguous stretch of monomers, the sequence of which is identified by a SEQ ID NO disclosed herein (see, e.g., Tables 1-3). In other embodiments, the oligomer comprises a first region, the region consisting of a contiguous stretch of monomers, and one or more additional regions which consist of at least one additional monomer. In some embodiments, the sequence of the first region is identified by a SEQ ID NO disclosed herein.

Gapmer Design

Typically, the oligomer of the invention is a gapmer.

A "gapmer" is an oligomer which comprises a contiguous stretch of monomers capable of recruiting an RNAse (e.g., such as RNAseH) as further described herein below, such as a region of at least 6 or 7 DNA monomers, referred to herein as region B, wherein region B is flanked both on its 5' and 3' ends by regions respectively referred to as regions A and C, each of regions A and C comprising or consisting of nucleoside analogues, such as affinity-enhancing nucleoside analogues, such as 1-6 nucleoside analogues.

Typically, the gapmer comprises regions, from 5' to 3', A-B-C, or optionally A-B-C-D or D-A-B-C, wherein: region A consists of or comprises at least one nucleoside analogue, such as at least one LNA monomer, such as 1-6 nucleoside analogues, such as LNA monomers, and region B consists of or comprises at least five contiguous monomers which are capable of recruiting RNAse (when formed in a duplex with a complementary target region of the target RNA molecule, such as the mRNA target), such as DNA monomers; region C consists of or comprises at least one nucleoside analogue, such as at least one LNA monomer, such as 1-6 nucleoside analogues, such as LNA monomers; and region D, when present, consists of or comprises 1, 2 or 3 monomers, such as DNA monomers.

In various embodiments, region A consists of 1, 2, 3, 4, 5 or 6 nucleoside analogues, such as LNA monomers, such as 2-5 nucleoside analogues, such as 2-5 LNA monomers, such as 3 or 4 nucleoside analogues, such as 3 or 4 LNA monomers; and/or region C consists of 1, 2, 3, 4, 5 or 6 nucleoside analogues, such as LNA monomers, such as 2-5 nucleoside analogues, such as 2-5 LNA monomers, such as 3 or 4 nucleoside analogues, such as 3 or 4 LNA monomers.

In certain embodiments, region B consists of or comprises 5, 6, 7, 8, 9, 10, 11 or 12 contiguous monomers which are capable of recruiting RNAse, or 6-10, or 7-9, such as 8 contiguous monomers which are capable of recruiting RNAse. In certain embodiments, region B consists of or comprises at least one DNA monomer, such as 1-12 DNA monomers, preferably 4-12 DNA monomers, more preferably 6-10 DNA monomers, such as 7-10 DNA monomers, most preferably 8, 9 or 10 DNA monomers.

In various embodiments, region A consists of 3 or 4 nucleoside analogues, such as LNA monomers, region B consists of 7, 8, 9 or 10 DNA monomers, and region C consists of 3 or 4 nucleoside analogues, such as LNA monomers. Such designs include (A-B-C) 3-10-3, 3-10-4, 4-10-3, 3-9-3, 3-9-4, 4-9-3, 3-8-3, 3-8-4, 4-8-3, 3-7-3, 3-7-4, 4-7-3, and may further include region D, which may have one or 2 monomers, such as DNA monomers.

Further gapmer designs are disclosed in WO2004/046160, which is hereby incorporated by reference.

US provisional application, 60/977,409, hereby incorporated by reference, refers to 'shortmer' gapmer oligomers. In some embodiments, oligomers presented here may be such shortmer gapmers.

In certain embodiments, the oligomer consists of 10, 11, 12, 13 or 14 contiguous monomers, wherein the regions of the oligomer have the pattern (5'-3'), A-B-C, or optionally A-B-C-D or D-A-B-C, wherein: region A consists of 1, 2 or 3 nucleoside analogue monomers, such as LNA monomers; region B consists of 7, 8 or 9 contiguous monomers which are capable of recruiting RNAse when formed in a duplex with a complementary RNA molecule (such as a mRNA target); and region C consists of 1, 2 or 3 nucleoside analogue monomers, such as LNA monomers. When present, region D consists of a single DNA monomer.

In certain embodiments, region A consists of 1 LNA monomer. In certain embodiments, region A consists of 2 LNA monomers. In certain embodiments, region A consists of 3 LNA monomers. In certain embodiments, region C consists of 1 LNA monomer. In certain embodiments, region C consists of 2 LNA monomers. In certain embodiments, region C consists of 3 LNA monomers. In certain embodiments, region B consists of 7 nucleoside monomers, In certain embodiments, region B consists of 8 nucleoside monomers. In certain embodiments, region B consists of 9 nucleoside monomers. In certain embodiments, region B comprises 1-9 DNA monomers, such as 2, 3, 4, 5, 6, 7 or 8 DNA monomers. In certain embodiments, region B consists of DNA monomers. In certain embodiments, region B comprises at least one LNA monomer which is in the alpha-L configuration, such as 2, 3, 4, 5, 6, 7, 8 or 9 LNA monomers in the alpha-L-configuration. In certain embodiments, region B comprises at least one alpha-L-oxy LNA monomer. In certain embodiments, all the LNA monomers in region B that are in the alpha-L-configuration are alpha-L-oxy LNA units. In certain embodiments, the number of monomers present in the A-B-C regions are selected from the group consisting of (nucleoside analogue monomers—region B—nucleoside analogue monomers): 1-8-1, 1-8-2, 2-8-1, 2-8-2, 3-8-3, 2-8-3, 3-8-2, 4-8-1, 4-8-2, 1-8-4, 2-8-4, or; 1-9-1, 1-9-2, 2-9-1, 2-9-2, 2-9-3, 3-9-2, 1-9-3, 3-9-1, 4-9-1, 1-9-4, or; 1-10-1, 1-10-2, 2-10-1, 2-10-2, 1-10-3, 3-10-1. In certain embodiments, the number of monomers present in the A-B-C regions of the oligomer of the invention is selected from the group consisting of: 2-7-1, 1-7-2, 2-7-2, 3-7-3, 2-7-3, 3-7-2, 3-7-4, and 4-7-3. In certain embodiments, each of regions A and C consists of two LNA monomers, and region B consists of 8 or 9 nucleoside monomers, preferably DNA monomers.

In various embodiments, other gapmer designs include those where regions A and/or C consists of 3, 4, 5 or 6 nucleoside analogue, such as monomers containing a 2'-O-methoxyethyl-ribose sugar (2'-MOE) or monomers containing a 2'-fluoro-deoxyribose sugar, and region B consists of 8, 9, 10, 11 or 12 nucleosides, such as DNA monomers, where regions A-B-C have 5-10-5 or 4-12-4 monomers. Further gapmer designs are disclosed in WO 2007/146511A2, hereby incorporated by reference.

Internucleoside Linkages

The monomers of the oligomers described herein are coupled together via linkage groups. Suitably, each monomer is linked to the 3' adjacent monomer via a linkage group.

The terms "linkage group" or "internucleoside linkage" means a group capable of covalently coupling together two contiguous monomers. Specific and preferred examples include phosphate groups (forming a phosphodiester between adjacent nucleoside monomers) and phosphorothioate groups (forming a phosphorothioate linkage between adjacent nucleoside monomers).

Suitable linkage groups include those listed in PCT/DK2006/000512, for example in the first paragraph of page 34 of PCT/DK2006/000512 (hereby incorporated by reference).

It is, in various embodiments, preferred to modify the linkage group from its normal phosphodiester to one that is more resistant to nuclease attack, such as phosphorothioate or boranophosphate—these two being cleavable by RNase H, thereby permitting RNase-mediated antisense inhibition of expression of the target gene.

In some embodiments, suitable sulphur (S) containing linkage groups as provided herein are preferred. In various embodiments, phosphorothioate linkage groups are preferred, particularly for the gap region (B) of gapmers. In certain embodiments, phosphorothioate linkages are used to link together monomers in the flanking regions (A and C). In various embodiments, phosphorothioate linkages are used for linking regions A or C to region D, and for linking together monomers within region D.

In various embodiments, regions A, B and C, comprise linkage groups other than phosphorothioate, such as phosphodiester linkages, particularly, for instance when the use of nucleoside analogues protects the linkage groups within regions A and C from endo-nuclease degradation—such as when regions A and C comprise LNA monomers.

In various embodiments, adjacent monomers of the oligomer are linked to each other by means of phosphorothioate groups.

It is recognised that the inclusion of phosphodiester linkages, such as one or two linkages, into an oligomer with a phosphorothioate backbone, particularly with phosphorothioate linkage groups between or adjacent to nucleoside analogue monomers (typically in region A and/or C), can modify the bioavailability and/or bio-distribution of an oligomer—see WO2008/053314, hereby incorporated by reference.

In some embodiments, such as the embodiments referred to above, where suitable and not specifically indicated, all remaining linkage groups are either phosphodiester or phosphorothioate, or a mixture thereof.

In some embodiments all the internucleoside linkage groups are phosphorothioate.

When referring to specific gapmer oligonucleotide sequences, such us those provided herein, it will be understood that, in various embodiments, when the linkages are phosphorothioate linkages, alternative linkages, such as those disclosed herein may be used, for example phosphate (phosphodiester) linkages may be used, particularly for linkages between nucleoside analogues, such as LNA monomers. Likewise, in various embodiments, when referring to specific gapmer oligonucleotide sequences, such as those provided herein, when one or more monomers in region C comprises a 5-methylcytosine base, other monomers in that region may contain unmodified cytosine bases.

Target Nucleic Acid

The terms "nucleic acid" and "polynucleotide" are used interchangeably herein, and are defined as a molecule formed by covalent linkage of two or more monomers, as above-described. Including 2 or more monomers, "nucleic acids" may be of any length, and the term is generic to "oligomers", which have the lengths described herein. The terms "nucleic acid" and "polynucleotide" include single-stranded, double-stranded, partially double-stranded, and circular molecules.

The term "target nucleic acid", as used herein, refers to DNA or RNA (e.g., mRNA or pre-mRNA) encoding a mammalian androgen receptor polypeptide, such as human androgen receptor, such as the nucleic acid having the sequence shown in SEQ ID NO: 1, and naturally occurring allelic variants of such nucleic acids. In certain embodiments, the mammalian androgen receptor is a mouse androgen receptor. In some embodiments, for example when used in research or diagnostics, the "target nucleic acid" is a cDNA or a synthetic oligonucleotide derived from the above DNA or RNA nucleic acid targets. The oligomers according to the invention are typically capable of hybridising to the target nucleic acid.

Exemplary target nucleic acids include mammalian androgen receptor-encoding nucleic acids having the GenBank Accession numbers shown in the table below, along with their corresponding protein sequences:

|  | GenBank Accession Number Nucleic acid (mRNA/cDNA sequence) | GenBank Accession Number Polypeptide (deduced) |
|---|---|---|
| Human | NM_000044 | NP_000035 |
| Mouse | NM_013476 | NP_038504 |
| Rhesus monkey | NM_001032911 | NP_001028083 |

It is recognised that the above-disclosed GenBank Accession numbers for nucleic acids refer to cDNA sequences and not to mRNA sequences per se. The sequence of a mature mRNA can be derived directly from the corresponding cDNA sequence with thymine bases (T) being replaced by uracil bases (U).

The term "naturally occurring variant thereof" refers to variants of the androgen receptor polypeptide or nucleic acid sequence which exist naturally within the defined taxonomic group, such as mammalian, such as mouse, monkey, and preferably human AR. Typically, when referring to "naturally occurring variants" of a polynucleotide the term also encompasses any allelic variant of the androgen receptor encoding genomic DNA which is found at the Chromosome X: 66.68-66.87 Mb by chromosomal translocation or duplication, and the RNA, such as mRNA derived therefrom. "Naturally occurring variants" may also include variants derived from alternative splicing of the androgen receptor mRNA. When referenced to a specific polypeptide sequence, e.g., the term also includes naturally occurring forms of the protein which may therefore be processed, e.g. by co- or post-translational modifications, such as signal peptide cleavage, proteolytic cleavage, glycosylation, etc.

It is recognised that the human androgen receptor gene exhibits allelic variations that are associated with disease phenotypes (Mooney et al, NAR 15; 31(8) 2003). For example, a $(CAG)_n$ repeat expansion is associated with polyglutamine expansion disorder. Other characterised allelic variants include a $(GGC)_n$ trinucleotide repeat and single nucleotide polymorphisms R726L, T887A and L710H, of which the latter two single nucleotide polymorphisms have been shown to be correlated to enhanced promiscuity of the AR receptor for other steroid ligands. In one embodiment "n" ranges from 5-31. CAG repeats of less than 22 have been associated with an enhanced risk of prostate cancer in African American males.

In various embodiments, the target nucleic acid is an AR allelic variant which comprises a $(CAG)_n$ trinucleotide repeat, or $(GGC)_n$ trinucleotide repeat. In other embodiments, the target nucleic acid is an AR allelic variant which comprises one or more single nucleotide polymorphisms, including R726L, T887A and L710H.

In certain embodiments, oligomers described herein bind to a region of the target nucleic acid (the "target region") by either Watson-Crick base pairing, Hoogsteen hydrogen bonding, or reversed Hoogsteen hydrogen bonding, between the monomers of the oligomer and monomers of the target nucleic acid. Such binding is also referred to as "hybridisation." Unless otherwise indicated, binding is by Watson-Crick pairing of complementary bases (i.e., adenine with thymine (DNA) or uracil (RNA), and guanine with cytosine), and the oligomer binds to the target region because the sequence of the oligomer is identical to, or partially-identical to, the sequence of the reverse complement of the target region; for purposes herein, the oligomer is said to be "complementary" or "partially complementary" to the target region, and the percentage of "complementarity" of the oligomer sequence to that of the target region is the percentage "identity" to the reverse complement of the sequence of the target region.

Unless otherwise made clear by context, the "target region" herein will be the region of the target nucleic acid having the sequence that best aligns with the reverse complement of the sequence of the specified oligomer (or region thereof), using the alignment program and parameters described herein below.

In determining the degree of "complementarity" between oligomers of the invention (or regions thereof) and the target region of the nucleic acid which encodes mammalian androgen receptor, such as those disclosed herein, the degree of "complementarity" (also, "homology") is expressed as the percentage identity between the sequence of the oligomer (or region thereof) and the reverse complement of the sequence of the target region that best aligns therewith. The percentage is calculated by counting the number of aligned bases that are identical as between the 2 sequences, dividing by the total number of contiguous monomers in the oligomer, and multiplying by 100. In such a comparison, if gaps exist, it is preferable that such gaps are merely mismatches rather than areas where the number of monomers within the gap differs between the oligomer of the invention and the target region.

Amino acid and polynucleotide alignments, percentage sequence identity, and degree of complementarity may be determined for purposes of the invention using the ClustalW algorithm using standard settings: see http://www.ebi.ac.uk/emboss/align/index.html, Method: EMBOSS::water (local): Gap Open=10.0, Gap extend=0.5, using Blosum 62 (protein), or DNAfull for nucleotide/nucleobase sequences.

As will be understood, depending on context, "mismatch" refers to a non-identity in sequence (as, for example, between the nucleobase sequence of an oligomer and the reverse complement of the target region to which it binds; as for example, between the base sequence of two aligned AR encoding nucleic acids), or to noncomplementarity in sequence (as, for example, between an oligomer and the target region to which it binds).

The androgen receptor is known to regulate the expression of several genes, such as a gene selected from the group consisting of Protein kinase C delta (PRKCD), Glutathione S—transferase theta 2 (GSTT2), transient receptor potential cation channel subfamily V member 3 (TRPV3), Pyrroline-5-carboxylate reductase 1 (PYCR1) and ornithine aminotransferase (OAT). Such genes regulated by AR are referred to herein as "androgen receptor (AR) target genes". In various embodiments, the oligomers according to the invention are capable of inhibiting (such as, by down-regulating) the expression of one or more AR target genes in a cell which is expressing, or is capable of expressing (i.e. by alleviating AR repression of the AR target gene in a cell) an AR target gene.

The oligomers which target the androgen receptor mRNA, may hybridize to any site along the target mRNA nucleic acid, such as the 5' untranslated leader, exons, introns and 3' untranslated tail. However, it is preferred that the oligomers which target the androgen receptor mRNA hybridise to the mature mRNA form of the target nucleic acid.

Suitably, the oligomer of the invention or conjugate thereof is capable of down-regulating expression of the androgen receptor gene. In various embodiments, the oligomer (or conjugate) of the invention can effect the inhibition of androgen receptor, typically in a mammalian cell, such as a human cell. In certain embodiments, the oligomers of the invention, or conjugates thereof, bind to the target nucleic acid and effect inhibition of AR mRNA expression of at least 10% or 20% compared to the expression level immediately prior to dosing of the oligomer, more preferably of at least 30%, 40%, 50%, 60%, 70%, 80%, 90% or 95% as compared to the AR expression level immediately prior to dosing of the oligomer. In some embodiments, such inhibition is seen when using from about 0.04 nM to about 25 nM, such as from about 0.8 nM to about 20 nM of the oligomer or conjugate.

In various embodiments, the inhibition of mRNA expression is less than 100% (i.e., less than complete inhibition of expression), such as less than 98% inhibition, less than 95% inhibition, less than 90% inhibition, less than 80% inhibition, such as less than 70% inhibition. In various embodiments, modulation of gene expression can be determined by measuring protein levels, e.g. by the methods such as SDS-PAGE followed by western blotting using suitable antibodies raised against the target protein. Alternatively, modulation of expression levels can be determined by measuring levels of mRNA, e.g. by northern blotting or quantitative RT-PCR. When measuring via mRNA levels, the level of down-regulation when using an appropriate dosage, such as from about 0.04 nM to about 25 nM, such as from about 0.8 nM to about 20 nM, is, in various embodiments, typically to a level of 10-20% of the normal levels in the absence of the compound or conjugate of the invention.

The invention therefore provides a method of down-regulating or inhibiting the expression of the androgen receptor protein and/or mRNA in a cell which is expressing the androgen receptor protein and/or mRNA, the method comprising contacting the cell with an effective amount of the oligomer or conjugate according to the invention to down-regulate or inhibit the expression of the androgen receptor protein and/or mRNA in the cell. Suitably the cell is a mammalian cell, such as a human cell. The contacting may occur, in some embodiments, in vitro. The contacting may occur, in some embodiments, in vivo.

Oligomer Sequences

In some embodiments, the oligomers of the invention have sequences that are identical to a sequence selected from the group consisting of SEQ ID NOS: 2-22. Target regions in human AR mRNA (cDNA) that bind to the oligomers having sequences as set forth in SEQ ID NOs: 2-22 are shown in FIG. 4 (bold and underlined, with the corresponding oligomer SEQ ID NOs indicated above).

Further provided are target nucleic acids (e.g., DNA or mRNA encoding AR) that contain target regions that are complementary or partially-complementary to one or more of the oligomers of the invention. In certain embodiments, the oligomers bind to variants of AR target regions, such as allelic variants (such as an AR gene present at gene locus Xq11-12). In some embodiments, a variant of an AR target region has at least 60%, more preferably at least 70%, more preferably at least 80%, more preferably at least 85%, more preferably at least 90%, more preferably at least 91%, at least 92%, at least 93%, at least 94%, at least 95% sequence identity to the target region in wild-type AR. Thus, in other embodiments, the oligomers of the invention have sequences that differ in 1, 2 or 3 bases when compared to a sequence selected from the group consisting of SEQ ID NOs: 2-22. Typically, an oligomer of the invention that binds to a variant of an AR target region is capable of inhibiting (e.g., by down-regulating) AR.

In other embodiments, oligomers of the invention are LNA oligomers, for example, those oligomers having the sequences shown in SEQ ID NOs: 44-80. In various embodiments, the oligomers of the invention are potent inhibitors of androgen receptor mRNA and protein expression. In various embodiments, oligomers of the invention are LNA oligomers having the sequences of SEQ ID NO: 58 or SEQ ID NO: 77.

In various embodiments, the oligomer comprises or consists of a region having a base sequence which is identical or partially identical to the sequence of the reverse complement of a target region in SEQ ID NO: 1. In various embodiments, the oligomer comprises or consists of a region having a sequence selected from the group consisting of SEQ ID NOS: 2-22 and 86-106.

In certain embodiments, the oligomer comprises or consists of a region having a base sequence which is fully complementary (perfectly complementary) to a target region of a nucleic acid which encodes a mammalian androgen receptor.

However, in some embodiments, the oligomer includes 1, 2, 3, or 4 (or more) mismatches as compared to the best-aligned target region of an AR target nucleic acid, and still sufficiently binds to the target region to effect inhibition of AR mRNA or protein expression. The destabilizing effect of mismatches on Watson-Crick hydrogen-bonded duplex may, for example, be compensated by increased length of the oligomer and/or an increased number of nucleoside analogues, such as LNA monomers, present within the oligomer.

In various embodiments, the oligomer base sequence comprises no more than 3, such as no more than 2 mismatches compared to the base sequence of the best-aligned target region of, for example, a target nucleic acid which encodes a mammalian androgen receptor.

In some embodiments, the oligomer base sequence comprises no more than a single mismatch when compared to the base sequence of the best-aligned target region of a nucleic acid which encodes a mammalian androgen receptor.

In various embodiments, the base sequence of the oligomer of the invention, or of a first region thereof, is preferably at least 80% identical to a base sequence selected from the group consisting of SEQ ID NOS: 2-22 and 86-106, such as at least 85%, at least 90%, at least 91%, at least 92%, at least 93%, at least 94%, at least 95%, at least 96% identical, such as 100% identical.

In certain embodiments, the base sequence of the oligomer of the invention or of a first region thereof is at least 80% identical to the base sequence of the reverse complement of a target region present in SEQ ID NO: 1, such as at least 85%, at least 90%, at least 91%, at least 92% at least 93%, at least 94%, at least 95%, at least 96% identical, at least 97% identical, at least 98% identical, at least 99% identical, such as 100% identical.

In various embodiments, the base sequence of the oligomer of the invention, or of a first region thereof, is preferably at least 80% complementary to a target region of SEQ ID NO: 1, such as at least 85%, at least 90%, at least 91%, at least 92%, at least 93%, at least 94%, at least 95%, at least 96% complementary, at least 97% complementary, at least 98% complementary, at least 99% complementary, such as 100% complementary (perfectly complementary).

In some embodiments the oligomer (or a first region thereof) has a base sequence selected from the group consisting of SEQ ID NOs: 2, 3, 4, 5, 6, 7, 8, 9, 10, 11, 12, 13, 14, 15, 16, 17, 18, 19, 20, 21, and 22, or is selected from the group consisting of at least 10 contiguous monomers of SEQ ID NOs: 2, 3, 4, 5, 6, 7, 8, 9, 10, 11, 12, 13, 14, 15, 16, 17, 18, 19, 20, 21, and 22. In other embodiments, the sequence of the oligomer of the invention or a first region thereof comprises one, two, or three base moieties that differ from those in oligomers having sequences of SEQ ID NOs: 2, 3, 4, 5, 6, 7, 8, 9, 10, 11, 12, 13, 14, 15, 16, 17, 18, 19, 20, 21, or 22, or the sequences of at least 10 contiguous monomers thereof, when optimally aligned with the selected sequence or region thereof.

In some embodiments the oligomer (or a first region thereof) has a base sequence selected from the group consisting of SEQ ID NOs: 86, 87, 88, 89, 90, 91, 92, 93, 94, 95, 96, 97, 98, 99, 100, 101, 102, 103, 104, 105 and 106, or the sequences of at least 10 contiguous monomers thereof. In other embodiments, the sequence of the oligomer (or a first region thereof) comprises one, two, or three base moieties that differ from those in oligomers having sequences of SEQ ID NOs: 86, 87, 88, 89, 90, 91, 92, 93, 94, 95, 96, 97, 98, 99, 100, 101, 102, 103, 104, 105 or 106, or the sequences of at least 10 contiguous monomers thereof, when optimally aligned with the selected sequence or region thereof.

In various embodiments, the oligomers comprise a region of 12, 13, 14, 15 or 16 contiguous monomers having a base sequence identically present in a sequence selected from the group consisting of SEQ ID No 2, 3, 4, 5, 6, 7, 8, 9, 10, 11, 12, 13, 14, 15, 16, 17, 18, 19, 20, 21, and 22. In other embodiments, the oligomers include a region which comprises one, two, or three base moieties that differ from those in oligomers having sequences of SEQ ID NOs: 2, 3, 4, 5, 6, 7, 8, 9, 10, 11, 12, 13, 14, 15, 16, 17, 18, 19, 20, 21, or 22.

In some embodiments the region consists of 11, 12, 13, 14, 15, 16, 17, 18, 19, 20, 21, 22, 23, 24, 25, 26, 27, 28, or 29 contiguous monomers, such as 12-22, such as 12-18 monomers. Suitably, in some embodiments, the region is of the same length as the oligomer of the invention.

In some embodiments the oligomer comprises additional monomers at the 5' or 3' ends, such as, independently, 1, 2, 3, 4 or 5 additional monomers at the 5' end and/or the 3' end of the oligomer, which are non-complementary to the target region. In various embodiments, the oligomer of the invention comprises a region that is complementary to the target, which is flanked 5' and/or 3' by additional monomers. In some embodiments the additional 5' or 3' monomers are nucleosides, such as DNA or RNA monomers. In various embodiments, the 5' or 3' monomers represent region D as referred to in the context of gapmer oligomers herein.

In certain embodiments, the oligomer according to the invention consists of OT comprises contiguous monomers having a nucleobase sequence according to SEQ ID NO:2, such as SEQ ID NO: 44, or according to a region of at least 10 contiguous monomers thereof, such as 11, 12, 13, 14, 15 or 16 contiguous monomers thereof.

In certain embodiments, the oligomer according to the invention consists of or comprises contiguous monomers having a nucleobase sequence according to SEQ ID No: 3, such as SEQ ID NO: 45, or according to a region of at least 10 contiguous monomers thereof, such as 11, 12, 13, 14, 15 or 16 contiguous monomers thereof.

In certain embodiments, the oligomer according to the invention consists of or comprises contiguous monomers having a nucleobase sequence according to SEQ ID NO: 4, such as SEQ ID NO: 46, or according to a region of at least 10 contiguous monomers thereof, such as 11, 12, 13, 14, 15 or 16 contiguous monomers thereof.

In certain embodiments, the oligomer according to the invention consists of or comprises contiguous monomers having a nucleobase sequence according to SEQ ID NO: 5, such as SEQ ID NO: 47, or according to a region of at least 10 contiguous monomers thereof, such as 11, 12, 13, 14, 15 or 16 contiguous monomers thereof.

In certain embodiments, the oligomer according to the invention consists of or comprises contiguous monomers having a nucleobase sequence according to SEQ ID NO: 6, such as SEQ ID NOs: 48, 49 or 50, or according to a region of at least 10 contiguous monomers thereof, such as 11, 12, 13, 14, 15 or 16 contiguous monomers thereof.

In certain embodiments, the oligomer according to the invention consists of or comprises contiguous monomers having a nucleobase sequence according to SEQ ID NO: 7, such as SEQ ID NOs: 51, 52, or 53, or according to a region of at least 10 contiguous monomers thereof, such as 11, 12, 13, 14, 15 or 16 contiguous monomers thereof.

In certain embodiments, the oligomer according to the invention consists of or comprises contiguous monomers having a nucleobase sequence according to SEQ ID NO: 8, such as SEQ ID NOs: 54, 55 or 56, or according to a region of at least 10 contiguous monomers thereof, such as 11, 12, 13, 14, 15 or 16 contiguous monomers thereof.

In certain embodiments, the oligomer according to the invention consists of or comprises contiguous monomers having a nucleobase sequence according to SEQ ID NO: 9, such as SEQ ID NO: 57, or according to a region of at least 10 contiguous monomers thereof, such as 11, 12, 13, 14, 15 or 16 contiguous monomers thereof.

In certain embodiments, the oligomer according to the invention consists of or comprises contiguous monomers having a nucleobase sequence according to SEQ ID NO: 10, such as SEQ ID NOs: 58, 59, or 60, or according to a region of at least 10 contiguous monomers thereof, such as 11, 12, 13, 14, 15 or 16 contiguous monomers thereof.

In certain embodiments, the oligomer according to the invention consists of or comprises contiguous monomers having a nucleobase sequence according to SEQ ID NO: 11, such as SEQ ID NO: 61, or according to a region of at least 10 contiguous monomers thereof, such as 11, 12, 13, 14, 15 or 16 contiguous monomers thereof.

In certain embodiments, the oligomer according to the invention consists of or comprises contiguous monomers having a nucleobase sequence according to SEQ ID NO: 12, such as SEQ ID NO: 62, or according to a region of at least 10 contiguous monomers thereof, such as 11, 12, 13, 14, 15 or 16 contiguous monomers thereof.

In certain embodiments, the oligomer according to the invention consists of or comprises contiguous monomers having a nucleobase sequence according to SEQ ID NO: 13, such as SEQ ID NOs: 63, 64 or 65, or according to a region of at least 10 contiguous monomers thereof, such as 11, 12, 13, 14, 15 or 16 contiguous monomers thereof.

In certain embodiments, the oligomer according to the invention consists of or comprises contiguous monomers having a nucleobase sequence according to SEQ ID NO: 14, such as SEQ ID NO: 66, or according to a region of at least 10 contiguous monomers thereof, such as 11, 12, 13, 14, 15 or 16 contiguous monomers thereof.

In certain embodiments, the oligomer according to the invention consists of or comprises contiguous monomers having a nucleobase sequence according to SEQ ID NO: 15, such as SEQ ID NO: 67, or according to a region of at least 10 contiguous monomers thereof, such as 11, 12, 13, 14, 15 or 16 contiguous monomers thereof.

In certain embodiments, the oligomer according to the invention consists of or comprises contiguous monomers having a nucleobase sequence according to SEQ ID NO: 16, such as SEQ ID NO: 68, or according to a region of at least 10 contiguous monomers thereof, such as 11, 12, 13, 14, 15 or 16 contiguous monomers thereof.

In certain embodiments, the oligomer according to the invention consists of or comprises contiguous monomers having a nucleobase sequence according to SEQ ID NO: 17, such as SEQ ID NOs: 69, 70 or 71, or according to a region of at least 10 contiguous monomers thereof, such as 11, 12, 13, 14, 15 or 16 contiguous monomers thereof.

In certain embodiments, the oligomer according to the invention consists of or comprises contiguous monomers having a nucleobase sequence according to SEQ ID NO: 18, such as SEQ ID NO: 72, or according to a region of at least 10 contiguous monomers thereof, such as 11, 12, 13, 14, 15 or 16 contiguous monomers thereof.

In certain embodiments, the oligomer according to the invention consists of or comprises contiguous monomers having a nucleobase sequence according to SEQ ID NO: 19, such as SEQ ID NOs: 73, 74 or 75, or according to a region of at least 10 contiguous monomers thereof, such as 11, 12, 13, 14, 15 or 16 contiguous monomers thereof.

In certain embodiments, the oligomer according to the invention consists of or comprises contiguous monomers having a nucleobase sequence according to SEQ ID NO: 20, such as SEQ ID NO: 76, or according to a region of at least 10 contiguous monomers thereof, such as 11, 12, 13, 14, 15 or 16 contiguous monomers thereof.

In certain embodiments, the oligomer according to the invention consists of or comprises contiguous monomers having a nucleobase sequence according to SEQ ID NO: 21, such as SEQ ID NOs: 77, 78 or 79, or according to a region of at least 10 contiguous monomers thereof, such as 11, 12, 13, 14, 15 or 16 contiguous monomers thereof.

In certain embodiments, the oligomer according to the invention consists of or comprises contiguous monomers having a nucleobase sequence according to SEQ ID NO: 22, such as SEQ ID NO: 80, or according to a region of at least 10 contiguous monomers thereof, such as 11, 12, 13, 14, 15 or 16 contiguous monomers thereof.

Nucleosides and Nucleoside Analogues

In various embodiments, at least one of the monomers present in the oligomer is a nucleoside analogue that contains a modified base, such as a base selected from 5-methylcytosine, isocytosine, pseudoisocytosine, 5-bromouracil, 5-propynyluracil, 6-aminopurine, 2-aminopurine, inosine, diaminopurine, 2-chloro-6-aminopurine, xanthine and hypoxanthine.

In various embodiments, at least one of the monomers present in the oligomer is a nucleoside analogue that contains a modified sugar.

In some embodiments, the linkage between at least 2 contiguous monomers of the oligomer is other than a phosphodiester linkage.

In certain embodiments, the oligomer includes at least one monomer that has a modified base, at least one monomer (which may be the same monomer) that has a modified sugar, and at least one inter-monomer linkage that is non-naturally occurring.

Specific examples of nucleoside analogues are described by e.g. Freier & Altmann; *Nucl. Acid Res.*, 1997, 25, 4429-4443 and Uhlmann; *Curr. Opinion in Drug Development*, 2000, 3(2), 293-213, and in Scheme 1 (in which some nucleoside analogues are shown as nucleotides):

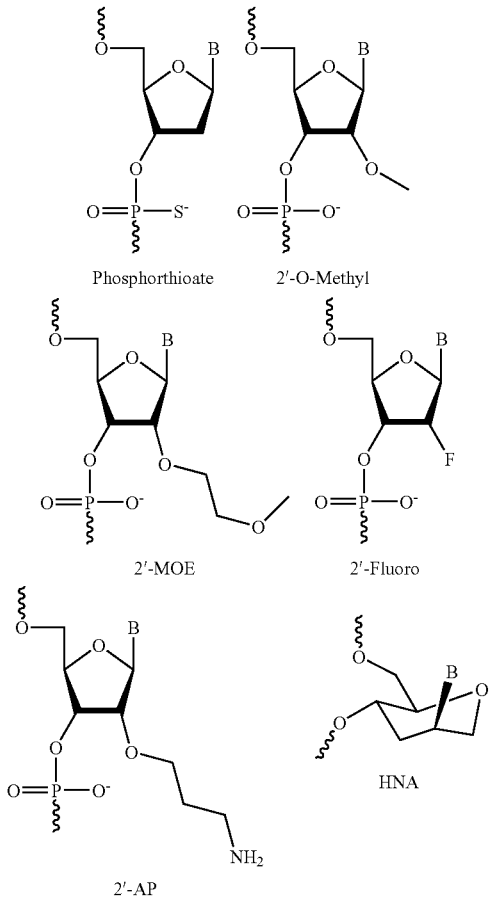

Scheme 1

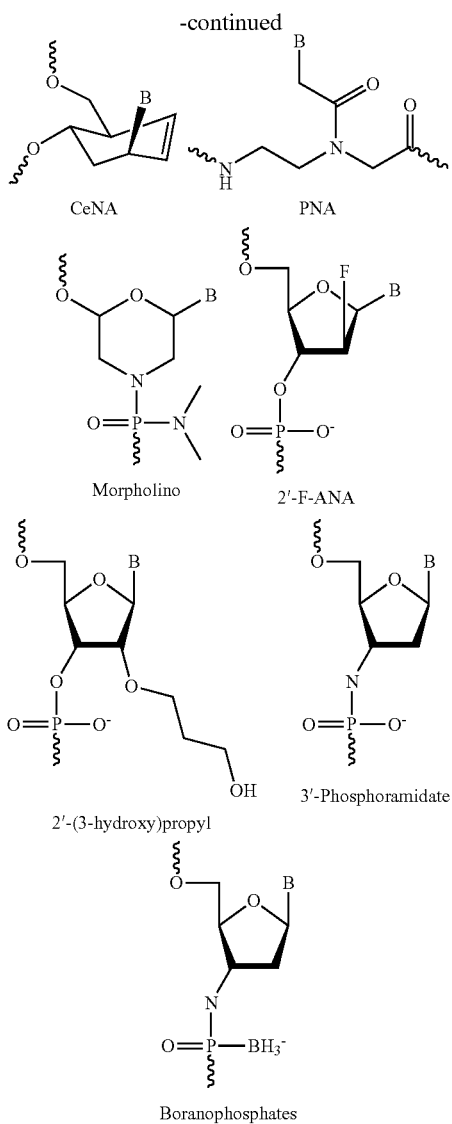

CeNA    PNA
Morpholino    2'-F-ANA
2'-(3-hydroxy)propyl    3'-Phosphoramidate
Boranophosphates The oligomer may thus comprise or consist of a simple sequence of naturally occurring nucleosides—preferably DNA monomers, but also possibly RNA monomers, or a combination of nucleosides and one or more nucleoside analogues. In some embodiments, such nucleoside analogues suitably enhance the affinity of the oligomer for the target region of the target nucleic acid.

Examples of suitable and preferred nucleoside analogues are described in PCT/DK2006/000512, or are referenced therein.

In some embodiments, the nucleoside analogue comprises a sugar moiety modified to provide a 2'-substituent group, such as 2'-O-alkyl-ribose sugars, 2'-amino-deoxyribose sugars, and 2'-fluoro-deoxyribose sugars.

In some embodiments, the nucleoside analogue comprises a sugar in which a bridged structure, creating a bicyclic sugar (LNA), which enhances binding affinity and may also provide some increased nuclease resistance. In various embodiments, the LNA monomer is selected from oxy-LNA (such as beta-D-oxy-LNA, and alpha-L-oxy-LNA), and/or amino-LNA (such as beta-D-amino-LNA and alpha-L-amino-LNA) and/or thio-LNA (such us beta-D-thio-LNA and alpha-L-thio-LNA) and/or ENA (such as beta-D-ENA and alpha-L-ENA).

In certain embodiments, the LNA monomers are beta-D-oxy-LNA. LNA monomers are further described below.

In various embodiments, incorporation of affinity-enhancing nucleoside analogues in the oligomer, such as LNA monomers or monomers containing 2'-substituted sugars, or incorporation of modified linkage groups provides increased nuclease resistance. In various embodiments, incorporation of affinity-enhancing nucleoside analogues allows the size of the oligomer to be reduced, and also reduces the size of the oligomer that binds specifically to a target region of a target sequence.

In some embodiments, the oligomer comprises at least 2 nucleoside analogues. In some embodiments, the oligomer comprises from 3-8 nucleoside analogues, e.g. 6 or 7 nucleoside analogues. In various embodiments, at least one of the nucleoside analogues is a locked nucleic acid (LNA) monomer; for example at least 3 or at least 4, or at least 5, or at least 6, or at least 7, or 8, nucleoside analogues are LNA monomers. In some embodiments, all the nucleoside analogues are LNA monomers.

It will be recognised that when referring to a preferred oligomer base sequence, in certain embodiments, the oligomers comprise a corresponding nucleoside analogue, such as a corresponding LNA monomer or other corresponding nucleoside analogue, which raise the duplex stability ($T_m$) of the oligomer/target region duplex (i.e. affinity enhancing nucleoside analogues).

In various embodiments, any mismatches (i.e., non-complementarities) between the base sequence of the oligomer and the base sequence of the target region, if present, are preferably located other than in the regions of the oligomer that contain affinity-enhancing nucleoside analogues (e.g., regions A or C), such as within region B as referred to herein, and/or within region D as referred to herein, and/or in regions consisting of DNA monomers, and/or in regions which are 5' or 3' to the region of the oligomer that is complementary to the target region.

In some embodiments the nucleoside analogues present within the oligomer of the invention (such as in regions A and C mentioned herein) are independently selected from, for example: monomers containing 2'-O-alkyl-ribose sugars, monomers containing 2'-amino-deoxyribose sugars, monomers containing 2'-fluoro-deoxyribose sugars, LNA monomers, monomers containing arabinose sugars ("ANA monomers"), monomers containing 2'-fluoro-arabinose sugars, monomers containing d-arabino-hexitol sugars ("HNA monomers"), intercalating monomers as defined in Christensen (2002) Nucl. Acids. Res. 30: 4918-4925, hereby incorporated by reference, and 2'-O-methoxyethyl-ribose (2'MOE) sugars. In some embodiments, there is only one of the above types of nucleoside analogues present in the oligomer of the invention, or region thereof.

In certain embodiments, the nucleoside analogues contain 2'MOE sugars, 2% fluoro-deoxyribose sugars, or LNA sugars, and as such the oligonucleotide of the invention may comprise nucleoside analogues which are independently selected from these three types. In certain oligomer embodiments containing nucleoside analogues, at least one of said nucleoside analogues contains a 2'-MOE-ribose sugar, such as 2, 3, 4, 5, 6, 7, 8, 9 or 10 nucleoside analogues containing 2'-MOE-ribose sugars. In some embodiments, at least one nucleoside analogue contains a 2'-fluoro-deoxyribose sugar, such as 2, 3, 4, 5, 6, 7, 8, 9 or 10 nucleoside analogues containing 2'-fluoro-DNA nucleotide sugars.

In various embodiments, the oligomer according to the invention comprises at least one Locked Nucleic Acid (LNA) monomer, such as 1, 2, 3, 4, 5, 6, 7, or 8 LNA monomers, such as 3-7 or 4 to 8 LNA monomers, or 3, 4, 5, 6 or 7 LNA monomers. In various embodiments, all the nucleoside analogues are LNA monomers. In certain embodiments, the oligomer comprises both beta-D-oxy-LNA monomers, and one or more of the following LNA monomers: thio-LNA monomers, amino-LNA monomers, oxy-LNA monomers, and/or ENA monomers in either the beta-D or alpha-L configurations, or combinations thereof. In certain embodiments, the cytosine base moieties of all LNA monomers in the oligomer are 5-methylcytosines. In certain embodiments of the invention, the oligomer comprises both LNA and DNA monomers. Typically, the combined total of LNA and DNA monomers is 10-25, preferably 10-20, even more preferably 12-16. In some embodiments of the invention, the oligomer or region thereof consists of at least one LNA monomer, and the remaining monomers are DNA monomers. In certain embodiments, the oligomer comprises only LNA monomers and nucleosides (such as RNA or DNA monomers, most preferably DNA monomers) optionally with modified linkage groups such as phosphorothioate.

In various embodiments, at least one of the nucleoside analogues present in the oligomer has a modified base selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

LNA

The term "LNA monomer" refers to a nucleoside analogue containing a bicyclic sugar (an "LNA sugar"). The terms "LNA oligonucleotide" and "LNA oligomer" refer to an oligomer containing one or more LNA monomers.

The LNA used in the oligonucleotide compounds of the invention preferably has the structure of the general formula I:

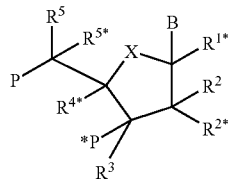

wherein X is selected from —O—, —S—, —N(R$^{N*}$), —C(R$^6$R$^{6*}$)—;

B is selected from hydrogen, optionally substituted C$_{1-4}$-alkoxy, optionally substituted C$_{1-4}$-alkyl, optionally substituted C$_{1-4}$-acyloxy, nucleobases, DNA intercalators, photochemically active groups, thermochemically active groups, chelating groups, reporter groups, and ligands;

P designates the radical position for an internucleoside linkage to a succeeding monomer, or a 5'-terminal group, such internucleoside linkage or 5'-terminal group optionally including the substituent R$^5$ or equally applicable the substituent R$^{5*}$;

P* designates an internucleoside linkage to a preceding monomer, or a 3'-terminal group;

R$^{4*}$ and R$^{2*}$ together designate a biradical consisting of 1-4 groups/atoms selected from —C(R$^a$R$^b$)—, —C(R$^a$)═C(R$^b$)—, —C(R$^a$)═N—, —O—, —Si(R$^a$)$_2$—, —N(R)—, and >C═Z, wherein Z is selected from —O—, —S—, and —N(R$^a$)—, and R$^a$ and R$^b$ each is independently selected from hydrogen, optionally substituted C$_{1-12}$-alkyl, optionally substituted C$_{2-12}$-alkenyl, optionally substituted C$_{1-12}$-alkynyl, hydroxy, C$_{2-12}$-alkoxyalkyl, C$_{2-12}$-alkenyloxy, carboxy, C$_{1-12}$-alkoxycarbonyl, C$_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-4}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, halogen, DNA intercalators, photochemically active groups, thermochemically active groups, chelating groups, reporter groups, and ligands, where aryl and heteroaryl may be optionally substituted and where two geminal substituents R$^a$ and R$^b$ together may designate optionally substituted methylene (═CH$_2$), and each of the substituents R$^{1*}$, R$^2$, R$^3$, R$^5$, R$^{5*}$, R$^6$ and R$^{6*}$, which are present is independently selected from hydrogen, optionally substituted C$_{1-12}$-alkyl, optionally substituted C$_{2-12}$-alkenyl, optionally substituted C$_{2-12}$-alkynyl, hydroxy, C$_{1-12}$-alkoxy, C$_{2-12}$-alkoxyalkyl, C$_{2-12}$-alkenyloxy, carboxy, C$_{1-12}$-alkoxycarbonyl, C$_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, alkanoyloxy, sulphono, C$_{1-6}$-alkylsulphonyloxy, nitro, azido, sulphanyl, C$_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a spiro biradical consisting of a 1-5 carbon atom(s) alkylene chain which is optionally interrupted and/or terminated by one or more heteroatoms/groups selected from —O—, —S—, and —(NR$^N$)— where R$^N$ is selected from hydrogen and C$_{1-4}$-alkyl, and where two adjacent (non-geminal) substituents may designate an additional bond resulting in a double bond; and R$^{N*}$, when present and not involved in a biradical, is selected from hydrogen and C$_{1-4}$-alkyl; and basic salts and acid addition salts thereof;

In some embodiments, R$^{5*}$ is selected from H, —CH$_3$, —CH$_2$—CH$_3$, —CH$_2$—O—CH$_3$, and —CH═CH$_2$.

In various embodiments, R$^{4*}$ and R$^{2*}$ together designate a biradical selected from —C(R$^a$R$^b$)—O—, —C(R$^a$R$^b$)—C(R$^c$R$^d$)—O—, —C(R$^a$R$^b$)—C(R$^c$R$^d$)—C(R$^e$R$^f$)—O—, —C(R$^a$R$^b$)—O—C(R$^c$R$^d$)—, —C(R$^a$R$^b$)—O—C(R$^c$R$^d$)—O—, —C(R$^a$R$^b$)—C(R$^c$R$^d$)—, —C(R$^a$R$^b$)—C(R$^c$R$^d$)—C(R$^e$R$^f$)—, —C(R$^a$)═C(R$^b$)—C(R$^c$R$^d$)—, —C(R$^a$R$^b$)—N(R$^c$)—, —C(R$^a$R$^b$)—C(R$^c$R$^d$)—N(R$^c$)—, —C(R$^a$R$^b$)—N(R$^c$)—O—, and —C(R$^a$R$^b$)—S—, —C(R$^a$R$^b$)—C(R$^c$R$^d$)—S—, wherein R$^a$, R$^b$, R$^c$, R$^d$, R$^e$, and R$^f$ each is independently selected from hydrogen, optionally substituted C$_{1-12}$-alkyl, optionally substituted C$_{2-12}$-alkenyl, optionally substituted C$_{2-12}$-alkynyl, hydroxy, C$_{1-12}$-alkoxyalkyl, C$_{2-12}$-alkenyloxy, carboxy, C$_{1-12}$-alkoxycarbonyl, C$_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=CH$_2$), In a further embodiment $R^{4*}$ and $R^{2*}$ together designate a biradical (bivalent group) selected from —CH$_2$—O—, —CH$_2$—S—, —CH$_2$—NH—, —CH$_2$—N(CH$_3$)—, —CH$_2$—CH$_2$—O—, —CH$_2$—CH(CH$_3$)—, —CH$_2$—CH$_2$—S—, —CH$_2$—CH$_2$—NH—, —CH$_2$—CH$_2$—CH$_2$—, —CH$_2$—CH$_2$—CH$_2$—O—, —CH$_2$—CH$_2$—CH(CH$_3$)—, —CH=CH—CH$_2$—, —CH$_2$—O—CH$_2$—O—, —CH$_2$—NH—O—, —CH$_2$—N(CH$_3$)—O—, —CH$_2$—O—CH$_2$—, —CH(CH$_3$)—O—, —CH(CH$_2$—O—CH$_3$)—O—.

For all chiral centers, asymmetric groups may be found in either R or S orientation.

Preferably, the LNA monomer used in the oligomer of the invention comprises at least one LNA monomer according to any of the formulas

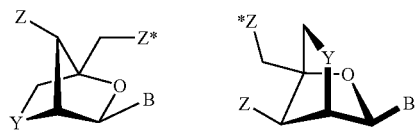

wherein Y is —O—, —O—CH2-, —S—, —NH—, or N(RH); Z and Z* are independently selected among an internucleotide linkage, a terminal group or a protecting group; B constitutes a natural or non-natural nucleotide base moiety, and $R^H$ is selected from hydrogen and C$_{1-4}$-alkyl.

Specifically preferred LNA monomers are shown in Scheme 2:

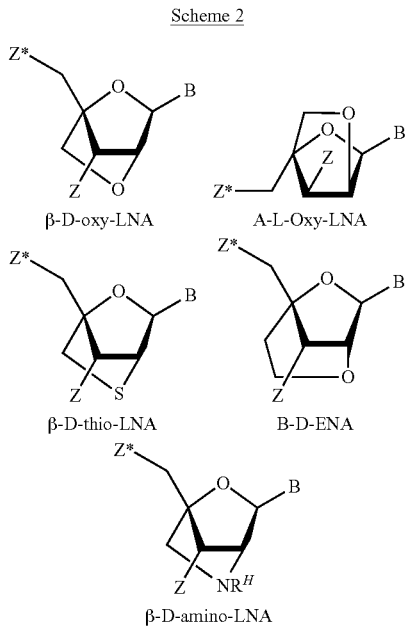

The term "thio-LNA" refers to an LNA monomer in which Y in the general formula above is selected from S or —CH$_2$—S—. Thio-LNA can be in either the beta-D or alpha-L-configuration.

The term "amino-LNA" refers to an LNA monomer in which Y in the general formula above is selected from —N(H)—, N(R)—, CH$_2$—N(H)—, and —CH$_2$—N(R)— where R is selected from hydrogen and C$_{1-4}$-alkyl. Amino-LNA can be hi either the beta-D or alpha-L-configuration.

The term "oxy-LNA" refers to an LNA monomer in which Y in the general formula above represents —O— or —CH$_2$—O—. Oxy-LNA can be in either the beta-D or alpha-L-configuration.

The term "ENA" refers to an LNA monomer in which Y in the general formula above is —CH$_2$—O— (where the oxygen atom of —CH$_2$—O— is attached to the 2'-position relative to the base B).

In various embodiments, the LNA monomer is selected from a beta-D-oxy-LNA monomer, and alpha-L-oxy-LNA monomer, a beta-D-amino-LNA monomer, and beta-D-thio-LNA monomer, in particular a beta-D-oxy-LNA monomer.

In the present context, the term "C$_{1-4}$alkyl" means a linear or branched saturated hydrocarbon chain wherein the chain has from one to four carbon atoms, such as methyl, ethyl, n-propyl, isopropyl, n-butyl, isobutyl, sec-butyl and tert-butyl.

RNAse H Recruitment

In some embodiments, an oligomer functions via non-RNase-mediated degradation of a target mRNA, such as by steric hindrance of translation, or other mechanisms; however, in various embodiments, oligomers of the invention are capable of recruiting an endo-ribonuclease (RNase), such as RNase H.

Typically, the oligomer, comprises a region of at least 6, such as at least 7 contiguous monomers, such as at least 8 or at least 9 contiguous monomers, including 7, 8, 9, 10, 11, 12, 13, 14, 15 or 16 contiguous monomers, which, when forming a duplex with the target region of the target RNA, is capable of recruiting RNase. The region of the oligomer which is capable of recruiting RNAse may be region B, as referred to in the context of a gapmer as described herein. In some embodiments, the region of the oligomer which is capable of recruiting RNAse, such as region B, consists of 10, 11, 12, 13, 14, 15, 16, 17, 18, 19 or 20 monomers.

EP 1 222 309 provides in vitro methods for determining RNaseH activity, which may be used to determine the ability of the oligomers of the invention to recruit RNaseH. An oligomer is deemed capable of recruiting RNaseH if, when contacted with the complementary region of the RNA target, it has an initial rate, as measured in pmol/l/min, of at least 1%, such as at least 5%, such as at least 10% or less than 20% of an oligonucleotide having the same base sequence but containing only DNA monomers, with no 2' substitutions, with phosphorothioate linkage groups between all monomers in the oligonucleotide, using the methodology provided by Examples 91-95 of EP 1 222 309, incorporated herein by reference.

In some embodiments, an oligomer is deemed essentially incapable of recruiting RNaseH if, when contacted with the complementary target region of the RNA target, and RNaseH, the RNaseH initial rate, as measured in pmol/l/min, is less than 1%, such as less than 5%, such as less than 10% or less than 20% of the initial rate determined using an oligonucleotide having the same base sequence, but containing only DNA monomers, with no 2' substitutions, with phosphorothioate linkage groups between all monomers in the oligonucleotide, using the methodology provided by Examples 91-95 of EP 1 222 309.

In other embodiments, an oligomer is deemed capable of recruiting RNaseH if, when contacted with the complementary target region of the RNA target, and RNaseH, the RNaseH initial rate, as measured in pmol/l/min, is at least 20%, such as at least 40%, such as at least 60%, such as at least 80% of the initial rate determined using an oligonucleotide having the same base sequence, but containing only DNA monomers, with no 2' substitutions, with phosphorothioate linkage groups between all monomers in the oligonucleotide, using the methodology provided by Examples 91-95 of EP 1 222 309.

Typically, the region of the oligomer which forms the duplex with the complementary target region of the target RNA and is capable of recruiting RNase contains DNA monomers and LNA monomers and forms a DNA/RNA-like duplex with the target region. The LNA monomers are preferably in the alpha-L configuration, particularly preferred being alpha-L-oxy LNA.

In various embodiments, the oligomer of the invention comprises both nucleosides and nucleoside analogues, and is in the form of a gapmer, a headmer or a mixmer.

A "headmer" is defined as an oligomer that comprises a first region and a second region that is contiguous thereto, with the 5'-most monomer of the second region linked to the 3'-most monomer of the first region. The first region comprises a contiguous stretch of non-RNase recruiting nucleoside analogues and the second region comprises a contiguous stretch (such as at least 7 contiguous monomers) of DNA monomers or nucleoside analogue monomers recognizable and cleavable by the RNase A "tailmer" is defined as an oligomer that comprises a first region and a second region that is contiguous thereto, with the 5'-most monomer of the second region linked to the 3'-most monomer of the first region. The first region comprises a contiguous stretch (such as at least 7 contiguous monomers) of DNA monomers or nucleoside analogue monomers recognizable and cleavable by the RNase, and the second region comprises a contiguous stretch of non-RNase recruiting nucleoside analogues.

Other "chimeric" oligomers, called "mixmers", consist of an alternating composition of (i) DNA monomers or nucleoside analogue monomers recognizable and cleavable by RNase, and (ii) non-RNase recruiting nucleoside analogue monomers.

In some embodiments, in addition to enhancing affinity of the oligomer for the target region, some nucleoside analogues also mediate RNase (e.g., RNaseH) binding and cleavage. Since •-L-LNA monomers recruit RNaseH activity to a certain extent, in some embodiments, gap regions (e.g., region B as referred to herein) of oligomers containing •-L-LNA monomers consist of fewer monomers recognizable and cleavable by the RNaseH, and more flexibility in the mixmer construction is introduced.

Conjugates

In the context of this disclosure, the term "conjugate" indicates a compound formed by the covalent attachment ("conjugation") of an oligomer as described herein, to one or more moieties that are not themselves nucleic acids or monomers ("conjugated moieties"). Examples of such conjugated moieties include macromolecular compounds such as proteins, fatty acid chains, sugar residues, glycoproteins, polymers, or combinations thereof. Typically proteins may be antibodies for a target protein. Typical polymers may be polyethylene glycol.

Accordingly, provided herein are conjugates comprising an oligomer as herein described, and at least one conjugated moiety that is not a nucleic acid or monomer, covalently attached to said oligomer. Therefore, in certain embodiments where the oligomer of the invention consists of contiguous monomers having a specified sequence of bases, as herein disclosed, the conjugate may also comprise at least one conjugated moiety that is covalently attached to the oligomer.

In various embodiments of the invention, the oligomer is conjugated to a moiety that increases the cellular uptake of oligomeric compounds. WO2007/031091 provides suitable ligands and conjugates, which are hereby incorporated by reference.

In various embodiments, conjugation (to a conjugated moiety) may enhance the activity, cellular distribution or cellular uptake of the oligomer of the invention. Such moieties include, but are not limited to, antibodies, polypeptides, lipid moieties such as a cholesterol moiety, cholic acid, a thioether, e.g. Hexyl-s-tritylthiol, a thiocholesterol, an aliphatic chain, e.g., dodecandiol or undecyl residues, a phospholipids, e.g., di-hexadecyl-rac-glycerol or triethylammonium 1,2-di-o-hexadecyl-rac-glycero-3-h-phosphonate, a polyamine or a polyethylene glycol chain, an adamantane acetic acid, a palmityl moiety, an octadecylamine or hexylamino-carbonyl-oxycholesterol moiety.

In certain embodiments, the oligomers of the invention are conjugated to active drug substances, for example, aspirin, ibuprofen, a sulfa drug, an antidiabetic, an antibacterial or an antibiotic.

In certain embodiments the conjugated moiety is a sterol, such as cholesterol.

In various embodiments, the conjugated moiety comprises or consists of a positively charged polymer, such as a positively charged peptides of, for example 1-50, such as 2-20 such as 3-10 amino acid residues in length, and/or polyalkylene oxide such as polyethylene glycol (PEG) or polypropylene glycol—see WO 2008/034123, hereby incorporated by reference. Suitably the positively charged polymer, such as a polyalkylene oxide may be attached to the oligomer of the invention via a linker such as the releasable linker described in WO 2008/034123.

By way of example, the following moieties may be used in the conjugates of the invention:

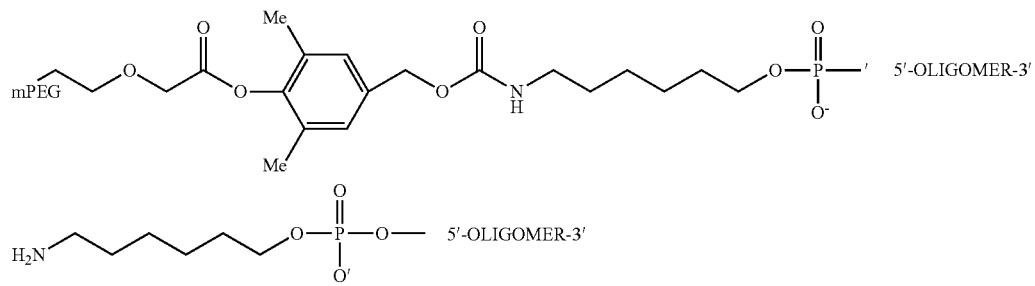

Activated Oligomers

The term "activated oligomer," as used herein, refers to an oligomer of the invention that is covalently linked (i.e., functionalized) to at least one functional moiety that permits covalent linkage of the oligomer to one or more conjugated moieties, i.e., moieties that are not themselves nucleic acids or monomers, to form the conjugates herein described. Typically, a functional moiety will comprise a chemical group that is capable of covalently bonding to the oligomer via, e.g., a 3'-hydroxyl group or the exocyclic $NH_2$ group of the adenine base, a spacer that is preferably hydrophilic and a terminal group that is capable of binding to a conjugated moiety (e.g., an amino, sulfhydryl or hydroxyl group). In some embodiments, this terminal group is not protected, e.g., is an NH, group. In other embodiments, the terminal group is protected, for example, by any suitable protecting group such as those described in "Protective Groups in Organic Synthesis" by Theodora W. Greene and Peter G. M. Wuts, 3rd edition (John Wiley & Sons, 1999). Examples of suitable hydroxyl protecting groups include esters such as acetate ester, aralkyl groups such as benzyl, diphenylmethyl, or triphenylmethyl, and tetrahydropyranyl. Examples of suitable amino protecting groups include benzyl, alpha-methylbenzyl, diphenylmethyl, triphenylmethyl, benzyloxycarbonyl, tert-butoxycarbonyl, and acyl groups such as trichloroacetyl or trifluoroacetyl.

In some embodiments, the functional moiety is self-cleaving. In other embodiments, the functional moiety is biodegradable. See e.g., U.S. Pat. No. 7,087,229, which is incorporated by reference herein in its entirety.

In some embodiments, oligomers of the invention are functionalized at the 5' end in order to allow covalent attachment of the conjugated moiety to the 5' end of the oligomer. In other embodiments, oligomers of the invention can be functionalized at the 3' end. In still other embodiments, oligomers of the invention can be functionalized along the backbone or on the heterocyclic base moiety. In yet other embodiments, oligomers of the invention can be functionalized at more than one position independently selected from the 5' end, the 3' end, the backbone and the base.

In some embodiments, activated oligomers of the invention are synthesized by incorporating during the synthesis one or more monomers that is covalently attached to a functional moiety. In other embodiments, activated oligomers of the invention are synthesized with monomers that have not been functionalized, and the oligomer is functionalized upon completion of synthesis.

In some embodiments, the oligomers are functionalized with a hindered ester containing an aminoalkyl linker, wherein the alkyl portion has the formula $(CH_2)_w$, wherein w is an integer ranging from 1 to 10, preferably about 6, wherein the alkyl portion of the alkylamino group can be straight chain or branched chain, and wherein the functional group is attached to the oligomer via an ester group (—O—C(O)—$(CH_2)_w$NH).

In other embodiments, the oligomers are functionalized with a hindered ester containing a $(CH_2)_w$-sulfhydryl (SH) linker, wherein w is an integer ranging from 1 to 10, preferably about 6, wherein the alkyl portion of the alkylamino group can be straight chain or branched chain, and wherein the functional group attached to the oligomer via an ester group (—O—C(O)—$(CH_2)_w$SH) In some embodiments, sulfhydryl-activated oligonucleotides are conjugated with polymer moieties such as polyethylene glycol or peptides (via formation of a disulfide bond).

Activated oligomers containing hindered esters as described above can be synthesized by any method known in the art, and in particular, by methods disclosed in PCT Publication No. WO 2008/034122 and the examples therein, which is incorporated herein by reference in its entirety.

Activated oligomers covalently linked to at least one functional moiety can be synthesized by any method known in the art, and in particular, by methods disclosed in U.S. Patent Publication No. 2004/0235773, which is incorporated herein by reference in its entirety, and in Zhao et al. (2007) J. Controlled Release 119:143-152; and Zhao et al. (2005) Bioconjugate Chem. 16:758-766.

In still other embodiments, the oligomers of the invention are functionalized by introducing sulfhydryl, amino or hydroxyl groups into the oligomer by means of a functionalizing reagent substantially as described in U.S. Pat. Nos. 4,962,029 and 4,914,210, i.e., a substantially linear reagent having a phosphoramidite at one end linked through a hydrophilic spacer chain to the opposing end which comprises a protected or unprotected sulfhydryl, amino or hydroxyl group. Such reagents primarily react with hydroxyl groups of the oligomer. In some embodiments, such activated oligomers have a functionalizing reagent coupled to a 5'-hydroxyl group of the oligomer. In other embodiments, the activated oligomers have a functionalizing reagent coupled to a 3'-hydroxyl group. In still other embodiments, the activated oligomers of the invention have a functionalizing reagent coupled to a hydroxyl group on the backbone of the oligomer. In yet further embodiments, the oligomer of the invention is functionalized with more than one of the functionalizing reagents as described in U.S. Pat. Nos. 4,962,029 and 4,914,210, incorporated herein by reference in their entirety. Methods of synthesizing such functionalizing reagents and incorporating them into monomers or oligomers are disclosed in U.S. Pat. Nos. 4,962,029 and 4,914,210.

In some embodiments, the 5'-terminus of a solid-phase bound oligomer is functionalized with a dienyl phosphoramidite derivative, followed by conjugation of the deprotected oligomer with, e.g., an amino acid or peptide via a Diels-Alder cycloaddition reaction.

In various embodiments, the incorporation of monomers containing 2'-sugar modifications, such as a 2'-carbamate substituted sugar or a 2'-(O-pentyl-N-phthalimido)-deoxyribose sugar into the oligomer facilitates covalent attachment of conjugated moieties to the sugars of the oligomer. In other embodiments, an oligomer with an amino-containing linker at the 2'-position of one or more monomers is prepared using a reagent such as, for example, 5'-dimethoxytrityl-2'-O-(e-phthalimidylaminopentyl)-2'-deoxyadenosine-3'-N,N-diisopropyl-cyanoethoxy phosphoramidite. See, e.g., Manoharan, et al., Tetrahedron Letters, 1991, 34, 7171.

In still further embodiments, the oligomers of the invention have amine-containing functional moieties on the nucleobase, including on the N6 purine amino groups, on the exocyclic N2 of guanine, or on the N4 or 5 positions of cytosine. In various embodiments, such functionalization may be achieved by using a commercial reagent that is already functionalized in the oligomer synthesis.

Some functional moieties are commercially available, for example, heterobifunctional and homobifunctional linking moieties are available from the Pierce Co. (Rockford, Ill.). Other commercially available linking groups are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, and 3'-Amino-Modifier is also available from Clontech Laboratories Inc. (Palo Alto, Calif.).

Compositions

In various embodiments, the oligomer of the invention is used in pharmaceutical formulations and compositions. Suitably, such compositions comprise a pharmaceutically acceptable diluent, carrier, salt or adjuvant. PCT/DK2006/000512 provides suitable and preferred pharmaceutically acceptable diluents, carriers and adjuvants—which are hereby incorporated by reference. Suitable dosages, formulations, administration routes, compositions, dosage forms, combinations with other therapeutic agents, pro-drug formulations are also provided in PCT/DK2006/000512—which are also hereby incorporated by reference. Details on techniques for formulation and administration also may be found in the latest edition of "REMINGTON'S PHARMACEUTICAL SCIENCES" (Maack Publishing Co, Easton Pa.).

In some embodiments, an oligomer of the invention is covalently linked to a conjugated moiety to aid in delivery of the oligomer across cell membranes. An example of a conjugated moiety that aids in delivery of the oligomer across cell membranes is a lipophilic moiety, such as cholesterol. In various embodiments, an oligomer of the invention is formulated with lipid formulations that form liposomes, such as Lipofectamine 2000 or Lipofectamine RNAiMAX, both of which are commercially available from Invitrogen. In some embodiments, the oligomers of the invention are formulated with a mixture of one or more lipid-like non-naturally occurring small molecules ("lipidoids"). Libraries of lipidoids can be synthesized by conventional synthetic chemistry methods and various amounts and combinations of lipidoids can be assayed in order to develop a vehicle for effective delivery of an oligomer of a particular size to the targeted tissue by the chosen route of administration. Suitable lipidoid libraries and compositions can be found, for example in Akinc et al. (2008) Nature Biotechnol., available at http://www.nature.com/nbt/journal/vaop/ncurrent/abs/nbt1402.html, which is incorporated by reference herein.

As used herein, the term "pharmaceutically acceptable salts" refers to salts that retain the desired biological activity of the herein identified compounds and exhibit acceptable levels of undesired toxic effects. Non-limiting examples of such salts can be formed with organic amino acid and base addition salts formed with metal cations such as zinc, calcium, bismuth, barium, magnesium, aluminum, copper, cobalt, nickel, cadmium, sodium, potassium, and the like, or with a cation formed from ammonia, N,N'-dibenzylethylenediamine, D-glucosamine, tetraethylammonium, or ethylenediamine; or (c) combinations of (a) and (b); e.g., a zinc tannate salt or the like.

In certain embodiments, the pharmaceutical compositions according to the invention comprise other active ingredients in addition to an oligomer or conjugate of the invention, including active agents useful for the treatment of cancer, such as prostate cancer or breast cancer, particularly agents used in conventional antiandrogen therapy.

In some embodiments, additional active agents are non-steroidal antiandrogens (NSAAs), which block the binding of androgens at the receptor site, or luteinizing hormone-releasing hormone analogues (LHRH-As) that suppress testicular production of androgens to castrate levels.

NSAAs such as CASODEX, when used with an LHRH-A as part of Combined Androgen Blockade therapy, help to inhibit the growth of prostate cancer cells. In one embodiment, the invention provides for a combined androgen blockade therapy, characterised in that the therapy comprises administering the pharmaceutical composition according to the invention, and an NSAA and/or LHRH-A agent, which in certain embodiments are administered prior to, during or subsequent to the administration of the pharmaceutical compositions of the invention.

The invention also provides a kit of parts wherein a first part comprises at least one oligomer, conjugate and/or the pharmaceutical composition according to the invention and a further part comprises a non-steroidal antiandrogen and/or a luteinizing hormone-releasing hormone analogue. It is therefore envisaged that the kit of parts may be used in a method of treatment, as referred to herein, where the method comprises administering both the first part and the further part, either simultaneously or one after the other.

Applications

The term "treatment" as used herein refers to both treatment of an existing disease (e.g., a disease or disorder as referred to herein below), or prevention of a disease, i.e., prophylaxis. It will therefore be recognised that, in certain embodiments, "treatment" includes prophylaxis.

In various embodiments, the oligomers of the invention may be utilized as research reagents for, for example, diagnostics, therapeutics and prophylaxis.

In some embodiments, such oligomers may be used for research purposes to specifically inhibit the expression of androgen receptor protein (typically by degrading or inhibiting the AR mRNA and thereby preventing protein formation) in cells and experimental animals, thereby facilitating functional analysis of the target or an appraisal of its usefulness as a target for therapeutic intervention.

In certain embodiments, the oligomers may be used in diagnostics to detect and quantitate androgen receptor expression in cells and tissues by Northern blotting, in-situ hybridisation or similar techniques.

In various therapeutic embodiments, a non-human animal or a human suspected of having a disease or disorder which can be treated by modulating the expression of androgen receptor is treated by administering an effective amount of an oligomer in accordance with this invention. Further provided are methods of treating a mammal, such as treating a human, suspected of having or being prone to a disease or condition, associated with expression of androgen receptor by administering a therapeutically or prophylactically effective amount of one or more of the oligomers, conjugates or compositions of the invention.

In certain embodiments, the invention also provides for the use of the compounds or conjugates of the invention as described for the manufacture of a medicament for the treatment of a disorder as referred to herein, or for a method of the treatment of a disorder as referred to herein.

In various embodiments, the invention also provides for a method for treating a disorder as referred to herein, said method comprising administering a compound according to the invention as herein described, and/or a conjugate according to the invention, and/or a pharmaceutical composition according to the invention to a patient in need thereof.

Medical Indications

In certain therapeutic embodiments, the disorder to be treated is cancer, such as prostate cancer or breast cancer. In various embodiments, the treatment of such a disease or condition according to the invention may be combined with one or more other anti-cancer treatments, such as radiotherapy, chemotherapy or immunotherapy.

In certain other embodiments, the disorder to be treated is selected from alopecia, benign prostatic hyperplasia, spinal and muscular atrophy and Kennedy disease and polyglutamate disease.

In various embodiments, the disease or disorder is associated with a mutation of the AR gene or a gene whose protein product is associated with or interacts with AR. Therefore, in various embodiments, the target snRNA is a mutated form of the AR sequence, for example, it comprises one or more single point mutations or triplet repeats.

In other embodiments, the disease or disorder is associated with abnormal levels of a mutated form of androgen receptor. In various embodiments, the disease or disorder is associated with abnormal levels of a wild-type form of AR.

In various embodiments, the invention relates to methods of modulating the expression of the gene product of an androgen receptor target gene, i.e., a gene that is regulated by AR. Such AR receptor target gene products are selected form the group consisting of Protein kinase C delta (PRKCD), Glutathione S-transferase theta 2 (GSTT2), transient receptor potential cation channel subfamily V member 3 (TRPV3), Pyrroline-5-carboxylate reductase 1 (PYCR1) and ornithine aminotransferase (OAT). In some embodiments, modulation of an AR target gene results in increased expression or activity of the target gene. In other embodiments, modulation of an AR target gene results in decreased expression or activity of the target gene.

The invention further provides use of a compound of the invention in the manufacture of a medicament for the treatment of any and all conditions disclosed herein.

In various embodiments, the invention is directed to a method of treating a mammal suffering from or susceptible to a condition associated with abnormal levels of androgen receptor mRNA or protein, comprising administering to the mammal a therapeutically effective amount of an oligomer of the invention, or a conjugate thereof, that comprises one or more LNA monomers.

An interesting aspect of the invention is directed to the use of an oligomer (compound) as defined herein or a conjugate as defined herein for the preparation of a medicament for the treatment of a condition as disclosed herein above.

In various embodiments, the invention encompasses a method of preventing or treating a disease comprising administering a therapeutically effective amount of an oligomer according to the invention, or a conjugate thereof, to a human in need of such therapy.

In certain embodiments, the LNA oligomers of the invention, or conjugates thereof, are administered for a short period time rather than continuously.

In certain embodiments of the invention, the oligomer (compound) is linked to a conjugated moiety, for example, in order to increase the cellular uptake of the oligomer. In one embodiment the conjugated moiety is a sterol, such as cholesterol.

In various embodiments, the invention is directed to a method for treating abnormal levels of androgen receptor, the method comprising administering an oligomer of the invention, or a conjugate or a pharmaceutical composition thereof, to a patient in need of such treatment, and further comprising the administration of a further chemotherapeutic agent. In some embodiments, the chemotherapeutic agent is conjugated to the oligomer, is present in the pharmaceutical composition, or is administered in a separate formulation.

The invention also relates to an oligomer, a composition or a conjugate as defined herein for use as a medicament.

The invention further relates to use of a compound, composition, or a conjugate as defined herein for the manufacture of a medicament for the treatment of abnormal levels of androgen receptor or expression of mutant forms of AR (such as allelic variants, such as those associated with one of the diseases referred to herein).

Moreover, in various embodiments, the invention relates to a method of treating a subject suffering from a disease or condition selected from cancer, such as breast cancer or prostate cancer, alopecia, benign prostatic hyperplasia, spinal and muscular atrophy, Kennedy disease and polyglutamate disease, the method comprising the step of administering a pharmaceutical composition as defined herein to the subject in need thereof.

Suitable dosages, formulations, administration routes, compositions, dosage forms, combinations with other therapeutic agents, pro-drug formulations are also provided in PCT/DK2006/000512—which is hereby incorporated by reference.

The invention also provides for a pharmaceutical composition comprising a compound or a conjugate as herein described or a conjugate, and a pharmaceutically acceptable diluent, carrier or adjuvant. PCT/DK2006/000512 provides suitable and preferred pharmaceutically acceptable diluents, carriers and adjuvants—which are hereby incorporated by reference.

EMBODIMENTS

The following embodiments of the invention may be used in combination with the other embodiments described herein.

1. An oligomer of between 10-50 nucleobases in length which comprises a contiguous nucleobase sequence of a total of between 10-50 nucleobases, wherein said contiguous nucleobase sequence is at least 80% homologous to a corresponding region of a nucleic acid which encodes a mammalian androgen receptor.

2. The oligomer according to embodiment 1, wherein said oligomer comprises at least one LNA unit.

3. The oligomer according to embodiment 1 or 2, wherein the contiguous nucleobase sequence comprises no more than 3, such as no more than 2 mismatches to the corresponding region of a nucleic acid which encodes a mammalian androgen receptor.

4. The oligomer according to embodiment 3, wherein said contiguous nucleobase sequence comprises no more than a single mismatch to the corresponding region of a nucleic acid which encodes a mammalian androgen receptor.

5. The oligomer according to embodiment 4, wherein said contiguous nucleobase sequence comprises no mismatches, (i.e. is complementary to) the corresponding region of a nucleic acid which encodes a mammalian androgen receptor.

6. The oligomer according to any one of embodiments 1-5, wherein the nucleobase sequence of the oligomer consists of the contiguous nucleobase sequence.

7. The oligomer according to any one of embodiments 1-6, wherein the nucleic acid which encodes a mammalian androgen receptor is the human androgen receptor nucleotide sequence such as SEQ ID No 1, or a naturally occurring allelic variant thereof.

8. The oligomer according to any one of embodiments 1-7, wherein the contiguous nucleobase sequence is complementary to a corresponding region of both the human androgen receptor nucleic acid sequence and a non-human mammalian androgen receptor nucleic acid sequence, such as the mouse androgen receptor nucleic acid sequence.

9. The oligomer according to any one of embodiments 1 to 8, wherein the contiguous nucleobase sequence comprises a contiguous subsequence of at least 7, nucleobase residues which, when formed in a duplex with the complementary androgen receptor target RNA is capable of recruiting RNaseH.

10. The oligomer according to embodiment 9, wherein the contiguous nucleobase sequence comprises of a contiguous subsequence of at least 8, at least 9 or at least 10 nucleobase residues which, when formed in a duplex with the complementary androgen receptor target RNA is capable of recruiting RNaseH.

11. The oligomer according to any one of embodiments 9 or 10 wherein said contiguous subsequence is at least 9 or at least 10 nucleobases in length, such as at least 12 nucleobases or at least 14 nucleobases in length, such as 14, 15 or 16 nucleobases residues which, when formed in a duplex with the complementary androgen receptor target RNA is capable of recruiting RNaseH.

12. The oligomer according to embodiment any one of embodiments 1-11 wherein said oligomer is conjugated with one or more non-nucleobase compounds.

13. The oligomer according to any one of embodiments 1-12, wherein said oligomer has a length of between 10-22 nucleobases.

14. The oligomer according to any one of embodiments 1-13, wherein said oligomer has a length of between 12-18 nucleobases.

15. The oligomer according to any One of embodiments 1-14, wherein said oligomer has a length of 14, 15 or 16 nucleobases.

16. The oligomer according to any one of embodiments 1-15, wherein said continuous nucleobase sequence corresponds to a contiguous nucleotide sequence present in a nucleic acid sequence selected from the group consisting of SEQ ID NO 86-106.

17. The oligomer according to any one of embodiments 1-16, wherein the oligomer or contiguous nucleobase sequence comprises, or is selected from a corresponding nucleobase sequence present in a nucleotide sequence selected from the group consisting of SEQ ID NO 2-22.

18. The oligomer according to any one of embodiments 1-17, wherein said contiguous nucleobase sequence comprises at least one affinity enhancing nucleotide analogue.

19. The oligomer according to embodiment 18, wherein said contiguous nucleobase sequence comprises a total of 2, 3, 4, 5, 6, 7, 8, 9 or 10 affinity enhancing nucleotide analogues, such as between 5 and 8 affinity enhancing nucleotide analogues.

20. The oligomer according to any one of embodiments 1-19 which comprises at least one affinity enhancing nucleotide analogue, wherein the remaining nucleobases are selected from the group consisting of DNA nucleotides and RNA nucleotides, preferably DNA nucleotides.

21. The oligomer according to any one of embodiments 1-20, wherein the oligomer comprises of a sequence of nucleobases of formula, in 5' to 3' direction, A-B-C, and optionally of formula A-B-C-D, wherein:
(a) consists or comprises of at least one nucleotide analogue, such as 1, 2, 3, 4, 5 or 6 nucleotide analogues, preferably between 2-5 nucleotide analogues, preferably 2, 3 or 4 nucleotide analogues, most preferably 2, 3 or 4 consecutive nucleotide analogues and;
(b) consists or comprises at least five consecutive nucleobases which are capable of recruiting RNAseH (when formed in a duplex with a complementary RNA molecule, such as the AR mRNA target), such as DNA nucleobases, such as 5, 6, 7, 8, 9, 10, 11 or 12 consecutive nucleobases which are capable of recruiting RNAseH, or between 6-10, or between 7-9, such as 8 consecutive nucleobases which are capable of recruiting RNAseH, and;
(c) consists or comprises of at least one nucleotide analogue, such as 1, 2, 3, 4, 5, or 6 nucleotide analogues, preferably between 2-5 nucleotide analogues, such as 2, 3 or 4 nucleotide analogues, most preferably 2, 3 or 4 consecutive nucleotide analogues, and;
(d) when present, consists or comprises, preferably consists, of one or more DNA nucleotide, such as between 1-3 or 1-2 DNA nucleotides.

22. The oligomer according to embodiment 21, wherein region A consists or comprises of 2, 3 or 4 consecutive nucleotide analogues.

23. The oligomer according to any one of embodiments 21-22, wherein region B consists or comprises of 7, 8, 9 or 10 consecutive DNA nucleotides or equivalent nucleobases which are capable of recruiting RNAseH when formed in a duplex with a complementary RNA, such as the androgen receptor mRNA target.

24. The oligomer according to any one of embodiments 21-23, wherein region C consists or comprises of 2, 3 or 4 consecutive nucleotide analogues.

25. The oligomer according to any one of embodiments 21-24, wherein region D consists, where present, of one or two DNA nucleotides.

26. The oligomer according to any one of embodiments 21-25, wherein:
(a) Consists or comprises of 3 contiguous nucleotide analogues;
(b) Consists or comprises of 7, 8, 9 or 10 contiguous DNA nucleotides or equivalent nucleobases which are capable of recruiting RNAseH when formed in a duplex with a complementary RNA, such as the androgen receptor mRNA target;
(c) Consists or comprises of 3 contiguous nucleotide analogues;
(d) Consists, where present, of one or two DNA nucleotides.

27. The oligomer according to embodiment 26, wherein the contiguous nucleobase sequence consists of 10, 11, 12, 13 or 14 nucleobases, and wherein;
(a) Consists of 1, 2 or 3 contiguous nucleotide analogues;
(b) Consists of 7, 8, or 9 consecutive DNA nucleotides or equivalent nucleobases which are capable of recruiting RNAseH when formed in a duplex with a complementary RNA, such as the androgen receptor mRNA target;
(c) Consists of 1, 2 or 3 contiguous nucleotide analogues;
(d) Consists, where present, of one DNA nucleotide.

28. The oligomer according to anyone of embodiments 21-27, wherein B comprises at least one LNA nucleobase which is in the alpha-L configuration, such as alpha-L-oxy LNA.

29. The oligomer according to any one of embodiments 1-28, wherein the nucleotide analogue(s) are independently or collectively selected from the group consisting of: Locked Nucleic Acid (LNA) units; 2'-O-alkyl-RNA units, 2'-OMe-RNA units, 2'-amino-DNA units, 2'-fluoro-DNA units, PNA units, HNA units, and INA units.

30. The oligomer according to embodiment 29 wherein all the nucleotide analogues(s) are LNA units.

31. The oligomer according to any one of embodiments 1-30, which comprises 1, 2, 3, 4, 5, 6, 7, 8, 9 or 10 LNA units such as between 2 and 8 nucleotide LNA units.

32. The oligomer according to any one of the embodiments 29-31, wherein the LNAs are independently selected from oxy-LNA, thio-LNA, and amino-LNA, in either of the beta-D and alpha-L configurations or combinations thereof.

33. The oligomer according to embodiment 32, wherein the LNAs are all beta-D-oxy-LNA.

34. The oligomer according to any one of embodiments 21-33, wherein the nucleotide analogues or nucleobases of regions A and C are beta-D-oxy-LNA.

35. The oligomer according to any one of embodiments 1-34, wherein at least one of the nucleobases present in the oligomer is a modified nucleobase selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

36. The oligomer according to any one of embodiments 1-35, wherein said oligomer hybridises with a corresponding mammalian androgen receptor mRNA with a $T_m$ of at least 50° C.

37. The oligomer according to any one of embodiments 1-36, wherein said oligomer hybridises with a corresponding mammalian androgen receptor mRNA with a $T_m$, of no greater than 80° C.

38. The oligomer according to any one of embodiments 1-37, wherein the internucleoside linkages are independently selected from the group consisting of: phosphodiester, phosphorothioate and boranophosphate.

39. The oligomer according to embodiment 38, wherein the oligomer comprises at least one phosphorothioate internucleoside linkage.

40. The oligomer according to embodiment 39, wherein the internucleoside linkages adjacent to or between DNA or RNA units, or within region B are phosphorothioate linkages.

41. The oligomer according to embodiment 39 or 40, wherein the linkages between at least one pair of consecutive nucleotide analogues is a phosphodiester linkage.

42. The oligomer according to embodiment 39 or 40, wherein all the linkages between consecutive nucleotide analogues are phosphodiester linkages.

43. The oligomer according to embodiment 42 wherein all the internucleoside linkages are phosphorothioate linkages.

44. A conjugate comprising the oligomer according to any one of the embodiments 1-43 and at least one non-nucleotide or non-polynucleotide moiety covalently attached to said compound.

45. A pharmaceutical composition comprising an oligomer as defined in any of embodiments 1-43 or a conjugate as defined in embodiment 44, and a pharmaceutically acceptable diluent, carrier, salt or adjuvant.

46. A pharmaceutical composition according to 45, wherein the oligomer is constituted as a pro-drug.

47. A pharmaceutical composition according to embodiment 45 or 46, which further comprises a further therapeutic agent selected from the group consisting of Non-steroidal Antiandrogens and Luteinizing hormone-releasing hormone analogues.

48. Use of an oligomer as defined in any one of the embodiments 1-43, or a conjugate as defined in embodiment 44, for the manufacture of a medicament for the treatment of a disease or disorder selected from the group consisting of: Cancer such as breast cancer or prostate cancer, alopecia, benign prostatic hyperplasia, spinal and muscular atrophy, Kennedy disease and polyglutamate disease.

49. An oligomer as defined in any one of the embodiments 1-43, or a conjugate as defined in embodiment 44, for use in the treatment of a disease or disorder selected from the group consisting of: Cancer such as breast cancer or prostate cancer, alopecia, benign prostatic hyperplasia, spinal and muscular atrophy, Kennedy disease and polyglutamate disease.

50. A method for treating a disease or disorder selected from the group consisting of: Cancer such as breast cancer or prostate cancer, alopecia, benign prostatic hyperplasia, spinal and muscular atrophy, Kennedy disease and polyglutamate disease, said method comprising administering an oligomer as defined in one of the embodiments 1-43, or a conjugate as defined in embodiment 44, or a pharmaceutical composition as defined in any one of the embodiments 45-47, to a patient in need thereof.

51. A method for treating an cancer such as prostate cancer or breast cancer, said method comprising administering an oligomer as defined in one of the embodiments 1-43, or a conjugate as defined in embodiment 44, or a pharmaceutical composition as defined in any one of the embodiments 45-47, to a patient in need thereof.

52. A method of reducing or inhibiting the expression of androgen receptor in a cell or a tissue, the method comprising the step of contacting said cell or tissue with a compound as defined in one of the embodiments 1-43, or a conjugate as defined in embodiment 44, or a pharmaceutical composition as defined in any one of the embodiments 45-47, so that expression of androgen receptor is reduce or inhibited.

A method for modulating the expression of a gene which is regulated by the androgen receptor (i.e. an androgen receptor target) in a cell which is expressing said gene, said method comprising the step of contacting said cell or tissue with a compound as defined in one of the embodiments 1-43, or a conjugate as defined in embodiment 44, or a pharmaceutical composition as defined in any one of the embodiments 45-47, so that expression of androgen receptor target is modulated.

EXAMPLES

Example 1

Monomer Synthesis

The LNA monomer building blocks and derivatives were prepared following published procedures and references cited therein—see WO07/031,081 and the references cited therein.

Example 2

Oligonucleotide Synthesis

Oligonucleotides were synthesized according to the method described in WO07/031,081. Table 1 shows examples of sequences of antisense oligonucleotides of the invention. Tables 2 and 3 show examples of antisense oligonucleotides (oligomers) of the invention.

Example 3

Design of the Oligonucleotides

In accordance with the invention, a series of oligomers were designed to target different regions of human androgen receptor mRNA (GenBank Accession number NM_000044; SEQ ID NO: 1).

SEQ ID NOS: 2-22, shown in Table 1, below, are sequences of oligomers designed to target human androgen receptor mRNA. The target region of the target nucleic acid is indicated, in the table.

TABLE 1

Antisense Oligonucleotide Sequences

| SEQ ID NO | Sequence (5'-3') | Length (bases) | Target site NM_000044 |
|---|---|---|---|
| SEQ ID NO: 2 | GAGAACCATCCTCACC | 16 | 1389-1404 |
| SEQ ID NO: 3 | GGACCAGGTAGCCTGT | 16 | 1428-1443 |
| SEQ ID NO: 4 | CCCCTGGACTCAGATG | 16 | 1881-1896 |
| SEQ ID NO: 5 | GCACAAGGAGTGGGAC | 16 | 1954-1969 |
| SEQ ID NO: 6 | GCTGTGAAGAGAGTGT | 16 | 2422-2437 |
| SEQ ID NO: 7 | TTTGACACAAGTGGGA | 16 | 2663-2678 |
| SEQ ID NO: 8 | GTGACACCCAGAAGCT | 16 | 2813-2828 |
| SEQ ID NO: 9 | CATCCCTGCTTCATAA | 16 | 2975-2990 |
| SEQ ID NO: 10 | ACCAAGTTTCTTCAGC | 16 | 3008-3023 |
| SEQ ID NO: 11 | CTTGGCCCACTTGACC | 16 | 3263-3278 |
| SEQ ID NO: 12 | TCCTGGAGTTGACATT | 16 | 3384-3399 |
| SEQ ID NO: 13 | CACTGGCTGTACATCC | 16 | 3454-3469 |
| SEQ ID NO: 14 | CATCCAAACTCTTGAG | 16 | 3490-3505 |
| SEQ ID NO: 15 | GCTTTCATGCACAGGA | 16 | 3529-3544 |
| SEQ ID NO: 16 | GAAGTTCATCAAAGAA | 16 | 3594-3609 |
| SEQ ID NO: 17 | AGTTCCTTGATGTAGT | 16 | 3616-3631 |
| SEQ ID NO: 18 | TTGCACAGAGATGATC | 16 | 3809-3824 |
| SEQ ID NO: 19 | GATGGGCTTGACTTTC | 16 | 3845-3860 |
| SEQ ID NO: 20 | CAGGCAGAAGACATCT | 16 | 3924-3939 |
| SEQ ID NO: 21 | CCCAAGGCACTGCAGA | 16 | 3960-3975 |
| SEQ ID NO: 22 | GCTGACATTCATAGCC | 16 | 3114-3129 |
| SEQ ID NO: 86 | TGGGGAGAACCATCCTCACCCTGC | 24 | 1385-1408 |
| SEQ ID NO: 87 | TCCAGGACCAGGTAGCCTGTGGGG | 24 | 1424-1447 |
| SEQ ID NO: 88 | TGTTCCCCTGGACTCAGATGCTCC | 24 | 1877-1990 |
| SEQ ID NO: 89 | TGGGGCACAAGGAGTGGGACGCAC | 24 | 1950-1973 |
| SEQ ID NO: 90 | TTCGGCTGTGAAGAGAGTGTGCCA | 24 | 2418-2441 |
| SEQ ID NO: 91 | CGCTTTTGACACAAGTGGGACTGG | 24 | 2659-2682 |
| SEQ ID NO: 92 | CATAGTGACACCCAGAAGCTTCAT | 24 | 2809-2832 |
| SEQ ID NO: 93 | GAGTCATCCCTGCTTCATAACATT | 24 | 2971-2994 |
| SEQ ID NO: 94 | GATTACCAAGTTTCTTCAGCTTCC | 24 | 3004-3027 |
| SEQ ID NO: 95 | AGGCCTTGGCCCACTTGACCACGT | 24 | 3259-3282 |
| SEQ ID NO: 96 | AGCATCCTGGAGTTGACATTGGTG | 24 | 3380-3403 |
| SEQ ID NO: 97 | GACACACTGGCTGTACATCCGGGA | 24 | 3450-3473 |
| SEQ ID NO: 98 | GAGCCATCCAAACTCTTGAGAGAG | 24 | 3486-3509 |
| SEQ ID NO: 99 | CAGTGCTTTCATGCACAGGAATTC | 24 | 35254548 |
| SEQ ID NO: 100 | ATTCGAAGTTCATCAAAGAATTTT | 24 | 3590-3613 |
| SEQ ID NO: 101 | ATCGAGTTCCTTGATGTAGTTCAT | 24 | 3612-3635 |

TABLE 1-continued

Antisense Oligonucleotide Sequences

| SEQ ID NO | Sequence (5'-3') | Length (bases) | Target site NM_000044 |
|---|---|---|---|
| SEQ ID NO: 102 | GCACTTGCACAGAGATGATCTCTG | 24 | 3805-3828 |
| SEQ ID NO: 103 | AATAGATGGGCTTGACTTTCCCAG | 24 | 3841-3864 |
| SEQ ID NO: 104 | ATAACAGGCAGAAGACATCTGAAA | 24 | 3920-3943 |
| SEQ ID NO: 105 | ATTCCCCAAGGCACTGCAGAGGAG | 24 | 3956-3979 |
| SEQ ID NO: 106 | ATGGGCTGACATTCATAGCCTTCA | 24 | 3110-3133 |

In SEQ ID NOs: 23-43, shown below in Table 2, upper case, boldface letters indicate nucleoside analogue monomers (e.g., •-D-oxy LNA monomers) and subscript "s" represents phosphorothioate linkage groups between the monomers. The absence of a subscript "s" (if any) indicates a phosphodiester linkage group. Lower case letters represent DNA monomers.

TABLE 2

Oligonucleotide designs

| SEQ ID NO | Sequence (5'-3') |
|---|---|
| SEQ ID NO: 23 | 5'-$G_sA_sG_sa_sa_sc_sc_sa_st_sc_sc_st_sc_sA_sC_s$C-3' |
| SEQ ID NO: 24 | 5'-$G_sG_sA_sc_sc_sa_sg_sg_st_sa_sg_sc_sc_sT_sG_s$T-3' |
| SEQ ID NO: 25 | 5'-$C_sC_sC_sc_st_sg_sg_sa_sc_st_sc_sa_sg_sA_sT_s$G-3' |
| SEQ ID NO: 26 | 5'-$G_sC_sA_sc_sa_sa_sg_sg_sa_sg_st_sg_sg_sG_sA_s$C-3' |
| SEQ ID NO: 27 | 5'-$G_sC_sT_sg_st_sg_sa_sa_sg_sa_sg_sa_sg_sT_sG_s$T-3' |
| SEQ ID NO: 28 | 5'-$T_sT_sT_sg_sa_sc_sa_sc_sa_sa_sg_st_sg_sG_sG_s$A-3' |
| SEQ ID NO: 29 | 5'-$G_sT_sG_sa_sc_sa_sc_sc_sc_sa_sg_sa_sa_sG_sC_s$T-3' |
| SEQ ID NO: 30 | 5'-$C_sA_sT_sc_sc_sc_st_sg_sc_st_st_sc_sa_sT_sA_s$A-3' |
| SEQ ID NO: 31 | 5'-$A_sC_sC_sa_sa_sg_st_st_st_sc_st_st_sc_sA_sG_s$C-3' |
| SEQ ID NO: 32 | 5'-$C_sT_sT_sg_sg_sc_sc_sc_sa_sc_st_st_sg_sA_sC_s$C-3' |
| SEQ ID NO: 33 | 5'-$T_sC_sC_st_sg_sg_sa_sg_sc_st_sg_sa_sc_sA_sT_s$T-3' |
| SEQ ID NO: 34 | 5'-$C_sA_sC_st_sg_sg_sc_st_sg_st_sa_sc_sa_sT_sC_s$C-3' |
| SEQ ID NO: 35 | 5'-$C_sA_sT_sc_sc_sa_sa_sa_sc_st_sc_st_sc_sG_sA_s$G-3' |
| SEQ ID NO: 36 | 5'-$G_sC_sT_st_st_sc_sa_st_sg_sc_sa_sc_sa_sG_sG_s$A-3' |
| SEQ ID NO: 37 | 5'-$G_sA_sA_sg_st_st_sc_sa_st_sc_sa_sa_sa_sG_sA_s$A-3' |
| SEQ ID NO: 38 | 5'-$A_sG_sT_st_sc_sc_st_st_sg_sa_st_sg_st_sA_sG_s$T-3' |

TABLE 2-continued

Oligonucleotide designs

| SEQ ID NO | Sequence (5'-3') |
|---|---|
| SEQ ID NO: 39 | 5'-$T_sT_sG_sc_sa_sc_sa_sg_sa_sg_sa_st_sg_sA_sT_s$C-3' |
| SEQ ID NO: 40 | 5'-$G_sA_sT_sg_sg_sg_sc_st_st_sg_sa_sc_st_sT_sT_s$C-3' |
| SEQ ID NO: 41 | 5'-$C_sA_sG_sg_sc_sa_sg_sa_sa_sg_sa_sc_sa_sT_sC_s$T-3' |
| SEQ ID NO: 42 | 5'-$C_sC_sC_sa_sa_sg_sg_sc_sa_sc_st_sg_sc_sA_sG_s$A-3' |
| SEQ ID NO: 43 | 5'-$G_sC_sT_sg_sa_sc_sa_st_st_sc_sa_st_sa_sG_sC_s$C-3' |

Example 4

In Vitro Model: Cell Culture

The effect of antisense oligonucleotides on target nucleic acid expression can be tested in any of a variety of cell types provided that the target nucleic acid is present at measurable levels. The target can be expressed endogenously or by transient or stable transfection of a nucleic acid encoding said target. The expression level of target nucleic acid can be routinely determined using, for example, Northern blot analysis, Real-Time PCR, Ribonuclease protection assays. The following cell types are provided for illustrative purposes, but other cell types can be routinely used, provided that the target is expressed in the cell type chosen.

Cells were cultured in the appropriate medium as described below and maintained at 37° C. at 95-98% humidity and 5% CO$_2$. Cells were routinely passaged 2-3 times weekly.

A549 The human lung cancer cell line A5439 was cultured in DMEM (Sigma)+10% fetal bovine serum (FBS)+2 mM Glutamax I+gentamicin (25 µg/ml).

MCF7 The human breast cancer cell line MCF7 was cultured in EagleMEM (Sigma)+10% fetal bovine serum (PBS)+2 mM Glutamax I+1×NEAA+gentamicin (25 µg/ml).

Example 5

In Vitro Model: Treatment with Antisense Oligonucleotide

The cell lines listed in Example 4 were treated with an oligomer using the cationic liposome formulation LipofectAMINE 2000 (Gibco) as transfection vehicle. Cells were seeded in 6-well cell culture plates (NUNC) and treated when 80-90% confluent. Oligomer concentrations used ranged from 1 nM to 16 nM final concentration. Formulation of oligomer-lipid complexes were carried out essentially as described by the manufacturer using serum-free OptiMEM (Gibco) and a final lipid concentration of 5 μg/mL LipofectAMINE 2000. Cells were incubated at 37° C. for 4 hours and treatment was stopped by removal of oligomer-containing culture medium. Cells were washed and serum-containing media was added. After oligomer treatment, cells were allowed to recover for 20 hours before they were harvested for RNA analysis.

Example 6

In Vitro Model: Extraction of RNA and cDNA Synthesis

Total RNA Isolation and First Strand Synthesis

Total RNA was extracted from cells transfected as described above and using the Qiagen RNeasy kit (Qiagen cat. no. 74104) according to the manufacturer's instructions. First strand synthesis was performed using Reverse Transcriptase reagents from Ambion according to the manufacturer's instructions.

For each sample, the volume of 0.5 •g total RNA was adjusted to 10.8 •l with RNase free H$_2$O and mixed with 2 •l random decamers (50 •M) and 4 •l dNTP mix (2.5 mM each dNTP) and heated to 70° C. for 3 min, after which the samples were rapidly cooled on ice. After cooling the samples on ice, 2 •l 10× Buffer RT, 1 •l MMLV Reverse Transcriptase (100 U/•l) and 0.25 •l RNase inhibitor (10 U/•l) were added to each sample, followed by incubation at 42° C. for 60 min, heat inactivation of the enzyme at 95° C. for 10 min and then cooling of the sample to 4° C.

Example 7

In Vitro Model: Analysis of Oligonucleotide Inhibition of Androgen Receptor Expression by Real-Time PCR Antisense modulation of androgen receptor expression can be assayed in a variety of ways known in the art. For example, androgen receptor mRNA levels can be quantitated by, e.g., Northern blot analysis, competitive polymerase chain reaction (PCR), or real-time PCR. Real-time quantitative PCR is presently preferred. RNA analysis can be performed on total cellular RNA or mRNA.

Methods of RNA isolation and RNA analysis such as Northern blot analysis are routine in the art and are taught in, for example, Current Protocols in Molecular Biology, John Wiley and Sons.

Real-time quantitative (PCR) can be conveniently accomplished using the commercially available Multi-Color Real Time PCR Detection System, available from Applied Biosystems.

Real-Time Quantitative PCR Analysis of Androgen Receptor mRNA Levels

The amount of human androgen receptor mRNA in the samples was quantified using the human androgen receptor ABI Prism Pre-Developed TaqMan Assay Reagents (Applied Biosystems cat. no. Hs00171172_m1) according to the manufacturer's instructions.

Glyceraldehyde-3-phosphate dehydrogenase (GAPDH) mRNA quantity was used as an endogenous control for normalizing any variance in sample preparation.

The amount of human GAPDH mRNA in the samples was quantified using the human GAPDH ABI Prism Pre-Developed TaqMan Assay Reagent (Applied Biosystems cat. no. 4310884E) according to the manufacturer's instructions.

Real-time Quantitative PCR is a technique well known in the art and is taught in for example Heid et al. Real time quantitative PCR, Genome Research (1996), 6: 986-994.

Real Time PCR

The cDNA from the first strand synthesis performed as described in Example 6 was diluted 2-20 times, and analyzed by real time quantitative PCR using Taqman 7500 FAST or 7900 FAST from Applied Biosystems. The primers and probe were mixed with 2× Taqman Fast Universal PCR master mix (2×) (Applied Biosystems Cat. #4364103) and added to 4 μl cDNA to a final volume of 10 μl. Each sample was analysed in duplicate. Standard curves were generated by assaying 2-fold dilutions of a cDNA that had been prepared on material purified from a cell line expressing the RNA of interest. Sterile H$_2$O was used instead of cDNA for the no-template control. PCR program: 95° C. for 30 seconds, followed by 40 cycles of 95° C., 3 seconds, 60° C., 20-30 seconds. Relative quantities of target mRNA were determined from the calculated Threshold cycle using the Applied Biosystems Fast System SDS Software Version 1.3.1.21. or SDS Software Version 2.3.

Example 8

Figure 2:
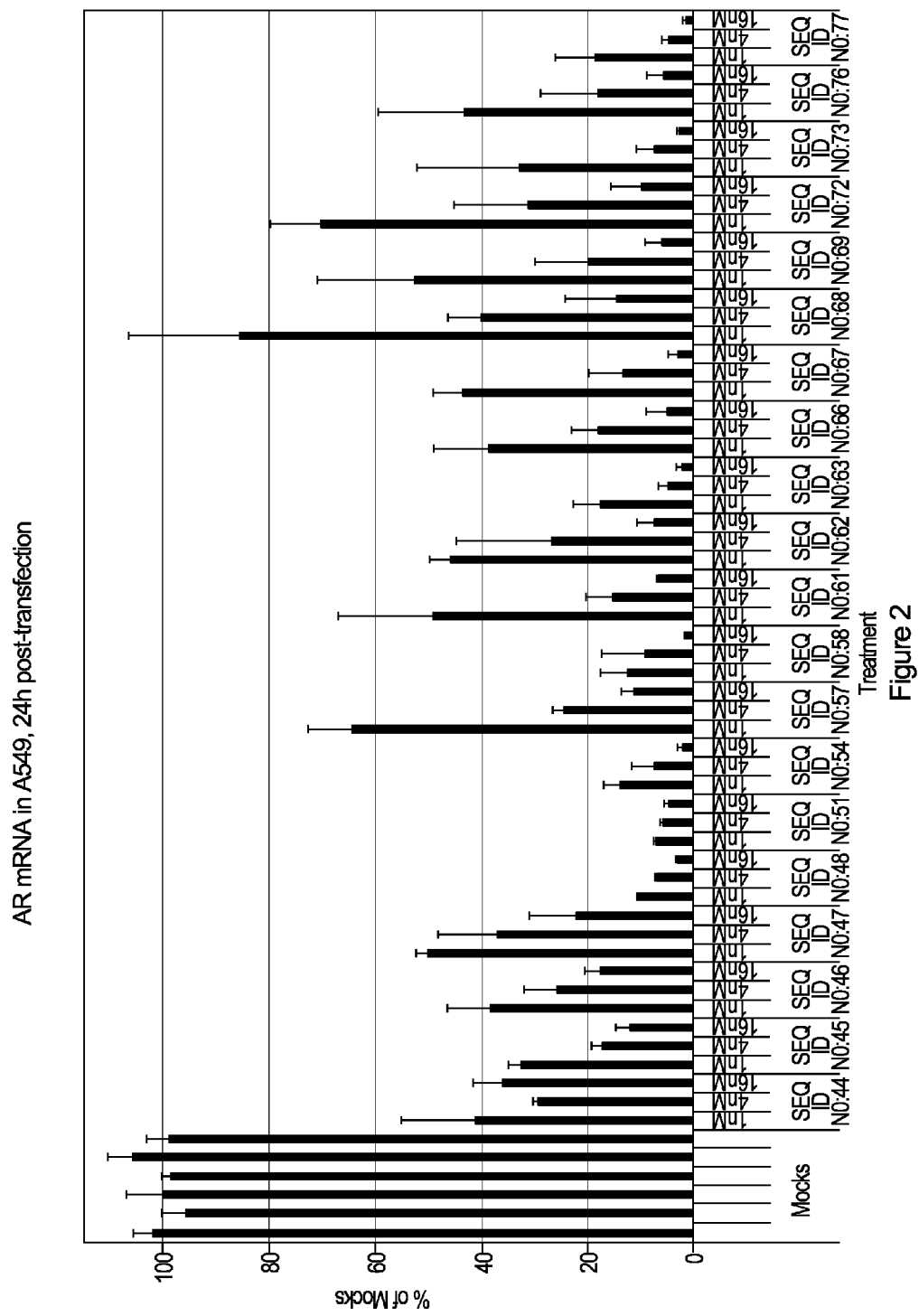
FIG. 2. Oligonucleotides presented in Table 3 were evaluated for their potential to knockdown the androgen receptor mRNA at concentrations of 1, 4 and 16 nM in A549 cells 24 hours after transfection using Real-time PCR. All results were normalised to GAPDH and inhibition of AR mRNA is shown as percent of untreated control. Results shown are an average of three independent experiments.

In Vitro Analysis: Antisense Inhibition of Human Androgen Receptor mRNA Expression by Oligonucleotide Compounds Oligonucleotides presented in Table 3 were evaluated for their potential to knock down androgen receptor mRNA expression at concentrations of 1, 4 and 16 nM (see FIGS. 1 and 2).

The data in Table 3 are presented as percentage downregulation relative to mock transfected cells at 16 nM. Lower case letters represent DNA monomers, bold, upper case letters represent β-D-oxy-LNA monomers. All cytosine bases in the LNA monomers are 5-methylcytosines. Subscript "s" represents a phosphorothioate linkage.

TABLE 3

Inhibition of human androgen receptor mRNA expression by oligonucleotides

| Test substance | Sequence (5'-3') | Percent inhibition of Androgen recpetor MCF7 | Percent inhibition of Androgen receptor A549 |
| --- | --- | --- | --- |
| SEQ ID NO: 44 | 5'-G$_s$A$_s$G$_s$a$_s$a$_s$c$_s$c$_s$a$_s$t$_s$c$_s$c$_s$t$_s$c$_s$A$_s$C$_s$C-3' | 80.1 | 63.8 |
| SEQ ID NO: 45 | 5'-G$_s$G$_s$A$_s$C$_s$c$_s$a$_s$g$_s$g$_s$t$_s$a$_s$g$_s$c$_s$c$_s$T$_s$G$_s$T-3' | 89.0 | 88.2 |

TABLE 3-continued

Inhibition of human androgen receptor mRNA expression by oligonucleotides

| Test substance | Sequence (5'-3') | Percent inhibition of Androgen recpetor MCF7 | Percent inhibition of Androgen receptor A549 |
|---|---|---|---|
| SEQ ID NO: 46 | 5'-$C_sC_sC_sc_st_sg_sg_sa_sc_st_sc_sa_sg_sA_sT_sG$-3' | 89.4 | 82.8 |
| SEQ ID NO: 47 | 5'-$G_sC_sA_sc_sa_sa_sg_sg_sa_sg_st_sg_sg_sG_sA_sC$-3' | 83.1 | 77.7 |
| SEQ ID NO: 48 | 5'-$G_sC_sT_sg_st_sg_sa_sa_sg_sa_sg_sa_sg_sT_sG_sT$-3' | 93.8 | 96.7 |
| SEQ ID NO: 49 | 5'-$C_sT_sG_st_sg_sa_sa_sg_sa_sg_sa_sg_sT_sG$-3' | n.d. | n.d. |
| SEQ ID NO: 50 | 5'-$T_sG_st_sg_sa_sa_sg_sa_sg_sa_sG_sT_s$-3' | n.d. | n.d. |
| SEQ ID NO: 51 | 5'-$T_sT_sT_sg_sa_sc_sa_sc_sa_sa_sg_st_sg_sG_sG_sA$-3' | 96.9 | 95.5 |
| SEQ ID NO: 52 | 5'-$T_sT_sG_sa_sc_sa_sc_sa_sa_sg_st_sg_sG_sG$-3' | n.d. | n.d. |
| SEQ ID NO: 53 | 5'-$T_sG_sa_sc_sa_sc_sa_sa_sg_st_sG_sG$-3' | n.d. | n.d. |
| SEQ ID NO: 54 | 5'-$G_sT_sG_sa_sc_sa_sc_sc_sc_sa_sg_sa_sa_sG_sC_sT$-3' | 95.4 | 98.3 |
| SEQ ID NO: 55 | 5'-$T_sG_sA_sc_sa_sc_sc_sc_sa_sg_sa_sa_sG_sC$-3' | n.d. | n.d. |
| SEQ ID NO: 56 | 5'-$G_sA_sc_sa_sc_sc_sc_sa_sg_sa_sA_sG$-3' | n.d. | n.d. |
| SEQ ID NO: 57 | 5'-$C_sA_sT_sc_sc_st_sg_sc_st_st_sc_sa_sT_sA_sA$-3' | 89.5 | 88.9 |
| SEQ ID NO: 58 | 5'-$A_sC_sA_sa_sa_sg_st_st_st_sc_st_st_sc_sA_sG_sC$-3' | 95.6 | 98.9 |
| SEQ ID NO: 59 | 5'-$C_sC_sA_sa_sg_st_st_st_sc_st_st_sc_sA_sG$-3' | n.d. | n.d. |
| SEQ ID NO: 60 | 5'-$C_sA_sa_sg_st_st_st_sc_st_st_sC_sA$-3' | n.d. | n.d. |
| SEQ ID NO: 61 | 5'-$C_sT_sT_sg_sg_sc_sc_sc_sa_sc_st_st_sg_sA_sC_sC$-3' | 86.7 | 93.3 |
| SEQ ID NO: 62 | 5'-$T_sC_sC_st_sg_sg_sa_sg_st_st_sg_sa_sc_sA_sT_sT$-3' | 81.3 | 93.0 |
| SEQ ID NO: 63 | 5'-$C_sA_sC_st_sg_sg_sc_st_sg_st_sa_sc_sa_sT_sC_sC$-3' | 90.9 | 98.4 |
| SEQ ID NO: 64 | 5'-$A_sC_sT_sg_sg_sc_st_sg_st_sa_sc_sa_sT_sC$-3' | n.d. | n.d. |
| SEQ ID NO: 65 | 5'-$C_sT_sg_sg_sc_st_sg_st_sa_sc_sA_sT$-3' | n.d. | n.d. |
| SEQ ID NO: 66 | 5'-$C_sA_sT_sc_sc_sa_sa_sa_sc_st_sc_st_st_sG_sA_sG$-3' | 79.8 | 95.3 |
| SEQ ID NO: 67 | 5'-$G_sC_sT_st_st_sc_sa_st_sg_sc_sa_sc_sa_sG_sG_sA$-3' | 83.5 | 97.0 |
| SEQ ID NO: 68 | 5'-$G_sA_sA_sg_st_st_sc_sa_st_sc_sa_sa_sa_sG_sA_sA$-3' | 88.2 | 85.6 |
| SEQ ID NO: 69 | 5'-$A_sG_sT_sc_sc_st_st_sg_sa_st_sg_st_sA_sG_sT$-3' | 92.7 | 94.0 |

TABLE 3-continued

Inhibition of human androgen receptor mRNA expression by oligonucleotides

| Test substance | Sequence (5'-3') | Percent inhibition of Androgen receptor MCF7 | Percent inhibition of Androgen receptor A549 |
|---|---|---|---|
| SEQ ID NO: 70 | 5'-G$_s$T$_s$T$_s$C$_s$C$_s$t$_s$t$_s$t$_s$g$_s$a$_s$t$_s$g$_s$T$_s$A$_s$G-3' | n.d. | n.d. |
| SEQ ID NO: 71 | 5'-T$_s$T$_s$C$_s$C$_s$t$_s$t$_s$g$_s$a$_s$t$_s$g$_s$T$_s$A-3' | n.d. | n.d. |
| SEQ ID NO: 72 | 5'-T$_s$T$_s$G$_s$C$_s$a$_s$C$_s$a$_s$g$_s$a$_s$g$_s$a$_s$t$_s$g$_s$A$_s$T$_s$C-3' | 79.2 | 90.4 |
| SEQ ID NO: 73 | 5'-G$_s$A$_s$T$_s$g$_s$g$_s$g$_s$C$_s$t$_s$t$_s$g$_s$a$_s$C$_s$t$_s$T$_s$T$_s$C-3' | 91.1 | 97.3 |
| SEQ ID NO: 74 | 5'-A$_s$T$_s$g$_s$g$_s$g$_s$C$_s$t$_s$t$_s$g$_s$a$_s$C$_s$t$_s$T$_s$T-3' | n.d. | n.d. |
| SEQ ID NO: 75 | 5'-T$_s$G$_s$g$_s$g$_s$C$_s$t$_s$t$_s$g$_s$a$_s$C$_s$T$_s$T-3' | n.d. | n.d. |
| SEQ ID NO: 76 | 5'-C$_s$A$_s$G$_s$g$_s$C$_s$a$_s$g$_s$a$_s$a$_s$g$_s$a$_s$C$_s$a$_s$T$_s$C$_s$T-3' | 85.9 | 94.3 |
| SEQ ID NO: 77 | 5'-C$_s$C$_s$C$_s$a$_s$a$_s$g$_s$g$_s$C$_s$a$_s$C$_s$t$_s$g$_s$C$_s$A$_s$G$_s$A-3' | 93.0 | 98.5 |
| SEQ ID NO: 78 | 5'-C$_s$C$_s$A$_s$a$_s$g$_s$g$_s$C$_s$a$_s$C$_s$t$_s$g$_s$C$_s$A$_s$G-3' | n.d. | n.d. |
| SEQ ID NO: 79 | 5'-C$_s$A$_s$a$_s$g$_s$g$_s$C$_s$a$_s$C$_s$t$_s$g$_s$C$_s$A-3' | n.d. | n.d. |
| SEQ ID NO: 80 | 5'-G$_s$C$_s$T$_s$g$_s$a$_s$C$_s$a$_s$t$_s$t$_s$C$_s$a$_s$t$_s$a$_s$G$_s$C$_s$C-3' | n.d. | n.d. |

As shown in Table 3, oligonucleotides having the sequences set forth in SEQ ID NOs: 48, 51, 54, 58, 63, 69, 73 and 77 at 16 nM demonstrated greater than 90% inhibition of androgen receptor mRNA expression in A549 and MCF7 cells in these experiments.

In certain embodiments, oligomers based on the tested antisense oligomer sequences and designs, but having, for example, different lengths (shorter or longer) and/or monomer content (e.g. the type and/or number of nucleoside analogues) than those shown, e.g., in Table 3, could also provide suitable inhibition of androgen receptor expression.

Example 9

In Vivo Analysis: Antisense Inhibition of Mouse Androgen Receptor mRNA Liver Expression by Oligonucleotide Compounds Nude mice were dosed i.v. q3dx4 with 100 mg/kg oligonucleotide (group size of 5 mice). The antisense oligonucleotides (SEQ ID:48, SEQ ID:51, SEQ ID:58, SEQ ID:63, SEQ ID:77) were dissolved in phosphate buffered saline. Animals were sacrificed 24 h after last dosing and liver tissue was sampled and stored in RNA later until RNA extraction and QPCR analysis. Total RNA was extracted and AR mRNA expression in liver samples was measured by QPCR as described, in Example 7 using a mouse AR QPCR assay (cat. Mm01238475_m1, Applied Biosystems). Results were normalised to mouse GAPDH (cat. no. 4352339E, Applied Biosystems) and knock-down was quantitated relative to saline treated controls. The data in Table 4 are presented as percentage down-regulation relative to saline treated animals.

TABLE 4

In vivo knock-down of AR mRNA expression

| Compound | Liver (% KD) |
|---|---|
| Saline | 0 |
| SEQ ID: 51 100 mg/kg | 65.0 +/− 12.6 |
| SEQ ID: 58 100 mg/kg | 95.2 +/− 1.0 |
| SEQ ID: 77 100 mg/kg | 91.9 +/− 3.9 |

As shown in Table 4, oligonucleotides of SEQ ID NOs: 58 and 77 at 100 mg/kg demonstrated greater than 90% inhibition of androgen receptor mRNA expression in mouse liver cells in these experiments.

Example 10

In Vitro Analysis: Antisense Inhibition of Human Androgen Receptor mRNA

Measurement of Proliferating Viable Cells (MTS Assay)

Figure 13:
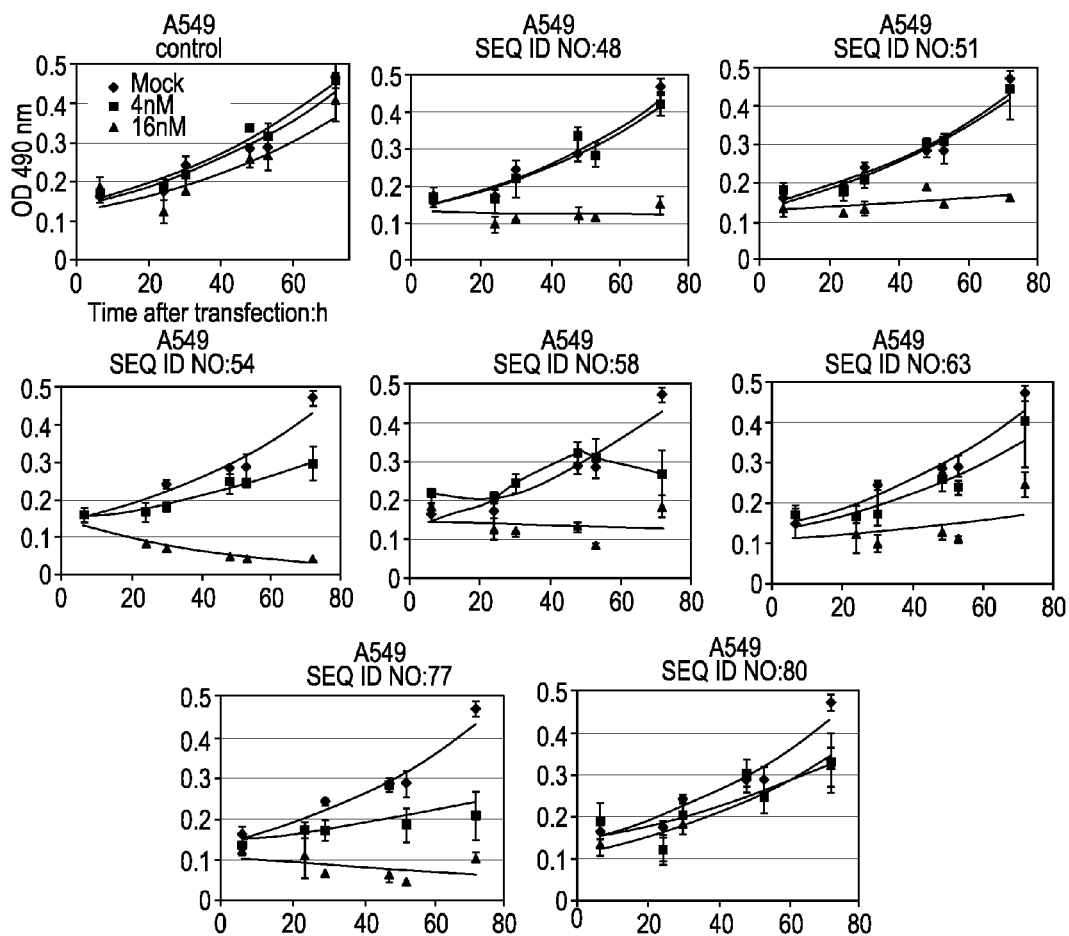
FIG. 13: Cell proliferation assay—A549, time course post-transfection
Figure 14:
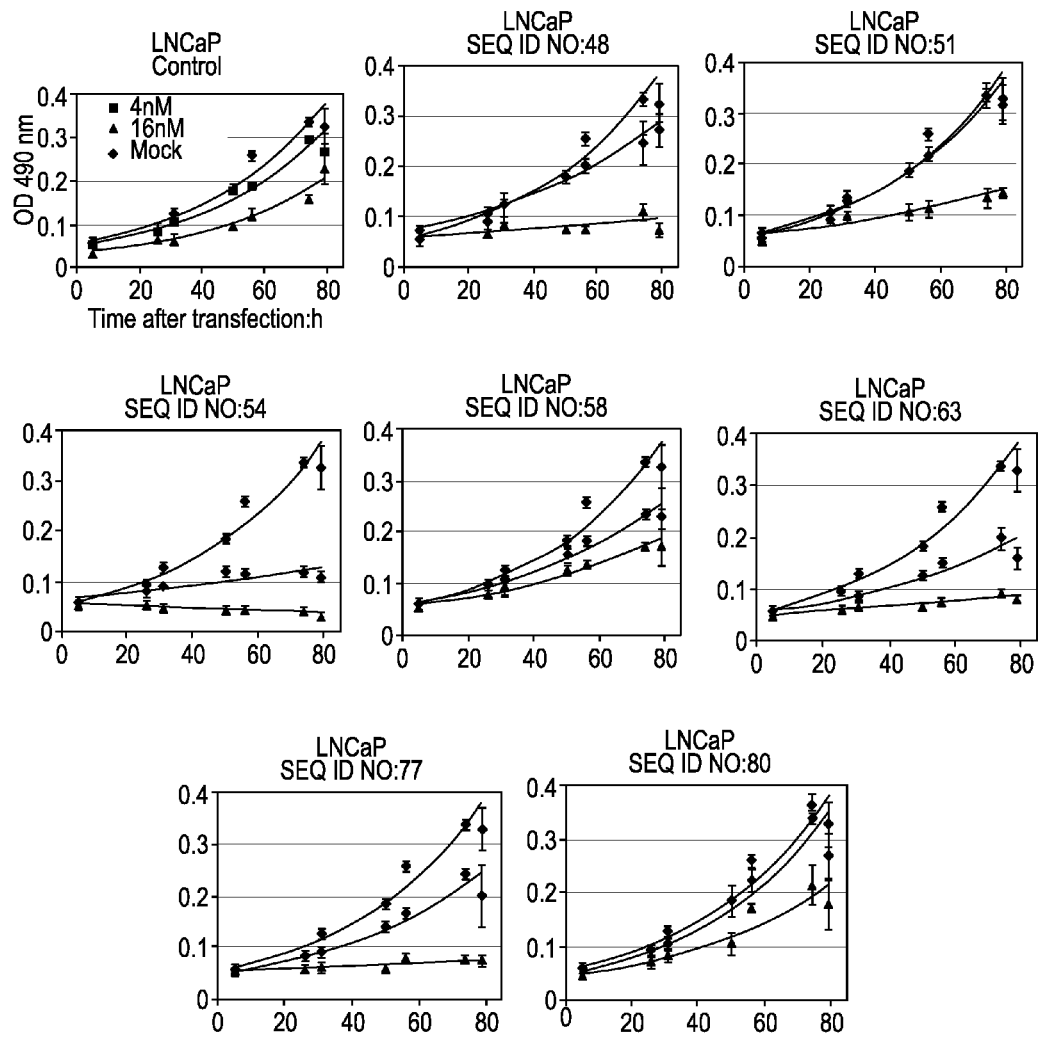
FIG. 14: Cell proliferation assay—time course post-transfection

LNCaP prostate cancer and A549 lung cancer cells were seeded to a density of 150,000 cells per well in a 6-well plate the day prior to transfection. A549 cells were cultured in DMEM (Sigma)+10% fetal bovine serum (FBS)+2 mM Glutamax I+gentamicin (25 µg/ml) whereas LNCaP cells were cultured in RPMI 1640 Medium (Sigma)+10% fetal bovine serum (FBS)+2 mM Glutamax I+gentamicin (25 µg/ml). On the following day, medium was removed followed by addition of 1.2 ml OptiMEM containing 5 µg/ml Lipofectamine-2000 (Invitrogen). Cells were incubated for 7 min before adding 0.3 ml oligonucleotides diluted in OptiMEM. The final oligonucleotide concentrations were 4 nM and 16 nM. After 4 hours of treatment, media was removed and cells were trypsinized and seeded to a density of 5000 cells per well in a clear 96 well plate (Scientific Orange no. 1472030100) in 100 μl media. Viable cells were measured at the times indicated by adding 10 μl the tetrazolium compound [3-(4,5-dimethyl-2-yl)-5-(3-carboxymethoxyphenyl)-2-(4-sulfophenyl)-2H-tetrazolium, inner salt; MTS] and an electron coupling reagent (phenazine ethosulfate; PES) (CellTiter 96® AQueous One Solution Cell Proliferation Assay, Promega). Viable cells were measured at 490 nm in a Powerwave (Biotek Instruments). The OD490 nm measurements were plotted against time/h. (See FIG. 13 and FIG. 14). As shown in FIG. 13 and FIG. 14, oligonucleotides of SEQ ID NOs: 58 and 77 inhibit growth of both LNCaP prostate and A549 lung cancer cells.

Example 11

Figure 15:
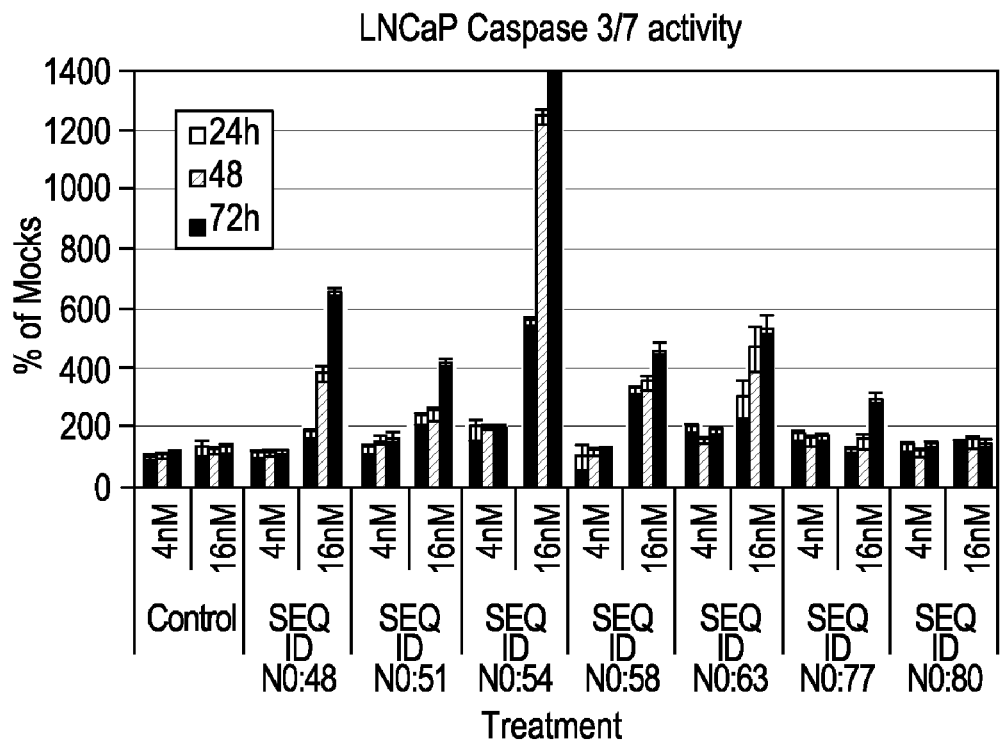
FIG. 15: Caspase 3/7 activity in LNCaP cells, 24, 48 or 72 hours post-transfection.
Figure 16:
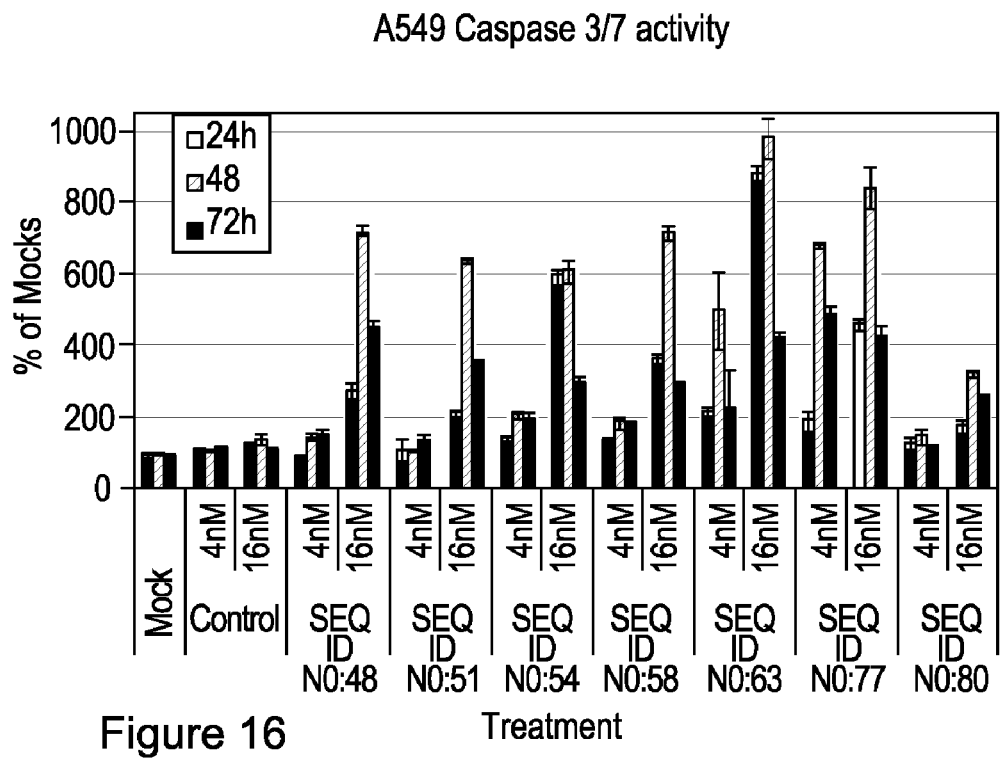
FIG. 16: Caspase 3/7 activity in A549 cells, 24, 48 or 72 hours post-transfection.

In Vitro Analysis: Caspase 3/7 Activity by Antisense Inhibition of Hunan Androgen Receptor mRNA LNCaP prostate cancer cells and A549 lung cancer cells were seeded to a density of 150,000 cells per well in a 6-well plate the day prior to transfection. A549 cells were cultured in DMEM (Sigma)+10% fetal bovine serum (FBS)+2 mM Glutamax I+gentamicin (25 μg/ml) whereas LNCaP cells were cultured in RPMI 1640 Medium (Sigma)+10% fetal bovine serum (PBS)+2 mM Glutamax I+gentamicin (25 μg/ml). The next day medium was removed followed by addition of 1.2 ml OptiMEM containing 5 μg/ml Lipofectamine2000 (Invitrogen). Cells were incubated for 7 min before adding 0.3 ml oligonucleotides diluted in OptiMEM. The final oligonucleotide concentrations were 4 nM and 16 nM. After 4 hours of treatment, media was removed and cells were trypsinized and seeded to a density of 5000 cells per well in a white 96 well plate (Nunc) in 100 μl media. Caspase 3/7 activity was measured at the times indicated by adding 100 μl Caspase-Glo 3/7 assay (Promega). Caspase 3/7 activity was measured using a luminometer. The caspase 3/7 activities were measured at three different time points 14 h, 48 h and 72 h (See FIG. 15 and FIG. 16). As shown in FIG. 15 and FIG. 16, oligonucleotides of SEQ ID NOs: 58 and 77 induce caspase 3/7 activity in both LNCaP prostate and A549 lung cancer cells.

Example 12

In Vitro Analysis: Antisense Inhibition of Human Androgen Receptor mRNA Expression by Oligonucleotide Compounds in Prostate Cancer Cell Line LNCaP and Lung Cancer Cell Line A549

Figure 11:
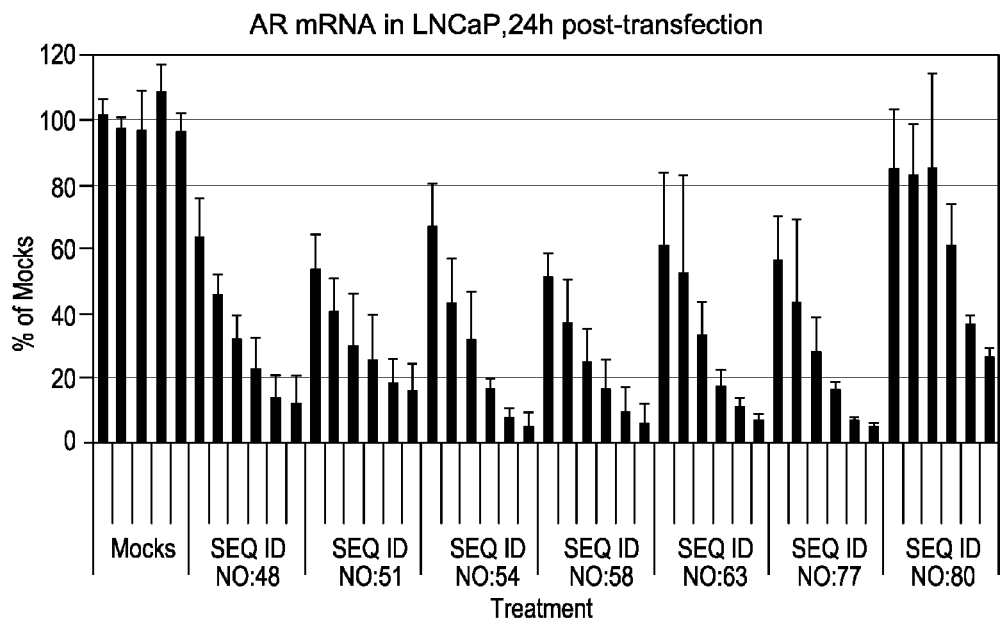
FIG. 11: AR mRNA in LNCaP, 24 h post-transfection
Figure 12:
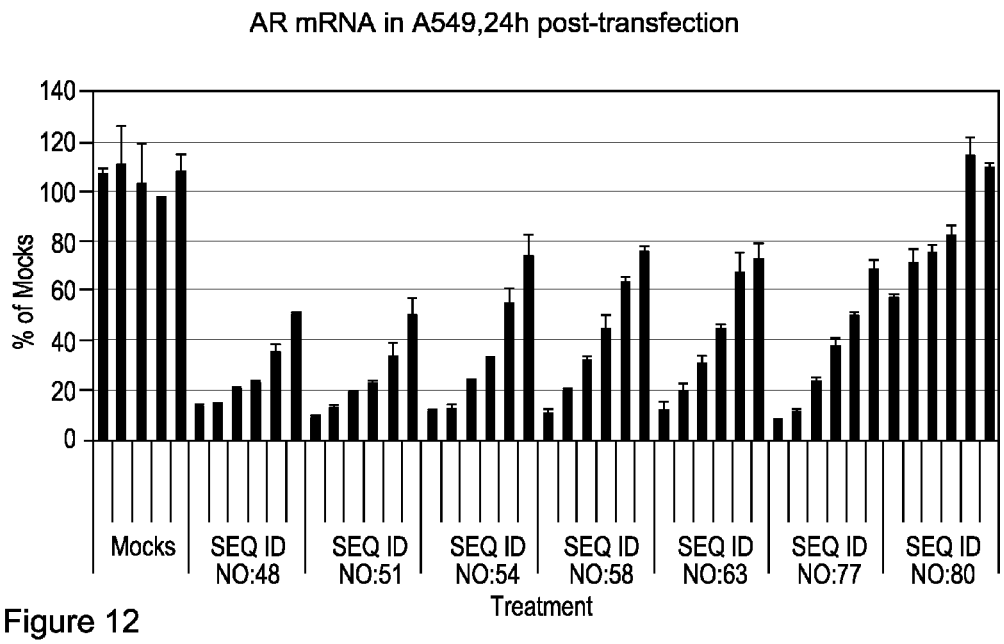
FIG. 12: AR mRNA in A549, 24 h post-transfection

Oligonucleotides were evaluated for their potential to knock down androgen receptor mRNA expression at concentrations of 0.5, 1, 2, 4, 8 and 16 nM (see FIG. 11). LNCaP prostate cancer cells and A549 lung cancer cells were seeded to a density of 150,000 cells per well in a 6-well plate the day prior to transfection. A549 cells were cultured in DMEM (Sigma)+10% fetal bovine serum (FBS)+2 mM Glutamax I+gentamicin (25 μg/ml). LNCaP cells were cultured in RPMI 1640 Medium (Sigma)+10% fetal bovine serum (FBS)+2 mM Glutamax I+gentamicin (25 μg/ml). On the following day, medium was removed followed by addition of 1.2 ml OptiMEM containing 5 μg/ml Lipofectamine2000 (Invitrogen). Cells were incubated for 7 min before adding 0.3 ml oligonucleotides diluted in OptiMEM. The final oligonucleotide concentrations were 0.5, 1, 2, 4, 8 and 16 nM. Cells were washed and serum-containing media was added. After oligomer treatment cells were allowed to recover for 20 hours before they were harvested for RNA analysis. The procedure for RNA isolation, cDNA synthesis and qPCR were as described in Examples 5, 6 and 7. As shown in FIGS. 11 and 12 oligonucleotides of SEQ ID NOs: 58 and 77 were potent in knocking down AR mRNA expression in both the lung cancer cell line A549 and in the androgen receptor-dependent LNCaP prostate cancer cell line.

Example 13

Figure 17:
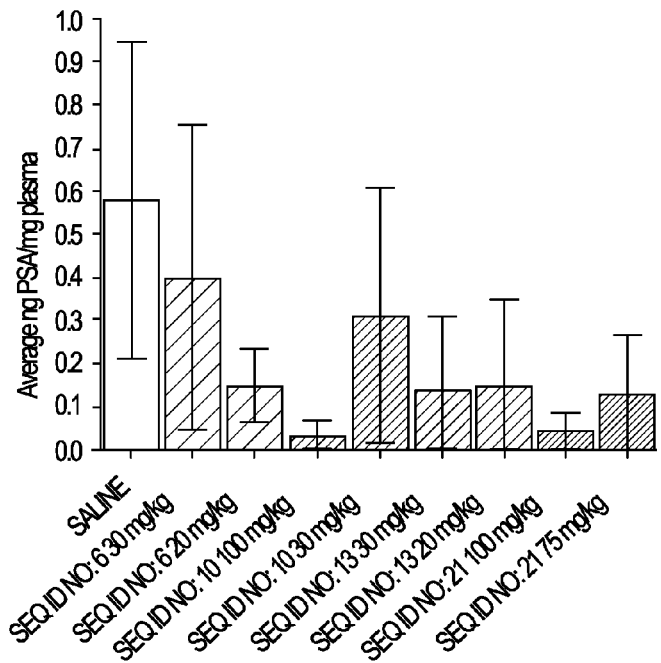
FIG. 17: Average PSA in plasma after in vivo oligomer treatment.

In Vivo Analysis: Effect of Antisense Oligonucleotides on PSA Levels and Androgen-Dependent Prostate Tumor Growth in Mice Six to seven week old male athymic nu/nu mice (Harlan Sprague Dawley) weighing an average of 27.3±2.4 g were used in the study. Ten million cells of 22RV1 (androgen-independent prostate cancer line) were suspended in PBS (Gibco#14190) and Matrigel (BD#356234) with a ratio of 1:1 were injected subcutaneously into each mouse. When tumors reached an average volume of 150-200 mm$^3$, the mice were divided into nine experimental groups. Two hundred μl of oligomer were injected intravenously when the average tumor size reached 152.66±27.97 mm$^3$. Oligomers were given every 3 days for a total of 5 dosings. The control vehicles were given using the same dosing regimen as the oligomers. On day 16, mice were sacrificed and blood collected in EDTA laced tubes and spun for 5 min. 50 μl of the supernatants were then subjected to PSA assay using the ELISA kit from ALPCO Diagnostics in Salem (PSAHU-L01). Results of the experiment are shown in FIG. 17.

Figure 18:
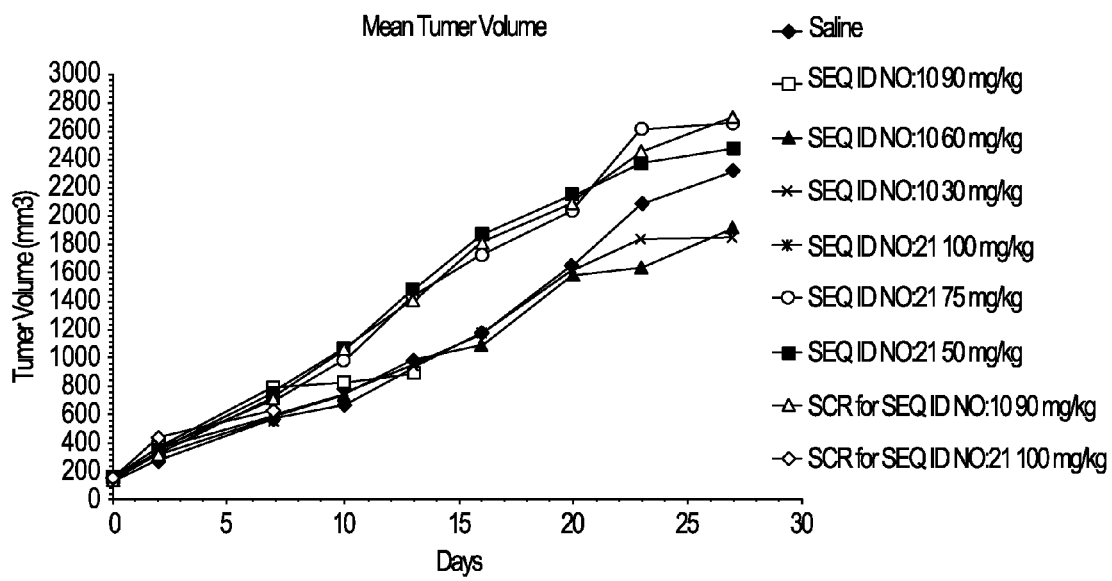
FIG. 18: In vivo inhibition of tumor growth

Six to seven week old male athymic nu/nu mice (Harlan Sprague Dawley) weighing an average of 27.3±2.4 g were used in the study. Ten million cells of 22RV1 (androgen-independent prostate cancer line) were suspended in PBS (Gibco#14190) and Matrigel (BD#356234) with a ratio of 1:1 were injected subcutaneously into each mouse. When tumors reached an average volume of 150-200 mm$^3$, the mice were divided into nine experimental groups. Two hundred μl of oligomer was injected intravenously when the average tumor size reached 152.66±27.97 mm$^3$. Oligomers were given every 3 days for a total of 5 dosings. The control vehicles were given using the same dosing regimen as the oligomers. The tumor volumes for each mouse were determined by measuring two dimensions with calipers and calculated using the formula: tumor volume=(length×width$^2$)/2). Results of the experiment are shown in FIG. 18.

Example 14

Preparation of Conjugates of Oligomers with Polyethylene Glycol

The oligomers having sequences shown as SEQ ID NO: 48 or SEQ ID NO: 63 are functionalized on the 5' terminus by attaching an aminoalkyl group, such as hexan-1-amine blocked with a blocking group such as Fmoc to the 5' phosphate groups of the oligomers using routine phosphoramidite chemistry, oxidizing the resultant compounds, deprotecting them and purifying them to achieve the functionalized oligomers, respectively, having the formulas (IA) and (IB):

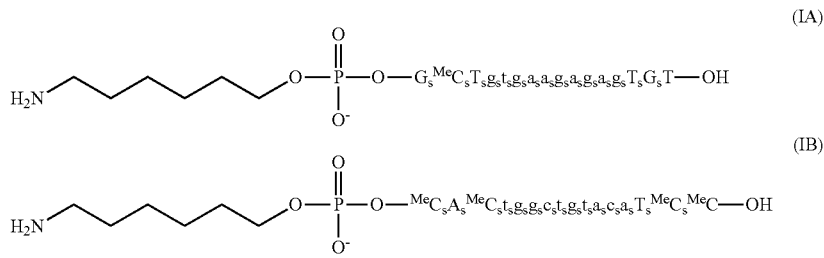

(IA)

(IB)

wherein the bold uppercase letters represent nucleoside analogue monomers, lowercase letters represent DNA monomers, the subscript "s" represents a phosphorothioate linkage, and $^{Me}C$ represents 5-methylcytosine.

A solution of activated PEG, such as the one shown in formula (II):

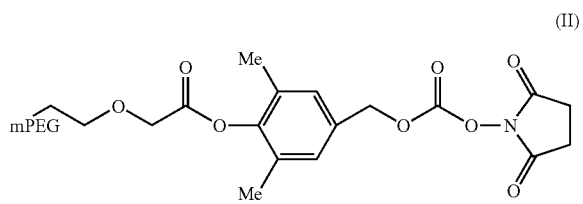

(II)

wherein the PEG moiety has an average molecular weight of 12,000, and each of the compounds of formulas (IA) and (IB) in PBS buffer are stirred in separate vessels at room temperature for 12 hours. The reaction solutions are extracted three times with methylene chloride and the combined organic layers are dried over magnesium sulphate and filtered and the solvent is evaporated under reduced pressure. The resulting residues are dissolved in double distilled water and loaded onto an anion exchange column. Unreacted PEG linker is eluted with water and the products are eluted with $NH_4HCO_3$ solution. Fractions containing pure products are pooled and lypophilized to yield the conjugates SEQ ID NOs: 48 and 63, respectively as show in formulas (IIIA) and (IIIB):

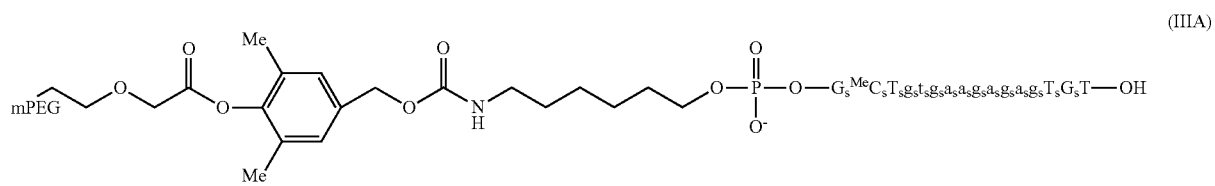

(IIIA)

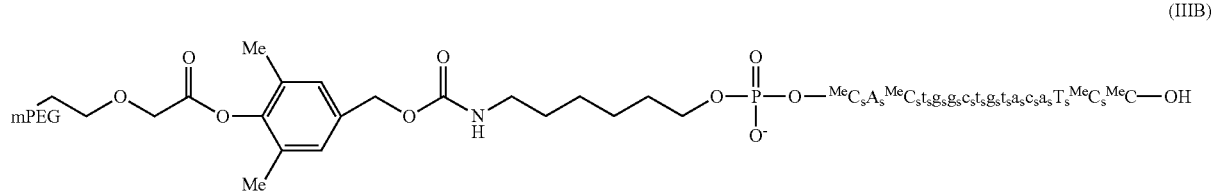

(IIIB)

wherein each of the oligomers of SEQ ID NOs: 48 and 63 is attached to a PEG polymer having average molecular weight of 12,000 via a releasable linker.

Chemical structures of PEG polymer conjugates that can be made with oligomers having sequences shown in SEQ NOs: 51, 58 and 77 using the process described above are respectively shown in formulas (IVA), (IVB) and (IVC):

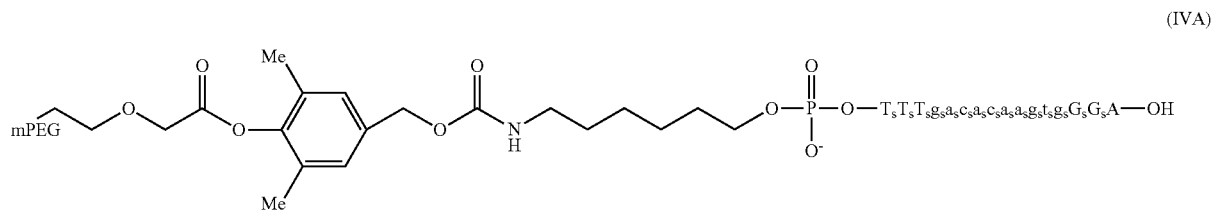

(IVA)

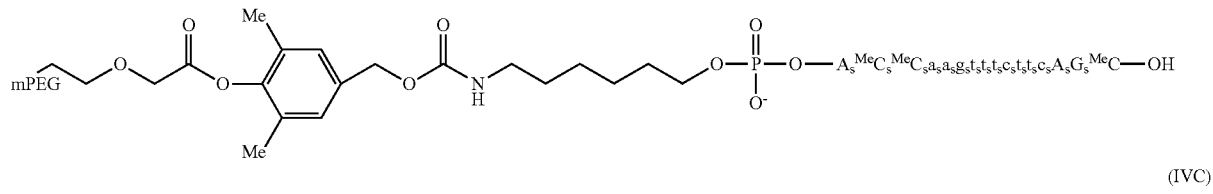

(IVB)

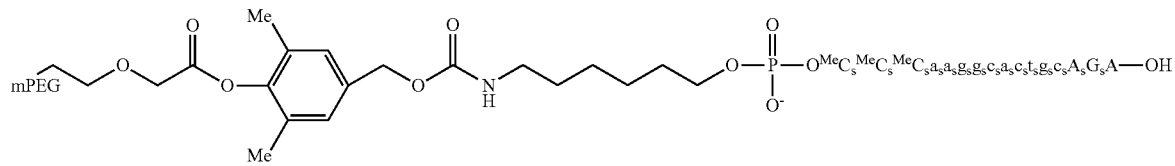

(IVC)

wherein bold uppercase letters represent beta-D-oxy-LNA monomers, lowercase letters represent DNA monomers, the subscript "s" represents a phosphorothioate linkage and $^{Me}C$ represent 5-methylcytosine.

Activated oligomers that can be used in this process to respectively make the conjugates shown in formulas (NA), (IVB) and (IVC) have the chemical structures shown in formulas (VA), (VB) and (VC):

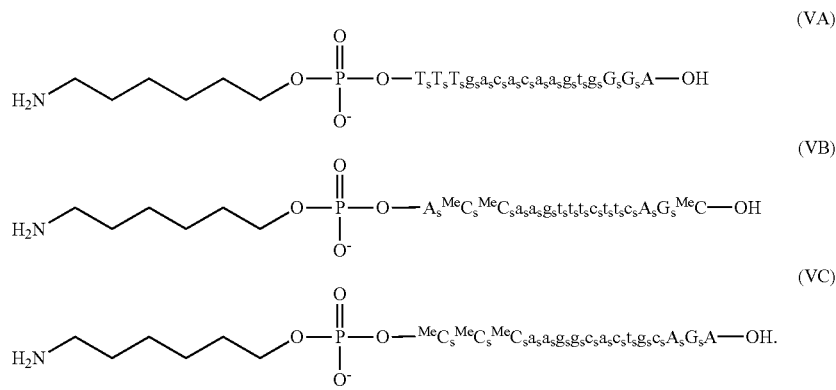

We claim:

1. An oligomer consisting of the formula:

$$5'\text{-}^{Me}C_s{}^{Me}C_s{}^{Me}C_s a_s a_s g_s g_s c_s a_s c_s t_s g_s c_s A_s G_s A\text{-}3' \quad (\text{SEQ ID NO: 77}),$$

wherein uppercase letters denote beta-D-oxy-LNA monomers and lowercase letters denote DNA monomers, the subscript "s" denotes a phosphorothioate linkage, and $^{Me}C$ denotes a beta-D-oxy-LNA monomer containing a 5-methylcytosine base.

2. A conjugate comprising the oligomer of claim 1, covalently attached to at least one moiety that is not a nucleic acid or a monomer.

3. A pharmaceutical composition comprising:
   the oligomer of claim 1 or a conjugate comprising said oligomer covalently attached to at least one moiety that is not a nucleic acid or a monomer; and
   a pharmaceutically acceptable diluent, carrier, salt or adjuvant.

4. A method of inhibiting the expression of androgen receptor in a cell, comprising:
   contacting said cell with an effective amount of the oligomer of claim 1.

5. A method of inhibiting the expression of androgen receptor in a cell, comprising:
   contacting said cell with an effective amount of a conjugate according to claim 2.

6. A method of inhibiting the expression of androgen receptor in a tissue of a mammal, comprising:
   contacting said tissue with an effective amount of the oligomer of claim 1.

7. A method of inhibiting the expression of androgen receptor in a tissue of a mammal comprising:
   contacting said tissue with an effective amount of a conjugate according to claim 2.

8. A method of inhibiting the expression of an androgen receptor target gene in a cell or tissue of a mammal, comprising:
   contacting said cell or tissue with an effective amount of the oligomer of claim 1.

9. A method of treating a cancer in a mammal comprising administering to said mammal an effective amount of the oligomer of claim 1, wherein the cancer is selected from the group consisting of breast cancer and prostate cancer.

10. An activated oligomer comprising:
    the oligomer of claim 1; and
    at least one functional group covalently attached thereto at one or more positions independently selected from the 5'-end, the 3' end, the 2'-OH of a ribose sugar, and the base.

* * * * *

SEQUENCE LISTING

```
<160> NUMBER OF SEQ ID NOS: 106

<210> SEQ ID NO 1
<211> LENGTH: 4314
<212> TYPE: DNA
<213> ORGANISM: homo sapiens

<400> SEQUENCE: 1
cgagatcccg gggagccagc ttgctgggag agcgggacgg tccggagcaa gcccagaggc      60
agaggaggcg acagagggaa aaagggccga gctagccgct ccagtgctgt acaggagccg     120
aagggacgca ccacgccagc cccagcccgg ctccagcgac agccaacgcc tcttgcagcg     180
cggcggcttc gaagccgccg cccggagctg cccctttcctc ttcggtgaag tttttaaaag     240
ctgctaaaga ctcggaggaa gcaaggaaag tgcctggtag gactgacggc tgcctttgtc     300
ctcctcctct ccacccccgcc tcccccacc ctgccttccc ccctccccc gtcttctctc      360 ccgcagctgc ctcagtcggc tactctcagc caacccccct caccacccctt ctccccaccc    420 gcccccccgc ccccgtcggc ccagcgctgc cagcccgagt ttgcagagag gtaactccct    480
ttggctgcga gcgggcgagc tagctgcaca ttgcaaagaa ggctcttagg agccaggcga    540
```

```
ctggggagcg gcttcagcac tgcagccacg acccgcctgg ttaggctgca cgcggagaga    600
accctctgtt ttcccccact ctctctccac ctcctcctgc cttccccacc ccgagtgcgg    660
agccagagat caaagatgaa aaggcagtc aggtcttcag tagccaaaaa acaaaacaaa     720 caaaacaaa aaagccgaaa taaagaaaa agataataac tcagttctta tttgcaccta     780
cttcagtgga cactgaattt ggaaggtgga ggattttgtt ttttctttt aagatctggg     840 catcttttga atctacccct caagtattaa gagacagact gtgagcctag cagggcagat    900
cttgtccacc gtgtgtcttc ttctgcacga gactttgagg ctgtcagagc gcttttgcg     960 tggttgctcc cgcaagtttc cttctctgga gcttcccgca ggtgggcagc tagctgcagc   1020
gactaccgca tcatcacagc ctgttgaact cttctgagca agagaagggg aggcggggta   1080
agggaagtag gtggaagatt cagccaagct caaggatgga agtgcagtta gggctgggaa   1140
gggtctaccc tcggccgccg tccaagacct accgaggagc tttcagaat ctgttccaga    1200 gcgtgcgcga agtgatccag aacccgggcc ccaggcaccc agaggccgcg agcgcagcac   1260
ctcccggcgc cagtttgctg ctgctgcagc agcagcagca gcagcagcag cagcagcagc   1320
agcagcagca gcagcagcag cagcagcagc agcaagagac tagccccagg cagcagcagc   1380
agcagcaggg tgaggatggt tctccccaag cccatcgtag aggccccaca ggctacctgg   1440
tcctggatga ggaacagcaa ccttcacagc cgcagtcggc cctggagtgc caccccgaga   1500
gaggttgcgt cccagagcct ggagccgccg tggccgccag caaggggctg ccgcagcagc   1560
tgccagcacc tccggacgag gatgactcag ctgccccatc cacgttgtcc ctgctgggcc   1620
ccacttcccc cggcttaagc agctgctccg ctgaccttaa agacatcctg agcgaggcca   1680
gcaccatgca actccttcag caacagcagc aggaagcagt atccgaaggc agcagcagcg   1740
ggagagcgag ggaggcctcg ggggctccca cttcctccaa ggacaattac ttaggggca    1800 cttcgaccat ttctgacaac gccaaggagt tgtgtaaggc agtgtcggtg tccatgggcc   1860
tgggtgtgga ggcgttggag catctgagtc caggggaaca gcttcggggg gattgcatgt   1920
acgccccact tttgggagtt ccacccgctg tgcgtcccac tccttgtgcc ccattggccg   1980
aatgcaaagg ttctctgcta gacgacagcg caggcaagag cactgaagat actgctgagt   2040
attcccsttt caagggaggt tacaccaaag gctagaagg cgagagccta ggctgctctg    2100
gcagcgctgc agcagggagc tccggacac ttgaactgcc gtctaccctg tctctctaca    2160
agtccggagc actggacgag gcagctgcgt accagagtcg cgactactac aactttccac   2220
tggctctggc cggaccgccg cccctccgc cgcctcccca tccccacgct cgcatcaagc    2280
tggagaaccc gctggactac ggcagcgcct gggcggctgc ggcggcgcag tgccgctatg   2340
gggacctggc gagcctgcat ggcgcgggtg cagcgggacc cggttctggg tcaccctcag   2400
ccgccgcttc ctcatcctgg cacactctct tcacagccga agaaggccag ttgtatggac   2460
cgtgtggtgg tggtggggt ggtggcggcg gcggcggcg cggcggcggc ggcggcggcg    2520
gcggcggcgg cggcgaggcg ggagctgtag cccctacgg ctacactcgg ccccctcagg    2580
ggctggcggg ccaggaaagc gacttcaccg cacctgatgt gtggtaccct gcggcatgg    2640 tgagcagagt gccctatccc agtcccactt gtgtcaaaag cgaaatgggc ccctggatgg   2700
atagctactc cggaccttac ggggacatgc gtttggagac tgccagggac catgttttgc   2760
ccattgacta ttactttcca ccccagaaga cctgcctgat ctgtggagat gaagcttctg   2820
ggtgtcacta tggagctctc acatgtggaa gctgcaaggt cttcttcaaa agagccgctg   2880
aagggaaaca gaagtacctg tgcgccagca gaaatgattg cactattgat aaattccgaa   2940
```

```
ggaaaaattg tccatcttgt cgtcttcgga aatgttatga agcagggatg actctgggag    3000
cccggaagct gaagaaactt ggtaatctga aactacagga ggaaggagag gcttccagca    3060
ccaccagccc cactgaggag acaacccaga agctgacagt gtcacacatt gaaggctatg    3120
aatgtcagcc catctttctg aatgtcctgg aagccattga gccaggtgta gtgtgtgctg    3180
gacacgacaa caaccagccc gactcctttg cagccttgct ctctagcctc aatgaactgg    3240
gagagagaca gcttgtacac gtggtcaagt gggccaaggc cttgcctggc ttccgcaact    3300
tacacgtgga cgaccagatg gctgtcattc agtactcctg gatggggctc atggtgtttg    3360
ccatgggctg gcgatccttc accaatgtca actccaggat gctctacttc gcccctgatc    3420
tggttttcaa tgagtaccgc atgcacaagt cccggatgta cagccagtgt gtccgaatga    3480
ggcacctctc tcaagagttt ggatggctcc aaatcacccc ccaggaattc ctgtgcatga    3540
aagcactgct actcttcagc attattccag tggatgggct gaaaaatcaa aaattctttg    3600
atgaacttcg aatgaactac atcaaggaac tcgatcgtat cattgcatgc aaaagaaaaa    3660
atcccacatc ctgctcaaga cgcttctacc agctcaccaa gctcctggac tccgtgcagc    3720
ctattgcgag agagctgcat cagttcactt ttgacctgct aatcaagtca cacatggtga    3780
gcgtggactt tccggaaatg atggcagaga tcatctctgt gcaagtgccc aagatccttt    3840
ctgggaaagt caagcccatc tatttccaca cccagtgaag cattgaaaac cctatttccc    3900
caccccagct catgccccct ttcagatgtc ttctgcctgt tataactctg cactactcct    3960
ctgcagtgcc ttggggaatt tcctctattg atgtacagtc tgtcatgaac atgttcctga    4020
attctatttg ctgggctttt ttttttctctt tctctccttt cttttttcttc ttccctccct    4080 atctaaccct cccatggcac cttcagactt tgcttcccat tgtggctcct atctgtgttt    4140
tgaatggtgt tgtatgcctt taaatctgtg atgatcctca tatggcccag tgtcaagttg    4200
tgcttgttta cagcactact ctgtgccagc cacacaaacg tttacttatc ttatgccacg    4260
ggaagtttag agagctaaga ttatctgggg aaatcaaaac aaaaacaagc aaac          4314
```

<210> SEQ ID NO 2
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 2
gagaaccatc ctcacc                                                      16

<210> SEQ ID NO 3
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 3
ggaccaggta gcctgt                                                      16

```
<210> SEQ ID NO 4
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 4
cccctggact cagatg                                                        16

<210> SEQ ID NO 5
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 5
gcacaaggag tgggac                                                        16

<210> SEQ ID NO 6
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 6
gctgtgaaga gagtgt                                                        16

<210> SEQ ID NO 7
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 7
tttgacacaa gtggga                                                        16

<210> SEQ ID NO 8
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
```

-continued phosphorothioate

<400> SEQUENCE: 8
gtgacaccca gaagct                                               16

<210> SEQ ID NO 9
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 9
catccctgct tcataa                                               16

<210> SEQ ID NO 10
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 10
accaagtttc ttcagc                                               16

<210> SEQ ID NO 11
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 11
cttggcccac ttgacc                                               16

<210> SEQ ID NO 12
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 12
tcctggagtt gacatt                                               16

<210> SEQ ID NO 13
<211> LENGTH: 16
<212> TYPE: DNA
<213> ORGANISM: artificial
<220> FEATURE:

```
<221> NAME/KEY: misc_feature
<222> LOCATION: (1)..(16)
<223> OTHER INFORMATION: nucleotide or nucleotide analogues - optionally
      phosphorothioate

<400> SEQUENCE: 13
cactggctgt acatcc                                                     16

<210> SEQ ID NO 14
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 14
catccaaact cttgag                                                     16

<210> SEQ ID NO 15
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 15
gctttcatgc acagga                                                     16

<210> SEQ ID NO 16
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 16
gaagttcatc aaagaa                                                     16

<210> SEQ ID NO 17
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 17
agttccttga tgtagt                                                     16

<210> SEQ ID NO 18
<211> LENGTH: 16
```

```
<212> TYPE: DNA
<213> ORGANISM: artificial
<220> FEATURE:
<223> OTHER INFORMATION: LNA oligomer Sequence/oligomer Sequence motif

<400> SEQUENCE: 18
ttgcacagag atgatc                                                            16

<210> SEQ ID NO 19
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 19
gatgggcttg actttc                                                            16

<210> SEQ ID NO 20
<211> LENGTH: 16
<212> TYPE: DNA
<213> ORGANISM: artificial
<220> FEATURE:
<223> OTHER INFORMATION: LNA oligomer Sequence/oligomer Sequence motif

<400> SEQUENCE: 20
caggcagaag acatct                                                            16

<210> SEQ ID NO 21
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 21
cccaaggcac tgcaga                                                            16

<210> SEQ ID NO 22
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 22
gctgacattc atagcc                                                            16

<210> SEQ ID NO 23
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
```

```
<221> NAME/KEY: misc_feature
<222> LOCATION: (1)..(16)
<223> OTHER INFORMATION: 3-10-3 Gapmer - optionally phosphorothioate

<400> SEQUENCE: 23
gagaaccatc ctcacc                                                    16

<210> SEQ ID NO 24
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 24
ggaccaggta gcctgt                                                    16

<210> SEQ ID NO 25
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 25
cccctggact cagatg                                                    16

<210> SEQ ID NO 26
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 26
gcacaaggag tgggac                                                    16

<210> SEQ ID NO 27
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 27
gctgtgaaga gagtgt                                                    16

<210> SEQ ID NO 28
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
```

```
<221> NAME/KEY: misc_feature
<222> LOCATION: (1)..(16)
<223> OTHER INFORMATION: 3-10-3 Gapmer - optionally phosphorothioate

<400> SEQUENCE: 28
tttgacacaa gtggga                                                    16

<210> SEQ ID NO 29
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 29
gtgacaccca gaagct                                                    16

<210> SEQ ID NO 30
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 30
catccctgct tcataa                                                    16

<210> SEQ ID NO 31
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 31
accaagtttc ttcagc                                                    16

<210> SEQ ID NO 32
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 32
cttggcccac ttgacc                                                    16

<210> SEQ ID NO 33
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
```

```
<221> NAME/KEY: misc_feature
<222> LOCATION: (1)..(16)
<223> OTHER INFORMATION: 3-10-3 Gapmer - optionally phosphorothioate

<400> SEQUENCE: 33
tcctggagtt gacatt                                                          16

<210> SEQ ID NO 34
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 34
cactggctgt acatcc                                                          16

<210> SEQ ID NO 35
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 35
catccaaact cttgag                                                          16

<210> SEQ ID NO 36
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 36
gctttcatgc acagga                                                          16

<210> SEQ ID NO 37
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 37
gaagttcatc aaagaa                                                          16

<210> SEQ ID NO 38
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
```

```
<221> NAME/KEY: misc_feature
<222> LOCATION: (1)..(16)
<223> OTHER INFORMATION: 3-10-3 Gapmer - optionally phosphorothioate

<400> SEQUENCE: 38
agttccttga tgtagt                                                        16

<210> SEQ ID NO 39
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 39
ttgcacagag atgatc                                                        16

<210> SEQ ID NO 40
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 40
gatgggcttg actttc                                                        16

<210> SEQ ID NO 41
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 41
caggcagaag acatct                                                        16

<210> SEQ ID NO 42
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 42
cccaaggcac tgcaga                                                        16

<210> SEQ ID NO 43
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
```

```
<221> NAME/KEY: misc_feature
<222> LOCATION: (1)..(16)
<223> OTHER INFORMATION: 3-10-3 Gapmer - optionally phosphorothioate

<400> SEQUENCE: 43
gctgacattc atagcc                                                     16

<210> SEQ ID NO 44
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 44
gagaaccatc ctcacc                                                     16

<210> SEQ ID NO 45
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 45
ggaccaggta gcctgt                                                     16

<210> SEQ ID NO 46
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 46
cccctggact cagatg                                                     16

<210> SEQ ID NO 47
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 47
gcacaaggag tgggac                                                     16

<210> SEQ ID NO 48
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
```

```
<221> NAME/KEY: misc_feature
<222> LOCATION: (1)..(16)
<223> OTHER INFORMATION: 3-10-3 LNA Gapmer - fully phosphorothioate

<400> SEQUENCE: 48
gctgtgaaga gagtgt                                                     16

<210> SEQ ID NO 49
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 49
ctgtgaagag agtg                                                       14

<210> SEQ ID NO 50
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 50
tgtgaagaga gt                                                         12

<210> SEQ ID NO 51
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 51
tttgacacaa gtggga                                                     16

<210> SEQ ID NO 52
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 52
ttgacacaag tggg                                                       14

<210> SEQ ID NO 53
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
```

```
<221> NAME/KEY: misc_feature
<222> LOCATION: (1)..(12)
<223> OTHER INFORMATION: 2-8-2 LNA Gapmer - fully phosphorothioate

<400> SEQUENCE: 53
tgacacaagt gg                                                          12

<210> SEQ ID NO 54
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 54
gtgacaccca gaagct                                                      16

<210> SEQ ID NO 55
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 55
tgacacccag aagc                                                        14

<210> SEQ ID NO 56
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 56
gacacccaga ag                                                          12

<210> SEQ ID NO 57
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 57
catccctgct tcataa                                                      16

<210> SEQ ID NO 58
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
```

```
<221> NAME/KEY: misc_feature
<222> LOCATION: (1)..(16)
<223> OTHER INFORMATION: 3-10-3 LNA Gapmer - fully phosphorothioate

<400> SEQUENCE: 58
accaagtttc ttcagc                                                    16

<210> SEQ ID NO 59
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 59
ccaagtttct tcag                                                      14

<210> SEQ ID NO 60
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 60
caagtttctt ca                                                        12

<210> SEQ ID NO 61
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 61
cttggcccac ttgacc                                                    16

<210> SEQ ID NO 62
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 62
tcctggagtt gacatt                                                    16

<210> SEQ ID NO 63
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
```

```
<221> NAME/KEY: misc_feature
<222> LOCATION: (1)..(16)
<223> OTHER INFORMATION: 3-10-3 LNA Gapmer - fully phosphorothioate

<400> SEQUENCE: 63
cactggctgt acatcc                                                    16

<210> SEQ ID NO 64
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 64
actggctgta catc                                                      14

<210> SEQ ID NO 65
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 65
ctggctgtac at                                                        12

<210> SEQ ID NO 66
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 66
catccaaact cttgag                                                    16

<210> SEQ ID NO 67
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 67
gctttcatgc acagga                                                    16

<210> SEQ ID NO 68
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
```

```
<221> NAME/KEY: misc_feature
<222> LOCATION: (1)..(16)
<223> OTHER INFORMATION: 3-10-3 LNA Gapmer - fully phosphorothioate

<400> SEQUENCE: 68
gaagttcatc aaagaa                                                          16

<210> SEQ ID NO 69
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 69
agttccttga tgtagt                                                          16

<210> SEQ ID NO 70
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 70
gttccttgat gtag                                                            14

<210> SEQ ID NO 71
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 71
ttccttgatg ta                                                              12

<210> SEQ ID NO 72
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 72
ttgcacagag atgatc                                                          16

<210> SEQ ID NO 73
<211> LENGTH: 16
<212> TYPE: DNA
```

```
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 73
gatgggcttg actttc                                                      16

<210> SEQ ID NO 74
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 74
atgggcttga cttt                                                        14

<210> SEQ ID NO 75
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 75
tgggcttgac tt                                                          12

<210> SEQ ID NO 76
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 76
caggcagaag acatct                                                      16

<210> SEQ ID NO 77
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 77
cccaaggcac tgcaga                                                      16

<210> SEQ ID NO 78
<211> LENGTH: 14
<212> TYPE: DNA
```

```
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 78
ccaaggcact gcag                                                     14

<210> SEQ ID NO 79
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 79
caaggcactg ca                                                       12

<210> SEQ ID NO 80
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 80
gctgacattc atagcc                                                   16

<210> SEQ ID NO 81
<211> LENGTH: 2999
<212> TYPE: DNA
<213> ORGANISM: Mus musculus

<400> SEQUENCE: 81
gaattcggtg gaagctacag acaagctcaa ggatggaggt gcagttaggg ctgggaaggg    60
tctacccacg gcccccatcc aagacctatc gaggagcgtt ccagaatctg ttccagagcg   120
tgcgcgaagc gatccagaac ccgggcccca ggcaccctga ggccgctaac atagcacctc   180
ccggcgcctg tttacagcag aggcaggaga ctagcccccg gcggcggcgg cggcagcagc   240
acactgagga tggttctcct caagcccaca tcagaggccc cacaggctac ctggcccctgg  300 aggaggaaca gcagccttca cagcagcagg cagcctccga gggccaccct gagagcagct   360
gcctccccga gcctggggcg gccaccgctc ctggcaaggg gctgccgcag cagccaccag   420
ctcctccaga tcaggatgac tcagctgccc catccacgtt gtccctgctg gccccacttt   480
tcccaggctt aagcagctgc tccgccgaca ttaaagacat tttgaacgag gccggcacca   540
tgcaacttct tcagcagcag caacaacagc agcagcacca acagcagcac caacagcacc   600
aacagcagca ggaggtaatc tccgaaggca gcagcgcaag agccagggag ccacggggg    660 ctccctcttc ctccaaggat agttacctag ggggcaattc aaccatatct gacagtgcca   720
aggagttgtg taaagcagtg tctgtgtcca tgggattggg tgtggaagca ttggaacatc   780
tgagtccagg ggaacagctt cggggagact gcatgtacgc gtcgctcctg ggaggtccac   840
```

```
ccgcggtgcg tcccactcct tgtgcgccgc tgcccgaatg caaaggtctt ccctggacg      900
aaggcccagg caaaagcact gaagagactg ctgagtattc ctctttcaag ggaggttacg      960
ccaaaggatt ggaaggtgag agcttggggt gctctggcag cagtgaagca ggtagctctg     1020
ggacacttga gatcccgtcc tctctgtctc tgtataaatc tggagcacta gacgaggcag     1080
cagcatacca gaatcgcgac tactacaact ttccgctggc tctgtccggg ccgccgcacc     1140
ccccgccccc tacccatcca cacgcccgta tcaagctgga gaacccattg gactacggca     1200
gcgcctgggc tgcggcggca gcgcaatgcc gctatgggga cttgggtagt ctacatggag     1260
ggagtgtagc cgggcccagc actggatcgc cccagccac cacctcttct tcctggcata     1320
ctctcttcac agctgaagaa ggccaattat atgggccagg aggcggggc ggcagcagca     1380
gcccaagcga tgccgggcct gtagcccct atggctacac tcggcccct caggggctga      1440
caagccagga gagtgactac tctgcctccg aagtgtggta tcctggtgga gttgtgaaca     1500
gagtacccta tcccagtccc aattgtgtca aaagtgaaat gggaccttgg atggagaact     1560
actccggacc ttatggggac atgcgtttgg acagtaccag ggaccatgtt ttacccatcg     1620
actattactt tccacccag aagacctgcc tgatctgtgg agatgaagct tctggctgtc     1680
actacggagc tctcacttgt ggcagctgca aggtcttctt caaaagagcc gctgaaggga     1740
aacagaagta tctatgtgcc agcagaaacg attgtaccat tgataaattt cggaggaaaa     1800
attgcccatc ttgtcgtctc cggaaatgtt atgaagcagg gatgactctg ggagctcgta     1860
agctgaagaa acttggaaat ctaaaactac aggaggaagg agaaaactcc aatgctggca     1920
gccccactga ggacccatcc cagaagatga ctgtatcaca cattgaaggc tatgaatgtc     1980
agcctatctt tcttaacgtc ctggaagcca ttgagccagg agtggtgtgt gccggacatg     2040
acaacaacca accagattcc tttgctgcct tgttatctag cctcaatgag cttggagaga     2100
ggcagcttgt gcatgtggtc aagtgggcca aggccttgcc tggcttccgc aacttgcatg     2160
tggatgacca gatggcggtc attcagtatt cctggatggg actgatggta tttgccatgg     2220
gttggcggtc cttcactaat gtcaactcca ggatgctcta ctttgcacct gacttggttt     2280
tcaatgagta ccgcatgcac aagtctcgga tgtacagcca gtgtgtgagg atgaggcacc     2340
tgtctcaaga gtttggatgg ctccaaataa ccccccagga attcctgtgc atgaaagcac     2400
tgctgctctt cagcattatt ccagtggatg ggctgaaaaa tcaaaaattc tttgatgaac     2460
ttcgaatgaa ctacatcaag gaactcgatc gcatcattgc atgcaaaaga aagaatccca     2520
catcctgctc aaggcgcttc taccagctca ccaagctcct ggattctgtg cagcctattg     2580
caagagagct gcatcagttc acttttgacc tgctaatcaa gtcccatatg gtgagcgtgg     2640
actttcctga aatgatggca gagatcatct ctgtgcaagt gcccaagatc ctttctggga     2700
aagtcaagcc catctatttc cacacacagt gaagatttgg aaaccctaat acccaaaacc     2760
caccttgttc cctttccaga tgtccttctgc ctgttatata actctgcact acttctctgc     2820
agtgccttgg gggaaattcc tctactgatg tacagtctgt cgtgaacagg ttcctcagtt     2880
ctatttcctg ggcttctcct tcttttttt tcttcttccc tccctctttc acctccat       2940
ggcacatttt gaatctgctg cgtattgtgg ctcctgcctt tgttttgatt tctgttgta      2999
```

<210> SEQ ID NO 82
<211> LENGTH: 3175
<212> TYPE: DNA
<213> ORGANISM: Macaca mulatta

<400> SEQUENCE: 82

```
cccaaaaaat aaaaacaaac aaaaacaaaa caaaacaaaa aaaacgaata agaaaaagg     60 taataactca gttcttattt gcacctactt ccagtggaca ctgaatttgg aaggtggagg    120
attcttgttt tttcttttaa gatcgggcat cttttgaatc tacccctcaa gtgttaagag    180
acagactgtg agcctagcag ggcagatctt gtccaccgtg tgtcttcttt tgcaggagac    240
tttgaggctg tcagagcgct ttttgcgtgg ttgctcccgc aagtttcctt ctctggagct    300
tcccgcaggt gggcagctag ctgcagcgac taccgcatca tcacagcctg ttgaactctt    360
ctgagcaaga aaggggagg cggggtaagg gaagtaggtg gaagattcag ccaagctcaa    420
ggatggaggt gcagttaggg ctggggaggg tctaccctcg gccgccgtcc aagacctacc    480
gaggagcttt ccagaatctg ttccagagcg tgcgcgaagt gatccagaac ccgggcccca    540
ggcacccaga ggccgcgagc gcagcacctc ccggcgccag tttgcagcag cagcagcagc    600
agcagcaaga aactagcccc cggcaacagc agcagcagca gcaggtgag gatggttctc    660 cccaagccca tcgtagaggc cccacaggct acctggtcct ggatgaggaa cagcagcctt    720
cacagcctca gtcagccccg gagtgccacc ccgagagagg ttgcgtccca gagcctggag    780
ccgccgtggc cgccggcaag gggctgccgc agcagctgcc agcacctccg gacgaggatg    840
actcagctgc cccatccacg ttgtctctgc tgggcccac tttccccggc ttaagcagct    900
gctccgccga ccttaaagac atcctgagcg aggccagcac catgcaactc cttcagcaac    960
agcagcagga agcagtatcc gaaggcagca gcagcgggag agcgagggag gcctcggggg   1020
ctcccacttc ctccaaggac aattacttag agggcacttc gaccatttct gacagcgcca   1080
aggagctgtg taaggcagtg tcggtgtcca tgggcttggg tgtggaggcg ttggagcatc   1140
tgagtccagg ggaacagctt cggggggatt gcatgtacgc cccagttttg ggagttccac   1200
ccgctgtgcg tcccactccg tgtgcccat tggccgaatg caaaggttct ctgctagacg   1260
acagcgcagg caagagcact gaagatactg ctgagtattc ccctttcaag ggaggttaca   1320
ccaaagggct agaaggcgag agcctaggct gctctggcag cgctgcagca gggagctccg   1380
ggacacttga actgccgtcc accctgtctc tctacaagtc cggagcactg gacgaggcag   1440
ctgcgtacca gagtcgcgac tactacaact ttccactggc tctggccggg ccgccgcccc   1500
ctccaccgcc tccccatccc cacgctcgca tcaagctgga gaaccgctg gactatggca   1560 gcgcctgggc ggctgcggcg gcgcagtgcc gctatgggga cctggcgagc ctgcatggcg   1620
cgggtgcagc gggacccggc tctgggtcac cctcagcggc cgcttcctca tcctggcaca   1680
ctctcttcac agccgaagaa ggccagttgt atggaccgtg tggtggtggg gcggcggcg   1740 gtggcggcgg cggcggcggc gcaggcgagg cgggagctgt agccccctac ggctacactc   1800
ggccacctca ggggctggcg ggccaggaag gcgacttcac cgcacctgat gtgtggtacc   1860
ctggcggcat ggtgagcaga gtgccctatc ccagtccac ttgtgtcaaa agcgagatgg   1920
gcccctggat ggatagctac tccggacctt acgggacat gcgtttggag actgccaggg   1980
accatgtttt gccaattgac tattactttc caccccagaa gacctgcctg atctgtggag   2040
atgaagcttc tgggtgtcac tatggagctc tcacatgtgg aagctgcaag gtcttcttca   2100
aaagagccgc tgaagggaaa cagaagtacc tgtgtgccag cagaaatgat tgcactattg   2160
ataaattccg aaggaaaaat tgtccatctt gccgtcttcg gaaatgttat gaagcaggga   2220
tgactctggg agcccggaag ctgaagaaac ttggtaatct gaaactacag gaggaaggag   2280
aggcttccag caccaccagc cccactgagg agacagccca gaagctgaca gtgtcacaca   2340
ttgaaggcta tgaatgtcag cccatctttc tgaatgtcct ggaggccatt gagccaggtg   2400
```

-continued

```
tggtgtgtgc tggacatgac aacaaccagc ccgactcctt cgcagccttg ctctctagcc    2460
tcaatgaact gggagagaga cagcttgtac atgtggtcaa gtgggccaag gccttgcctg    2520
gcttccgcaa cttacacgtg gacgaccaga tggctgtcat tcagtactcc tggatggggc    2580
tcatggtgtt tgccatgggc tggcgatcct tcaccaatgt caactccagg atgctctact    2640
ttgcccctga tctggttttc aatgagtacc gcatgcacaa atcccggatg tacagccagt    2700
gtgtccgaat gaggcacctc tctcaagagt tggatggct ccaaatcacc ccccaggaat    2760
tcctgtgcat gaaagcgctg ctactcttca gcattattcc agtggatggg ctgaaaaatc    2820
aaaaattctt tgatgaactt cgaatgaact acatcaagga actcgatcgt atcattgcat    2880
gcaaaagaaa aaatcccaca tcctgctcaa ggcgtttcta ccagctcacc aagctcctgg    2940
actccgtgca gcctattgcg agagagctgc atcagttcac ttttgacctg ctaatcaagt    3000
cacacatggt gagcgtggac tttccggaaa tgatggcaga gatcatctct gtgcaagtgc    3060
ccaagatcct ttctgggaaa gtcaagccca tctatttcca cacccagtga agcattggaa    3120
atccctattt cctcaccca gctcatgccc cctttcagat gtcttctgcc tgtta    3175
```

<210> SEQ ID NO 83
<211> LENGTH: 920
<212> TYPE: PRT
<213> ORGANISM: Homo sapiens

<400> SEQUENCE: 83

```
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Glu Thr Ser Pro Arg Gln Gln Gln Gln Gln Gly Glu Asp Gly Ser
                85                  90                  95

Pro Gln Ala His Arg Arg Gly Pro Thr Gly Tyr Leu Val Leu Asp Glu
            100                 105                 110

Glu Gln Gln Pro Ser Gln Pro Gln Ser Ala Leu Glu Cys His Pro Glu
        115                 120                 125

Arg Gly Cys Val Pro Glu Pro Gly Ala Ala Val Ala Ala Ser Lys Gly
    130                 135                 140

Leu Pro Gln Gln Leu Pro Ala Pro Pro Asp Glu Asp Asp Ser Ala Ala
145                 150                 155                 160

Pro Ser Thr Leu Ser Leu Leu Gly Pro Thr Phe Pro Gly Leu Ser Ser
                165                 170                 175

Cys Ser Ala Asp Leu Lys Asp Ile Leu Ser Glu Ala Ser Thr Met Gln
            180                 185                 190

Leu Leu Gln Gln Gln Gln Gln Glu Ala Val Ser Glu Gly Ser Ser Ser
        195                 200                 205

Gly Arg Ala Arg Glu Ala Ser Gly Ala Pro Thr Ser Ser Lys Asp Asn
    210                 215                 220

Tyr Leu Gly Gly Thr Ser Thr Ile Ser Asp Asn Ala Lys Glu Leu Cys
225                 230                 235                 240

Lys Ala Val Ser Val Ser Met Gly Leu Gly Val Glu Ala Leu Glu His
```

-continued

```
                    245                 250                 255
Leu Ser Pro Gly Glu Gln Leu Arg Gly Asp Cys Met Tyr Ala Pro Leu
                260                 265                 270

Leu Gly Val Pro Pro Ala Val Arg Pro Thr Pro Cys Ala Pro Leu Ala
            275                 280                 285

Glu Cys Lys Gly Ser Leu Leu Asp Asp Ser Ala Gly Lys Ser Thr Glu
        290                 295                 300

Asp Thr Ala Glu Tyr Ser Pro Phe Lys Gly Tyr Thr Lys Gly Leu
305                 310                 315                 320

Glu Gly Glu Ser Leu Gly Cys Ser Gly Ser Ala Ala Gly Ser Ser
                325                 330                 335

Gly Thr Leu Glu Leu Pro Ser Thr Leu Ser Leu Tyr Lys Ser Gly Ala
            340                 345                 350

Leu Asp Glu Ala Ala Ala Tyr Gln Ser Arg Asp Tyr Asn Phe Pro
        355                 360                 365

Leu Ala Leu Ala Gly Pro Pro Pro Pro Pro Pro His Pro His
    370                 375                 380

Ala Arg Ile Lys Leu Glu Asn Pro Leu Asp Tyr Gly Ser Ala Trp Ala
385                 390                 395                 400

Ala Ala Ala Ala Gln Cys Arg Tyr Gly Asp Leu Ala Ser Leu His Gly
                405                 410                 415

Ala Gly Ala Ala Gly Pro Gly Ser Gly Ser Pro Ser Ala Ala Ala Ser
            420                 425                 430

Ser Ser Trp His Thr Leu Phe Thr Ala Glu Glu Gly Gln Leu Tyr Gly
        435                 440                 445

Pro Cys Gly Gly Gly Gly Gly Gly Gly Gly Gly Gly Gly Gly
    450                 455                 460

Gly Gly Gly Gly Gly Gly Gly Gly Glu Ala Gly Ala Val Ala Pro
465                 470                 475                 480

Tyr Gly Tyr Thr Arg Pro Pro Gln Gly Leu Ala Gly Gln Glu Ser Asp
                485                 490                 495

Phe Thr Ala Pro Asp Val Trp Tyr Pro Gly Gly Met Val Ser Arg Val
            500                 505                 510

Pro Tyr Pro Ser Pro Thr Cys Val Lys Ser Glu Met Gly Pro Trp Met
        515                 520                 525

Asp Ser Tyr Ser Gly Pro Tyr Gly Asp Met Arg Leu Glu Thr Ala Arg
    530                 535                 540

Asp His Val Leu Pro Ile Asp Tyr Tyr Phe Pro Pro Gln Lys Thr Cys
545                 550                 555                 560

Leu Ile Cys Gly Asp Glu Ala Ser Gly Cys His Tyr Gly Ala Leu Thr
                565                 570                 575

Cys Gly Ser Cys Lys Val Phe Phe Lys Arg Ala Ala Glu Gly Lys Gln
            580                 585                 590

Lys Tyr Leu Cys Ala Ser Arg Asn Asp Cys Thr Ile Asp Lys Phe Arg
        595                 600                 605

Arg Lys Asn Cys Pro Ser Cys Arg Leu Arg Lys Cys Tyr Glu Ala Gly
    610                 615                 620

Met Thr Leu Gly Ala Arg Lys Leu Lys Lys Leu Gly Asn Leu Lys Leu
625                 630                 635                 640

Gln Glu Glu Gly Glu Ala Ser Ser Thr Thr Ser Pro Thr Glu Glu Thr
                645                 650                 655

Thr Gln Lys Leu Thr Val Ser His Ile Glu Gly Tyr Glu Cys Gln Pro
            660                 665                 670
```

```
Ile Phe Leu Asn Val Leu Glu Ala Ile Glu Pro Gly Val Val Cys Ala
        675                 680                 685

Gly His Asp Asn Asn Gln Pro Asp Ser Phe Ala Ala Leu Leu Ser Ser
        690                 695                 700

Leu Asn Glu Leu Gly Glu Arg Gln Leu Val His Val Val Lys Trp Ala
705                 710                 715                 720

Lys Ala Leu Pro Gly Phe Arg Asn Leu His Val Asp Asp Gln Met Ala
                725                 730                 735

Val Ile Gln Tyr Ser Trp Met Gly Leu Met Val Phe Ala Met Gly Trp
                740                 745                 750

Arg Ser Phe Thr Asn Val Asn Ser Arg Met Leu Tyr Phe Ala Pro Asp
        755                 760                 765

Leu Val Phe Asn Glu Tyr Arg Met His Lys Ser Arg Met Tyr Ser Gln
        770                 775                 780

Cys Val Arg Met Arg His Leu Ser Gln Glu Phe Gly Trp Leu Gln Ile
785                 790                 795                 800

Thr Pro Gln Glu Phe Leu Cys Met Lys Ala Leu Leu Leu Phe Ser Ile
                805                 810                 815

Ile Pro Val Asp Gly Leu Lys Asn Gln Lys Phe Phe Asp Glu Leu Arg
                820                 825                 830

Met Asn Tyr Ile Lys Glu Leu Asp Arg Ile Ile Ala Cys Lys Arg Lys
        835                 840                 845

Asn Pro Thr Ser Cys Ser Arg Arg Phe Tyr Gln Leu Thr Lys Leu Leu
850                 855                 860

Asp Ser Val Gln Pro Ile Ala Arg Glu Leu His Gln Phe Thr Phe Asp
865                 870                 875                 880

Leu Leu Ile Lys Ser His Met Val Ser Val Asp Phe Pro Glu Met Met
                885                 890                 895

Ala Glu Ile Ile Ser Val Gln Val Pro Lys Ile Leu Ser Gly Lys Val
                900                 905                 910

Lys Pro Ile Tyr Phe His Thr Gln
                915                 920

<210> SEQ ID NO 84
<211> LENGTH: 899
<212> TYPE: PRT
<213> ORGANISM: Mus musculus

<400> SEQUENCE: 84

Met Glu Val Gln Leu Gly Leu Gly Arg Val Tyr Pro Arg Pro Pro Ser
1                   5                   10                  15

Lys Thr Tyr Arg Gly Ala Phe Gln Asn Leu Phe Gln Ser Val Arg Glu
                20                  25                  30

Ala Ile Gln Asn Pro Gly Pro Arg His Pro Glu Ala Ala Asn Ile Ala
        35                  40                  45

Pro Pro Gly Ala Cys Leu Gln Gln Arg Gln Glu Thr Ser Pro Arg Arg
    50                  55                  60

Arg Arg Arg Gln Gln His Thr Glu Asp Gly Ser Pro Gln Ala His Ile
65                  70                  75                  80

Arg Gly Pro Thr Gly Tyr Leu Ala Leu Glu Glu Glu Gln Pro Ser
                85                  90                  95

Gln Gln Gln Ala Ala Ser Glu Gly His Pro Glu Ser Ser Cys Leu Pro
            100                 105                 110

Glu Pro Gly Ala Ala Thr Ala Pro Gly Lys Gly Leu Pro Gln Gln Pro
        115                 120                 125
```

```
Pro Ala Pro Pro Asp Gln Asp Asp Ser Ala Ala Pro Ser Thr Leu Ser
        130                 135                 140

Leu Leu Gly Pro Thr Phe Pro Gly Leu Ser Ser Cys Ser Ala Asp Ile
145                 150                 155                 160

Lys Asp Ile Leu Asn Glu Ala Gly Thr Met Gln Leu Leu Gln Gln Gln
                165                 170                 175

Gln Gln Gln Gln Gln His Gln Gln His Gln Gln His Gln Gln Gln
        180                 185                 190

Gln Glu Val Ile Ser Glu Gly Ser Ala Arg Ala Arg Glu Ala Thr
        195                 200                 205

Gly Ala Pro Ser Ser Ser Lys Asp Ser Tyr Leu Gly Gly Asn Ser Thr
210                 215                 220

Ile Ser Asp Ser Ala Lys Glu Leu Cys Lys Ala Val Ser Val Ser Met
225                 230                 235                 240

Gly Leu Gly Val Glu Ala Leu Glu His Leu Ser Pro Gly Glu Gln Leu
                245                 250                 255

Arg Gly Asp Cys Met Tyr Ala Ser Leu Leu Gly Gly Pro Pro Ala Val
                260                 265                 270

Arg Pro Thr Pro Cys Ala Pro Leu Pro Glu Cys Lys Gly Leu Pro Leu
                275                 280                 285

Asp Glu Gly Pro Gly Lys Ser Thr Glu Glu Thr Ala Glu Tyr Ser Ser
        290                 295                 300

Phe Lys Gly Gly Tyr Ala Lys Gly Leu Glu Gly Glu Ser Leu Gly Cys
305                 310                 315                 320

Ser Gly Ser Ser Glu Ala Gly Ser Ser Gly Thr Leu Glu Ile Pro Ser
                325                 330                 335

Ser Leu Ser Leu Tyr Lys Ser Gly Ala Leu Asp Glu Ala Ala Ala Tyr
                340                 345                 350

Gln Asn Arg Asp Tyr Tyr Asn Phe Pro Leu Ala Leu Ser Gly Pro Pro
        355                 360                 365

His Pro Pro Pro Thr His Pro His Ala Arg Ile Lys Leu Glu Asn
        370                 375                 380

Pro Leu Asp Tyr Gly Ser Ala Trp Ala Ala Ala Ala Gln Cys Arg
385                 390                 395                 400

Tyr Gly Asp Leu Gly Ser Leu His Gly Gly Ser Val Ala Gly Pro Ser
                405                 410                 415

Thr Gly Ser Pro Pro Ala Thr Thr Ser Ser Ser Trp His Thr Leu Phe
                420                 425                 430

Thr Ala Glu Glu Gly Gln Leu Tyr Gly Pro Gly Gly Gly Gly Gly Ser
        435                 440                 445

Ser Ser Pro Ser Asp Ala Gly Pro Val Ala Pro Tyr Gly Tyr Thr Arg
450                 455                 460

Pro Pro Gln Gly Leu Thr Ser Gln Glu Ser Asp Tyr Ser Ala Ser Glu
465                 470                 475                 480

Val Trp Tyr Pro Gly Gly Val Val Asn Arg Val Pro Tyr Pro Ser Pro
                485                 490                 495

Asn Cys Val Lys Ser Glu Met Gly Pro Trp Met Glu Asn Tyr Ser Gly
                500                 505                 510

Pro Tyr Gly Asp Met Arg Leu Asp Ser Thr Arg Asp His Val Leu Pro
        515                 520                 525

Ile Asp Tyr Tyr Phe Pro Pro Gln Lys Thr Cys Leu Ile Cys Gly Asp
        530                 535                 540

Glu Ala Ser Gly Cys His Tyr Gly Ala Leu Thr Cys Gly Ser Cys Lys
545                 550                 555                 560
```

Val Phe Phe Lys Arg Ala Ala Glu Gly Lys Gln Lys Tyr Leu Cys Ala
            565                 570                 575

Ser Arg Asn Asp Cys Thr Ile Asp Lys Phe Arg Arg Lys Asn Cys Pro
            580                 585                 590

Ser Cys Arg Leu Arg Lys Cys Tyr Glu Ala Gly Met Thr Leu Gly Ala
            595                 600                 605

Arg Lys Leu Lys Lys Leu Gly Asn Leu Lys Leu Gln Glu Glu Gly Glu
            610                 615                 620

Asn Ser Asn Ala Gly Ser Pro Thr Glu Asp Pro Ser Gln Lys Met Thr
625                 630                 635                 640

Val Ser His Ile Glu Gly Tyr Glu Cys Gln Pro Ile Phe Leu Asn Val
                    645                 650                 655

Leu Glu Ala Ile Glu Pro Gly Val Val Cys Ala Gly His Asp Asn Asn
                660                 665                 670

Gln Pro Asp Ser Phe Ala Ala Leu Leu Ser Ser Leu Asn Glu Leu Gly
            675                 680                 685

Glu Arg Gln Leu Val His Val Val Lys Trp Ala Lys Ala Leu Pro Gly
            690                 695                 700

Phe Arg Asn Leu His Val Asp Asp Gln Met Ala Val Ile Gln Tyr Ser
705                 710                 715                 720

Trp Met Gly Leu Met Val Phe Ala Met Gly Trp Arg Ser Phe Thr Asn
                725                 730                 735

Val Asn Ser Arg Met Leu Tyr Phe Ala Pro Asp Leu Val Phe Asn Glu
                740                 745                 750

Tyr Arg Met His Lys Ser Arg Met Tyr Ser Gln Cys Val Arg Met Arg
            755                 760                 765

His Leu Ser Gln Glu Phe Gly Trp Leu Gln Ile Thr Pro Gln Glu Phe
            770                 775                 780

Leu Cys Met Lys Ala Leu Leu Leu Phe Ser Ile Ile Pro Val Asp Gly
785                 790                 795                 800

Leu Lys Asn Gln Lys Phe Phe Asp Glu Leu Arg Met Asn Tyr Ile Lys
                805                 810                 815

Glu Leu Asp Arg Ile Ile Ala Cys Lys Arg Lys Asn Pro Thr Ser Cys
            820                 825                 830

Ser Arg Arg Phe Tyr Gln Leu Thr Lys Leu Leu Asp Ser Val Gln Pro
            835                 840                 845

Ile Ala Arg Glu Leu His Gln Phe Thr Phe Asp Leu Leu Ile Lys Ser
850                 855                 860

His Met Val Ser Val Asp Phe Pro Glu Met Met Ala Glu Ile Ile Ser
865                 870                 875                 880

Val Gln Val Pro Lys Ile Leu Ser Gly Lys Val Lys Pro Ile Tyr Phe
                885                 890                 895

His Thr Gln

<210> SEQ ID NO 85
<211> LENGTH: 895
<212> TYPE: PRT
<213> ORGANISM: Macaca mulatta

<400> SEQUENCE: 85

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

-continued

Val Ile Gln Asn Pro Gly Pro Arg His Pro Glu Ala Ala Ser Ala Ala
        35                  40                  45

Pro Pro Gly Ala Ser Leu Gln Gln Gln Gln Gln Gln Gln Gln Glu Thr
 50                  55                  60

Ser Pro Arg Gln Gln Gln Gln Gln Gln Gly Glu Asp Gly Ser Pro
 65                  70                  75                  80

Gln Ala His Arg Arg Gly Pro Thr Gly Tyr Leu Val Leu Asp Glu Glu
                 85                  90                  95

Gln Gln Pro Ser Gln Pro Gln Ser Ala Pro Glu Cys His Pro Glu Arg
                100                 105                 110

Gly Cys Val Pro Glu Pro Gly Ala Ala Val Ala Ala Gly Lys Gly Leu
            115                 120                 125

Pro Gln Gln Leu Pro Ala Pro Pro Asp Glu Asp Asp Ser Ala Ala Pro
130                 135                 140

Ser Thr Leu Ser Leu Leu Gly Pro Thr Phe Pro Gly Leu Ser Ser Cys
145                 150                 155                 160

Ser Ala Asp Leu Lys Asp Ile Leu Ser Glu Ala Ser Thr Met Gln Leu
                165                 170                 175

Leu Gln Gln Gln Gln Gln Glu Ala Val Ser Glu Gly Ser Ser Ser Gly
                180                 185                 190

Arg Ala Arg Glu Ala Ser Gly Ala Pro Thr Ser Ser Lys Asp Asn Tyr
            195                 200                 205

Leu Glu Gly Thr Ser Thr Ile Ser Asp Ser Ala Lys Glu Leu Cys Lys
210                 215                 220

Ala Val Ser Val Ser Met Gly Leu Gly Val Glu Ala Leu Glu His Leu
225                 230                 235                 240

Ser Pro Gly Glu Gln Leu Arg Gly Asp Cys Met Tyr Ala Pro Val Leu
                245                 250                 255

Gly Val Pro Pro Ala Val Arg Pro Thr Pro Cys Ala Pro Leu Ala Glu
            260                 265                 270

Cys Lys Gly Ser Leu Leu Asp Asp Ser Ala Gly Lys Ser Thr Glu Asp
            275                 280                 285

Thr Ala Glu Tyr Ser Pro Phe Lys Gly Gly Tyr Thr Lys Gly Leu Glu
290                 295                 300

Gly Glu Ser Leu Gly Cys Ser Gly Ser Ala Ala Gly Ser Ser Gly
305                 310                 315                 320

Thr Leu Glu Leu Pro Ser Thr Leu Ser Leu Tyr Lys Ser Gly Ala Leu
                325                 330                 335

Asp Glu Ala Ala Ala Tyr Gln Ser Arg Asp Tyr Tyr Asn Phe Pro Leu
            340                 345                 350

Ala Leu Ala Gly Pro Pro Pro Pro Pro Pro Pro His Pro His Ala
            355                 360                 365

Arg Ile Lys Leu Glu Asn Pro Leu Asp Tyr Gly Ser Ala Trp Ala Ala
370                 375                 380

Ala Ala Ala Gln Cys Arg Tyr Gly Asp Leu Ala Ser Leu His Gly Ala
385                 390                 395                 400

Gly Ala Ala Gly Pro Gly Ser Gly Ser Pro Ser Ala Ala Ser Ser
                405                 410                 415

Ser Trp His Thr Leu Phe Thr Ala Glu Glu Gly Gln Leu Tyr Gly Pro
            420                 425                 430

Cys Gly Gly Gly Gly Gly Gly Gly Gly Gly Gly Ala Gly
            435                 440                 445

Glu Ala Gly Ala Val Ala Pro Tyr Gly Tyr Thr Arg Pro Pro Gln Gly
450                 455                 460

```
Leu Ala Gly Gln Glu Gly Asp Phe Thr Ala Pro Asp Val Trp Tyr Pro
465                 470                 475                 480

Gly Gly Met Val Ser Arg Val Pro Tyr Pro Ser Pro Thr Cys Val Lys
                485                 490                 495

Ser Glu Met Gly Pro Trp Met Asp Ser Tyr Ser Gly Pro Tyr Gly Asp
            500                 505                 510

Met Arg Leu Glu Thr Ala Arg Asp His Val Leu Pro Ile Asp Tyr Tyr
        515                 520                 525

Phe Pro Pro Gln Lys Thr Cys Leu Ile Cys Gly Asp Glu Ala Ser Gly
    530                 535                 540

Cys His Tyr Gly Ala Leu Thr Cys Gly Ser Cys Lys Val Phe Phe Lys
545                 550                 555                 560

Arg Ala Ala Glu Gly Lys Gln Lys Tyr Leu Cys Ala Ser Arg Asn Asp
                565                 570                 575

Cys Thr Ile Asp Lys Phe Arg Arg Lys Asn Cys Pro Ser Cys Arg Leu
            580                 585                 590

Arg Lys Cys Tyr Glu Ala Gly Met Thr Leu Gly Ala Arg Lys Leu Lys
        595                 600                 605

Lys Leu Gly Asn Leu Lys Leu Gln Glu Glu Gly Glu Ala Ser Ser Thr
    610                 615                 620

Thr Ser Pro Thr Glu Glu Thr Ala Gln Lys Leu Thr Val Ser His Ile
625                 630                 635                 640

Glu Gly Tyr Glu Cys Gln Pro Ile Phe Leu Asn Val Leu Glu Ala Ile
                645                 650                 655

Glu Pro Gly Val Val Cys Ala Gly His Asp Asn Asn Gln Pro Asp Ser
            660                 665                 670

Phe Ala Ala Leu Leu Ser Ser Leu Asn Glu Leu Gly Glu Arg Gln Leu
        675                 680                 685

Val His Val Val Lys Trp Ala Lys Ala Leu Pro Gly Phe Arg Asn Leu
    690                 695                 700

His Val Asp Asp Gln Met Ala Val Ile Gln Tyr Ser Trp Met Gly Leu
705                 710                 715                 720

Met Val Phe Ala Met Gly Trp Arg Ser Phe Thr Asn Val Asn Ser Arg
                725                 730                 735

Met Leu Tyr Phe Ala Pro Asp Leu Val Phe Asn Glu Tyr Arg Met His
            740                 745                 750

Lys Ser Arg Met Tyr Ser Gln Cys Val Arg Met Arg His Leu Ser Gln
        755                 760                 765

Glu Phe Gly Trp Leu Gln Ile Thr Pro Gln Glu Phe Leu Cys Met Lys
    770                 775                 780

Ala Leu Leu Leu Phe Ser Ile Ile Pro Val Asp Gly Leu Lys Asn Gln
785                 790                 795                 800

Lys Phe Phe Asp Glu Leu Arg Met Asn Tyr Ile Lys Glu Leu Asp Arg
                805                 810                 815

Ile Ile Ala Cys Lys Arg Lys Asn Pro Thr Ser Cys Ser Arg Arg Phe
            820                 825                 830

Tyr Gln Leu Thr Lys Leu Leu Asp Ser Val Gln Pro Ile Ala Arg Glu
        835                 840                 845

Leu His Gln Phe Thr Phe Asp Leu Leu Ile Lys Ser His Met Val Ser
    850                 855                 860

Val Asp Phe Pro Glu Met Met Ala Glu Ile Ile Ser Val Gln Val Pro
865                 870                 875                 880

Lys Ile Leu Ser Gly Lys Val Lys Pro Ile Tyr Phe His Thr Gln
```

```
<210> SEQ ID NO 86
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 86
tggggagaac catcctcacc ctgc                                           24

<210> SEQ ID NO 87
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 87
tccaggacca ggtagcctgt gggg                                           24

<210> SEQ ID NO 88
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 88
tgttcccctg gactcagatg ctcc                                           24

<210> SEQ ID NO 89
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 89
tggggcacaa ggagtgggac gcac                                           24

<210> SEQ ID NO 90
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
```

```
<223> OTHER INFORMATION: nucleotide or nucleotide analogues - optionally
      phosphorothioate

<400> SEQUENCE: 90
ttcggctgtg aagagagtgt gcca                                            24

<210> SEQ ID NO 91
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 91
cgcttttgac acaagtggga ctgg                                            24

<210> SEQ ID NO 92
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 92
catagtgaca cccagaagct tcat                                            24

<210> SEQ ID NO 93
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 93
gagtcatccc tgcttcataa catt                                            24

<210> SEQ ID NO 94
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 94
gattaccaag tttcttcagc ttcc                                            24

<210> SEQ ID NO 95
<211> LENGTH: 24
<212> TYPE: DNA
<213> ORGANISM: artificial
```

```
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 95
aggccttggc ccacttgacc acgt                                              24

<210> SEQ ID NO 96
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 96
agcatcctgg agttgacatt ggtg                                              24

<210> SEQ ID NO 97
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 97
gacacactgg ctgtacatcc ggga                                              24

<210> SEQ ID NO 98
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 98
gagccatcca aactcttgag agag                                              24

<210> SEQ ID NO 99
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 99
cagtgctttc atgcacagga attc                                              24
```

```
<210> SEQ ID NO 100
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 100
attcgaagtt catcaaagaa tttt                                            24

<210> SEQ ID NO 101
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 101
atcgagttcc ttgatgtagt tcat                                            24

<210> SEQ ID NO 102
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 102
gcacttgcac agagatgatc tctg                                            24

<210> SEQ ID NO 103
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 103
aatagatggg cttgactttc ccag                                            24

<210> SEQ ID NO 104
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate
```

```
<400> SEQUENCE: 104
ataacaggca gaagacatct gaaa                                              24

<210> SEQ ID NO 105
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 105
attccccaag gcactgcaga ggag                                              24

<210> SEQ ID NO 106
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 106
atgggctgac attcatagcc ttca                                              24
```